(12) United States Patent
Beck et al.

US007309789B2

(10) Patent No.: US 7,309,789 B2
(45) Date of Patent: *Dec. 18, 2007

(54) 4-PHENYL SUBSTITUTED TETRAHYDROISOQUINOLINES AND THERAPEUTIC USE THEREOF

(75) Inventors: James P. Beck, Kalamazoo, MI (US); Anthony D. Pechulis, Guilderland, NY (US); Arthur E. Harms, Niskayuna, NY (US)

(73) Assignee: AMR Technology, Inc., Manchester Center, VT (US)

(*) Notice: Subject to any disclaimer, the term of this patent is extended or adjusted under 35 U.S.C. 154(b) by 79 days.

This patent is subject to a terminal disclaimer.

(21) Appl. No.: 11/438,725

(22) Filed: May 22, 2006

(65) Prior Publication Data

US 2006/0217409 A1    Sep. 28, 2006

Related U.S. Application Data

(62) Division of application No. 09/902,845, filed on Jul. 11, 2001, now Pat. No. 7,084,152.

(60) Provisional application No. 60/217,412, filed on Jul. 11, 2000.

(51) Int. Cl.
*C07D 471/02* (2006.01)
*C07D 495/02* (2006.01)

(52) U.S. Cl. ............................ 546/84; 546/80; 546/81

(58) Field of Classification Search ................ 546/81, 546/80, 84
See application file for complete search history.

(56) References Cited

U.S. PATENT DOCUMENTS

| | | | |
|---|---|---|---|
| 3,666,763 A | 5/1972 | Grethe et al. | |
| 3,947,456 A | 3/1976 | Rheiner | |
| 4,113,869 A | 9/1978 | Gardner | |
| 4,340,600 A | 7/1982 | Brenner et al. | |
| 4,564,613 A | 1/1986 | Boltze et al. | |
| 4,843,071 A | 6/1989 | Hohenwarter | |
| 4,902,710 A | 2/1990 | Foster et al. | |
| 5,444,070 A | 8/1995 | Moldt et al. | |
| 5,532,244 A | 7/1996 | Wong et al. | |
| 5,654,296 A | 8/1997 | Kato et al. | |
| 5,789,449 A | 8/1998 | Norden | |
| 6,121,261 A | 9/2000 | Glatt et al. | |
| 6,136,803 A | 10/2000 | Freedman et al. | |
| 6,579,885 B2 | 6/2003 | Beck et al. | |
| 6,911,453 B2 | 6/2005 | Hofmeister et al. | |
| 7,084,152 B2 * | 8/2006 | Beck et al. ................. | 514/291 |
| 2003/0203920 A1 | 10/2003 | Beck et al. | |
| 2005/0020597 A1 | 1/2005 | Beck et al. | |
| 2006/0025435 A1 | 2/2006 | Beck et al. | |
| 2006/0052378 A1 | 3/2006 | Molino et al. | |
| 2006/0063766 A1 | 3/2006 | Molino et al. | |
| 2006/0111385 A1 | 5/2006 | Molino et al. | |
| 2006/0111386 A1 | 5/2006 | Molino et al. | |
| 2006/0111393 A1 | 5/2006 | Molino et al. | |
| 2006/0111394 A1 | 5/2006 | Molino et al. | |
| 2006/0111395 A1 | 5/2006 | Molino et al. | |
| 2006/0111396 A1 | 5/2006 | Molino et al. | |

FOREIGN PATENT DOCUMENTS

| | | |
|---|---|---|
| CA | 2015114 | 10/1990 |
| CH | 538 477 | 8/1973 |
| DE | 2 062 001 | 7/1971 |
| EP | 0 140 070 A1 | 5/1985 |
| EP | 0 360 390 A1 | 3/1990 |
| EP | 0 394 989 B1 | 10/1990 |
| EP | 0 400 319 A1 | 12/1990 |
| EP | 0 428 434 A2 | 5/1991 |
| EP | 0 429 366 B1 | 5/1991 |
| EP | 0 430 771 B1 | 6/1991 |
| EP | 0 436 334 B1 | 7/1991 |
| EP | 0 443 132 B1 | 8/1991 |
| EP | 0 482 539 B1 | 4/1992 |
| EP | 0 498 069 B1 | 8/1992 |
| EP | 0 499 313 B1 | 8/1992 |
| EP | 0 512 901 B1 | 11/1992 |
| EP | 0 512 902 A1 | 11/1992 |
| EP | 0 514 273 A1 | 11/1992 |
| EP | 0 514 274 A1 | 11/1992 |
| EP | 0 514 275 A1 | 11/1992 |
| EP | 0 514 276 A1 | 11/1992 |
| EP | 0 515 681 A1 | 12/1992 |
| EP | 0 517 589 B1 | 12/1992 |
| EP | 0 520 555 A1 | 12/1992 |

(Continued)

OTHER PUBLICATIONS

Aihara et al., "Increasing 5-Lipoxygenase Inhibitory Activities by Oxidative Conversion of *o*-Methoxyphenols to Catechols Using a $Cu^{2+}$—Ascorbic Acid-$O_2$ System," *Chem. Pharm. Bull.* 38(3):842-844 (1990).

Berge et al., "Pharmaceutical Salts," *J. Pharm. Sci.* 66(1):1-19 (1977).

Banerji et al., "Studies on Single-Electron Transfer Reagents. Part IV Reaction of Nitrogen Heterocycles with Sodium Naphthalenide," *Tetrahedron* 50(30):9079-9096 (1994).

Blomberg et al., "The Barbier Reaction—A One Step Alternative for Syntheses via Organomagnesium Compounds," *Synthesis* pp. 18-30 (1977).

(Continued)

*Primary Examiner*—Charanjit S. Aulakh
(74) *Attorney, Agent, or Firm*—Nixon Peabody LLP

(57) ABSTRACT

Compounds are provided that, by way of their selective neurotransmitter binding useful for the treatment of various neurological and psychological disorders, e.g., ADHD. Such compounds are 4-phenyl substituted tetrahydroisoquinolines having the Formula IA, IB, IIA, IIB, IIIA or IIIC as set forth herein.

8 Claims, No Drawings

FOREIGN PATENT DOCUMENTS

| | | |
|---|---|---|
| EP | 0 522 808 A2 | 1/1993 |
| EP | 0 528 495 A1 | 2/1993 |
| EP | 0 532 456 B1 | 3/1993 |
| EP | 0 533 280 B1 | 3/1993 |
| EP | 0 536 817 A1 | 4/1993 |
| EP | 0 545 478 A1 | 6/1993 |
| EP | 0 558 156 A2 | 9/1993 |
| EP | 0 577 394 B1 | 1/1994 |
| EP | 0 585 913 B1 | 3/1994 |
| EP | 0 599 338 A2 | 6/1994 |
| EP | 0 599 538 A1 | 6/1994 |
| EP | 0 610 793 A1 | 8/1994 |
| EP | 0 634 402 A1 | 1/1995 |
| EP | 0 686 629 A2 | 12/1995 |
| EP | 0 693 489 A1 | 1/1996 |
| EP | 0 694 535 A1 | 1/1996 |
| EP | 0 699 674 A1 | 3/1996 |
| EP | 0 707 006 B1 | 4/1996 |
| EP | 0 708 101 B1 | 4/1996 |
| EP | 0 709 375 A2 | 5/1996 |
| EP | 0 709 376 A2 | 5/1996 |
| EP | 0 714 891 A1 | 6/1996 |
| EP | 0 723 959 A1 | 7/1996 |
| EP | 0 733 632 A1 | 9/1996 |
| EP | 0 776 893 A1 | 6/1997 |
| EP | 0 699 655 B1 | 9/1997 |
| EP | 0 520 555 B1 | 9/1999 |
| GB | 2 266 529 A | 11/1993 |
| GB | 2 268 931 A | 1/1994 |
| GB | 2 269 170 A | 2/1994 |
| GB | 2 269 590 A | 2/1994 |
| GB | 2 271 566 A | 4/1994 |
| GB | 2 271 774 A | 4/1994 |
| GB | 2 292 144 A | 2/1996 |
| GB | 2 293 168 A | 3/1996 |
| GB | 2 293 169 A | 3/1996 |
| GB | 2 302 689 A | 1/1997 |
| JP | 04193867 | 7/1992 |
| WO | WO 90/05525 | 5/1990 |
| WO | WO 90/05729 | 5/1990 |
| WO | WO 91/09844 | 7/1991 |
| WO | WO 91/18899 | 12/1991 |
| WO | WO 92/01688 | 2/1992 |
| WO | WO 92/06079 | 4/1992 |
| WO | WO 92/12151 | 7/1992 |
| WO | WO 92/15585 | 9/1992 |
| WO | WO 92/17449 | 10/1992 |
| WO | WO 92/20661 | 11/1992 |
| WO | WO 92/20676 | 11/1992 |
| WO | WO 92/21677 | 12/1992 |
| WO | WO 92/22569 | 12/1992 |
| WO | WO 93/00330 | 1/1993 |
| WO | WO 93/00331 | 1/1993 |
| WO | WO 93/01159 | 1/1993 |
| WO | WO 93/01165 | 1/1993 |
| WO | WO 93/01169 | 1/1993 |
| WO | WO 93/01170 | 1/1993 |
| WO | WO 93/06099 | 4/1993 |
| WO | WO 93/09116 | 5/1993 |
| WO | WO 93/10073 | 5/1993 |
| WO | WO 93/14084 | 7/1993 |
| WO | WO 93/14113 | 7/1993 |
| WO | WO 93/18023 | 9/1993 |
| WO | WO 93/19064 | 9/1993 |
| WO | WO 93/21155 | 10/1993 |
| WO | WO 93/21181 | 10/1993 |
| WO | WO 93/23380 | 11/1993 |
| WO | WO 93/24465 | 12/1993 |
| WO | WO 94/00440 | 1/1994 |
| WO | WO 94/01402 | 1/1994 |
| WO | WO 94/02461 | 2/1994 |
| WO | WO 94/02595 | 2/1994 |
| WO | WO 94/03429 | 2/1994 |
| WO | WO 94/03445 | 2/1994 |
| WO | WO 94/04494 | 3/1994 |
| WO | WO 94/04496 | 3/1994 |
| WO | WO 94/05625 | 3/1994 |
| WO | WO 94/07843 | 4/1994 |
| WO | WO 94/08997 | 4/1994 |
| WO | WO 94/10165 | 5/1994 |
| WO | WO 94/10167 | 5/1994 |
| WO | WO 94/10168 | 5/1994 |
| WO | WO 94/10170 | 5/1994 |
| WO | WO 94/11368 | 5/1994 |
| WO | WO 94/13639 | 6/1994 |
| WO | WO 94/13663 | 6/1994 |
| WO | WO 94/14767 | 7/1994 |
| WO | WO 94/15903 | 7/1994 |
| WO | WO 94/19320 | 9/1994 |
| WO | WO 94/19323 | 9/1994 |
| WO | WO 94/20500 | 9/1994 |
| WO | WO 94/26735 | 11/1994 |
| WO | WO 94/26740 | 11/1994 |
| WO | WO 94/29309 | 12/1994 |
| WO | WO 95/02595 | 1/1995 |
| WO | WO 95/04040 | 2/1995 |
| WO | WO 95/04042 | 2/1995 |
| WO | WO 95/06645 | 3/1995 |
| WO | WO 95/07886 | 3/1995 |
| WO | WO 95/07908 | 3/1995 |
| WO | WO 95/08549 | 3/1995 |
| WO | WO 95/11880 | 5/1995 |
| WO | WO 95/14017 | 5/1995 |
| WO | WO 95/15311 | 6/1995 |
| WO | WO 95/16679 | 6/1995 |
| WO | WO 95/17382 | 6/1995 |
| WO | WO 95/18124 | 7/1995 |
| WO | WO 95/18129 | 7/1995 |
| WO | WO 95/20575 | 8/1995 |
| WO | WO 95/21819 | 8/1995 |
| WO | WO 95/22525 | 8/1995 |
| WO | WO 95/23798 | 9/1995 |
| WO | WO 95/26338 | 10/1995 |
| WO | WO 95/28418 | 10/1995 |
| WO | WO 95/30674 | 11/1995 |
| WO | WO 95/30687 | 11/1995 |
| WO | WO 95/33744 | 12/1995 |
| WO | WO 96/05181 | 2/1996 |
| WO | WO 96/05193 | 2/1996 |
| WO | WO 96/05203 | 2/1996 |
| WO | WO 96/06094 | 2/1996 |
| WO | WO 96/07649 | 3/1996 |
| WO | WO 96/10562 | 4/1996 |
| WO | WO 96/16939 | 6/1996 |
| WO | WO 96/18643 | 6/1996 |
| WO | WO 96/20197 | 7/1996 |
| WO | WO 96/21661 | 7/1996 |
| WO | WO 96/29304 | 9/1996 |
| WO | WO 96/29317 | 9/1996 |
| WO | WO 96/29326 | 9/1996 |
| WO | WO 96/29328 | 9/1996 |
| WO | WO 96/31214 | 10/1996 |
| WO | WO 96/32385 | 10/1996 |
| WO | WO 96/37489 | 11/1996 |
| WO | WO 97/01553 | 1/1997 |
| WO | WO 97/01554 | 1/1997 |
| WO | WO 97/03066 | 1/1997 |
| WO | WO 97/08144 | 3/1997 |
| WO | WO 97/14671 | 4/1997 |
| WO | WO 97/17362 | 5/1997 |
| WO | WO 97/18206 | 5/1997 |
| WO | WO 97/19084 | 5/1997 |
| WO | WO 97/19942 | 6/1997 |
| WO | WO 97/21702 | 6/1997 |

| WO | WO 97/23458 | 7/1997 |
| WO | WO 97/36876 | 10/1997 |
| WO | WO 97/49710 | 12/1997 |
| WO | WO 98/40358 | 9/1998 |
| WO | WO 02/04455 A3 | 1/2002 |

OTHER PUBLICATIONS

Bobowski & Gottlieb, "4-Substituted 1,2,3,4-tetrahydro-3,3-dimethylisoquinolines. II.," *J. Heterocyclic Chem.* 19(1):21-27 (1982).
Brown & Dyke, "1,2-Dihydroisoquinolines. II. Berbine Synthesis," *Tetrahedron* 22(8):2429-35 (1966).
Brown & Dyke, "1,2-Dihydroisoquinolines. III. Dimerization," *Tetrahedron* 22(8):2437-2443 (1966).
Bundgaard, "Means to Enhance Penetration," *Adv. Drug Delivery Rev.* 8:1-38 (1992).
Bundgaard, *Design of Prodrugs*, Amsterdam, The Netherlands: Elsevier Science Publishers B.V. (1985) (Table of Contents only).
Chandrasekhar et al., "Highly Efficient Synthesis of 3-alkyl/aryl-4-aryl-1,2,3,4-tetrahydroisoquinolines from N,N-dibenzylaminols," *Tetrahedron Lett.* 43(10):1885-1888 (2002).
Cliffe et al., "(S)-N-tert-Butyl-3-(4-(2-methoxyphenyl)-piperazin-1-yl)-2-phenylpropanamide [(S)-WAY- 100135]: A Selective Antagonist at Presynaptic and Postsynaptic-5-HT$_{1A}$ Receptors," *J. Med. Chem.* 36:1509-10 (1993).
Dandridge et al., "Synthesis, Resolution, Absolute Stereochemistry, and Enantioselectivity of 3', 4'—Dihydroxynomifensine," *J. Med. Chem.* 27:28-35 (1984).
Dudley et al., "The Actions of Xylamine on Central Noradrenergic Neurons," *J. Pharm. Exp. Ther.* 217(3):834-840 (1981).
Gao et al., "Asymmetric Hetero Diels-Alder Reaction Catalyzed by Stable and Easily Prepared CAB Catalysts," *Tetrahedron* 50(4):979-988 (1994).
Georgiadis et al., "Synthesis and Complexation Properties of a Water-Soluble Optically Active Cyclophane Incorporating a 4-Naphthyl-1,2,3,4-tetrahydroisoquinoline Unit as a Chiral Spacer," *J. Org. Chem.* 56(10):3362-3369 (1991).
Greene et al., *Protective Groups in Organic Synthesis*, 2d. Ed., New York, New York: John Wiley & Sons, Inc. (1991) (Table of Contents only).
Hudlicky, "Fluorination with Diethylaminosulfur Trifluoride and Related Aminofluorosulfuranes," *Organic Reactions* 35:513-637 (1985).
Ishikura et al., "The Synthesis of 4-Substituted Isoquinoline Derivatives from Diethyl (4-Isoquinolyl) Borane," *Heterocycles* 26:1603-1610 (1987).
Jacob et al., "Dopamine Agonist Properties of N-Alkyl-4-(3,4-dihydroxyphenyl)-1,2,3,4-tetrahydroisoquinolines," *J. Med. Chem.* 24:1013-1015 (1981).
Jorgenson, "Preparation of Ketones from the Reaction of Organolithium Reagents with Carboxylic Acids," Dauben et al., eds., *Organic Reactions*, vol. 18, New York, New York: John Wiley & Sons, Inc., Chapter 1 (1970) (Table of Contents only).
Kakeya et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-Methoxyiminoacetamido]-3-Methyl-3-Cephem-4-Carboxylic Acid," *Chem. Pharm. Bull.* 32(2):692-698 (1984).
Kametani et al., "Studies on the Synthesis of Heterocyclic Compounds," *Tetrahedron* 31:235-238 (1975).
Kihara et al., "A Convenient Synthesis of 4-Substituted 1,2,3,4-Tetrahydroisoquinolin- 4-OLS by a Novel Intramolecular Barbier Reaction and by an Insertion Reaction: Reaction Scope and Limitations," *Tetrahedron* 48(1):67-78 (1992).
Kihara et al., "Synthesis and Enantioselectivity of Optically Active 1- and 3-Substituted 4-Phenyl-1,2,3,4-Tetrahydroisoquinolin-4-ols and Related Compounds As Norepinephrine Potentiators," *Chem. Pharm. Bull.* 43(9):1543-1546 (1995).
Kihara et al., "Synthesis and Pharmacological Evaluation of Phenolic 2-Methyl-4-Phenyl-1,2,3,4,-Tetrahydroisoquinolin-4-ols As New Norepinephrine Potentiator," *Drug Design Dis.* 11(3):175-183 (1994).

Knabe & Herbort, "Dehydrogenation of Tertiary Amines with Aercury (II) Acetate in the Presence of EDTA. XIII. Oxidative Dimerization of 6,7-dimethoxy-2-methyl-1,1-diethyl-1,2,3,4-tetrahydroisoquinoline," *Archiv. der Pharmazie. und Berichte der Deutschen Pharmazeutischen Gesellschaft* 300(9):774-783 (1967).
Knabe & Renz, "Synthesis of 3,4'-Biisoquinolines," *Archiv. der Pharmazie.* (Weinheim, Germany) 307(8):612-622 (1974).
Krogsgaard-Larsen et al., eds., *A Textbook of Drug Design and Development*, Chur, Switzerland: Harwood Academic Publishers GmbH (1991) (portion of Table of Contents only).
Larock, *Comprehensive Organic Transformations: A Guide to Functional Group Preparation*, New York, New York: VCH Publishers, Inc. (1989) (Table of Contents only).
Maryanoff et al., "Pyrroloisoquinoline Antidepressants. 2. In-Depth Exploration of Structure-Activity Relationships," *J. Med. Chem.* 30(8):1433-1454 (1987).
McOmie, ed., *Protective Groups in Organic Chemistry*, London: Plenum Press (1973) (Table of Contents only).
Middlemiss et al., "Centrally Active 5-HT Receptor Agonists and Antagonists," *Neurosci. Biobehavioral Rev.* 16:75-82 (1992).
Miller et al., "An Efficient Synthesis of 4-Aryl-1,2,3,4-Tetrahydroisoquinolines," *Synthetic Com.* 24(8):1187-1193 (1994).
Mondeshka et al., "Synthesis, Antiulcer and Antidepressive Activity of 4-(4-Halophenyl)-2-Phenyl-1,2,3,4-Tetrahydroisoquinolines," *Il Farmaco* 49:475-480 (1994).
Nielsen et al., "Glycolamide Esters as Biolabile Prodrugs of Carboxylic Acid Agents: Synthesis, Stability, Bioconversion, and Physicochemical Properties," *J. Pharm. Sci.* 77(4):285-298 (1988).
Salama et al., "Antigenic Determinants Responsible for the Reactions of Drug-Dependent Antibodies with Blood Cells," *Br. J. Haematol.* 78:535-539 (1991).
Seebach et al., "Alkylation of Amino Acids without Loss of the Optical Activity: Preparation of α-Substituted Proline Derivatives. A Case of Self-Reproduction of Chirality," *J. American Chem. Soc.* 105(16):5390-5398 (1983).
Stille, "Zur pharmakologischen Prufung von Antidepressive am Beispiel eines Dibenzodiazepins," *Arzneimittel-Forschung* 14:534-537 (1964) (English summary included).
Sugiura & Hamada, "Studies on Nitrogen-Containing Heterocyclic Compounds. XXXV. Syntheses and Reduction of 4-Amino-2-cyano-1,3-dimethoxy-1,2,3,4-tetrahydroisoquinolines," *Yakugaku Zasshi* 99(6):556-563 (1979).
Sugiura et al., "Synthesis and Stereochemistry of 3,7-Diazatricyclo[4.2.2.2$^{2,5}$]dodeca-9,11-dienes Derived By [4+4] Cyclodimerization of 2,3-Dihydroisoquinoline Derivatives," *Chem. Pharm. Bull.* 46(12):1862-1865 (1998).
Tirelli et al., "Differential Effects of Direct and Indirect Dopamine Agonists on the Induction of Gnawing in C57Bl/6J Mice," *J. Pharm. Exp. Therapy* 273(1):7-15 (1995).
Trepanier et al., "3,4-Dihydroisocarbostyril and 1,2,3,4-Tetrahydroisoquinoline Derivatives of Ephedrine," *J. Med. Chem.* 16(4):342-347 (1973).
Uno & Okada, "A Novel Method for the Synthesis of 4-Isoquinolinols," *J. Heterocyclic Chem.* 28(2):341-346 (1991).
Venkov et al., "A New Synthesis of 1,2,3,4-Tetrahydro-2-Methyl-4-Phenylisoquinolines," *Synthesis* 253-255 (1990).
Zára-Kaczián et al., "8-Amino-4-Aryl-2Methyl-1,2,3,4-Tetrahydroisoquinlines: Reactions of the Amino Group Via the Diazonium Salts," *Acta Chimica Hungarica*, 12(4):573-584 (1989).
CAS No. 53885-32-8.
CAS No. 53885-23-7.
Beilstein No. 455853 (CAS 71730-66-0).
Beilstein No. 4048047 (CAS 17074-38-3, 17074-39-4).
Beilstein No. 4102323 (CAS 53885-34-0).
Beilstein No. 4341479 (CAS 134021-24-2).
Beilstein No. 4494373 (CAS 82416-61-3).
Beilstein No. 4774688 (CAS 133160-36-8).
Beilstein No. 4787749 (CAS 133043-12-6, 133160-34-6, 133160-35-7).
Beilstein No. 4787750 (CAS 133043-12-6, 133160-34-6, 133160-35-7).
Beilstein No. 4787836 (CAS 133043-20-6, 133043-31-9).
Beilstein No. 4787837 (CAS 133043-20-6, 133043-31-9).

Beilstein No. 4788234 (CAS 133043-19-3, 133043-30-8).
Beilstein No. 4788235 (CAS 133043-19-3, 133043-30-8).
Beilstein No. 4789758 (CAS 133043-21-7, 133043-22-8).
Burrows et al., "Antidepressant Efficacy and Tolerability of the Selective Norepinephrine Reuptake Inhibitor Reboxetine: A Review," *J. Clin. Psychiatry* 59(Suppl. 14):4-7 (1998) (98819-76-2 REGISTRY (Reboxetine)).
Hyttel, "Pharmacological Characterization of Selective Serotonin Reuptake Inhibitors (SSRIs)," *Int. Clin. Psychopharmacol.* 9(Suppl. 1):19-26 (1994) (61869-08-7 REGISTRY (Paroxetine); 59729-32-7 REGISTRY (Citalopram); 79559-97-0 REGISTRY (Sertraline); 54910-89-3 REGISTRY (Fluoxetine); 54739-18-3 REGISTRY (Fluvoxamine)).

Müller, "Current St. John's Wort Research from Mode of Action to Clinical Efficacy," *Pharmacological Research* 47:101-109 (2003).
Desai et al., "Relationship Between in Vivo Occupancy at the Dopamine Transporter and Behavioral Effects of Cocaine, GBR 12909 [1-{2-[Bis-(4-fluorophenyl)methoxy]ethyl}-4-(3-phenylpropyl)piperazine], and Benztropine Analogs," *JPET* 315(1):397-404 (2005).
Cherpillod et al., "A Controlled Trial with Diclofensine, A New Psychoactive Drug, in the Treatment of Depression," *J. Int. Med. Res.* 9(5):324-329 (1981).

* cited by examiner

US 7,309,789 B2

4-PHENYL SUBSTITUTED TETRAHYDROISOQUINOLINES AND THERAPEUTIC USE THEREOF

This application is a division of U.S. patent application Ser. No. 09/902,845, filed Jul. 11, 2001 now U.S. Pat, No. 7,084,152, which claims benefit of U.S. Provisional Patent Application Ser. No. 60/217,412, filed Jul. 11, 2000, which are hereby incorporated by reference in their entirety.

FIELD OF THE INVENTION

The present invention relates to compounds, compositions, and methods for the treatment of various neurological and psychological disorders. In particular, the present invention relates to such compounds, compositions and methods wherein the compounds are novel 4-phenyl substituted tetrahydroisoquinoline derivatives.

BACKGROUND OF THE INVENTION

The treatment of a variety of neurological and psychiatric disorders, e.g., attention deficit-hyperactivity disorder ("ADHD"), is characterized by a number of side effects believed to be due to the lack of appropriate selectivities in the compounds used for the treatment, e.g., to the compounds' inability to selectively block certain neurochemicals, and not others. ADHD, for example, is a disease affecting 3-6% of school age children, and is also recognized in percentage of adults. Aside form hampering performance at school and at work ADHD is a significant risk factor for the subsequent development of anxiety disorders, depression, conduct disorder and drug abuse. Since current treatment regimes require psychostimulants, and since a substantial number of patients (30%) are resistant to stimulants or cannot tolerate their side effects, there is a need for a new drug or class of drugs which treats ADHD and does not have resistance or side effect problems. In addition, methylphenidate, the current drug of choice for the treatment of ADHD, induces a number of side effects; these include anorexia, insomnia and jittery feelings, tics, as well as increased blood pressure and heart rate secondary to the activation of the sympathetic nervous system. Methylphenidate also has a high selectivity for the dopamine transporter protein over the norepinephrine transporter protein (DAT/NET Ki ratio of 0.1), which can lead to addiction liability and requires multiple doses per day for optimal efficacy.

This invention provides an alternative to such known treatments with its novel 4-phenyl tetrahydroisoquinoline derivatives, said compounds being nowhere described in the art. U.S. Pat. No. 3,947,456 (the "'456 patent), for example, describes 4-phenyl substituted tetrahydroisoquinolines of the formula:

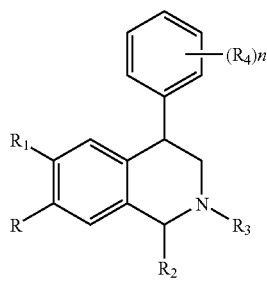

wherein R is hydroxy or lower alkoxy; the '456 patent does not describe any other groups at this position, let alone the substituents available at the position ($R^4$) in the compounds provided herein. Phenyl-substituted tetrahydroisoquinolines are also described in Mondeshka et al (Il Farmaco, 1994, 49 pp. 475-481). However, the compounds described therein are not those provided herein.

SUMMARY OF THE INVENTION

This invention provides a compound of the Formula IA, IB, IIA, IIB, IIIA and IIIB, as follows:

IA

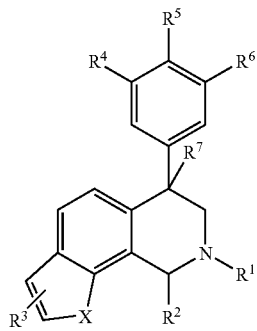

IB

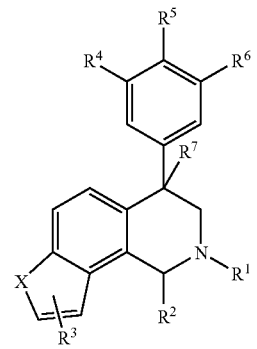

IIA

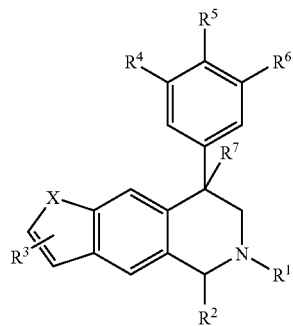

IIB

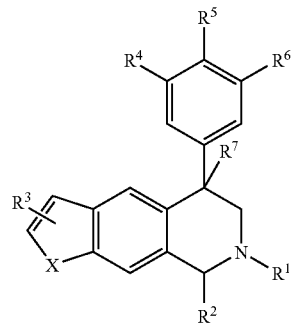

-continued

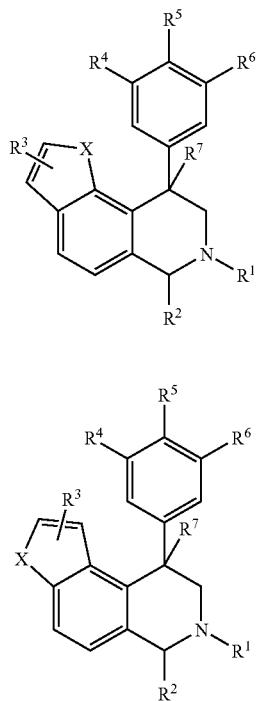

IIIA

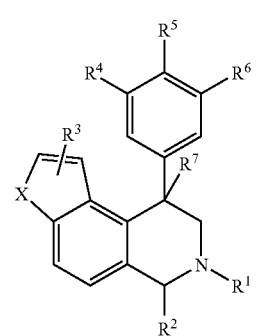

IIIB

IA

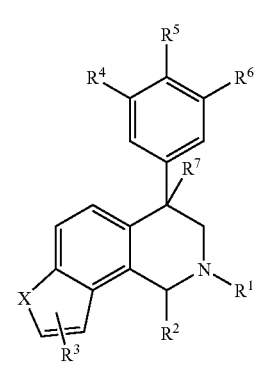

IB

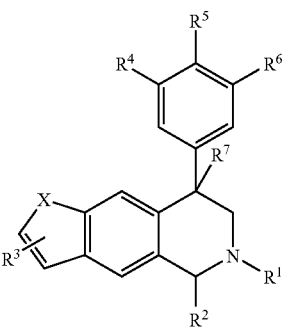

IIA

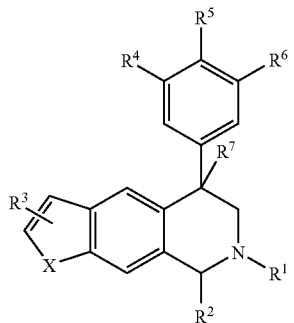

IIB wherein $R^1$-$R^{13}$ are as described herein. In one embodiment, $R^1$ is $C_1$-$C_6$ alkyl; $R^2$ is H, $C_1$-$C_6$ alkyl, $C_3$-$C_6$ cycloalkyl, or $C_1$-$C_6$ haloalkyl; $R^3$ is at each occurrence thereof independently H, halogen, $C_1$-$C_6$ alkyl, or $C_1$-$C_6$ alkyl substituted with from 1 to 3 of $OR^8$ or $NR^8R^9$; $R^4$, $R^5$ and $R^6$ are each independently H or are selected at each occurrence thereof from halogen, —$OR^{10}$, —$NR^{10}R^{11}$, —$NR^{10}C(O)R^{11}$, —$S(O)_nR^{11}$, —CN, —$C(O)R^{11}$, —$C(O)_2R^{11}$, $C(O)NR^{11}R^{12}$, $C_1$-$C_6$ alkyl, $C_3$-$C_6$ cycloalkyl, or $C_4$-$C_7$ cycloalkylalkyl, and wherein each of $C_1$-$C_6$ alkyl, $C_3$-$C_6$ cycloalkyl, and $C_4$-$C_7$ cycloalkylalkyl is optionally substituted with from 1 to 3 substituents independently selected at each occurrence thereof from $C_1$-$C_3$ alkyl, halogen, —CN, —$OR^8$, —$NR^8R^9$ and phenyl which is optionally substituted 1-3 times with halogen, —CN, $C_1$-$C_4$ alkyl, $C_1$-$C_4$ haloalkyl, —$OR^8$, or —$NR^8R^9$; or $R^5$ and $R^6$ may be —O—$C(R^{11})_2$—O—; and, $R^7$—$R^{13}$, n, and X are as described herein.

Compounds provided herein block the reuptake of norephinephrine, dopamine, and serotonin with particular selectivity ratios, e.g., being more selective for the norepinephrine transporter (NET) protein than the dopamine transporter (DAT) protein or serotonin transporter (SERT) proteins. Hence, the compounds are useful for selectively treating a variety of neurological and psychological disorders.

Also provided herein is a pharmaceutical composition comprising a pharmaceutically acceptable carrier and a therapeutically effective amount of a compound of Formula IA, IB, IIA, IIB, IIIA or IIIB. Further provided is a method of treating a mammal afflicted with a neurological or psychological disorder selected from the group consisting of attention deficit-hyperactivity disorder, anxiety, depression, post-traumatic stress disorder, supranuclear palsy, feeding disorders, obsessive compulsive disorder, analgesia, smoking cessation, panic attacks, Parkinson's and phobia, said method comprising administering to the mammal the aforementioned pharmaceutical composition.

DETAILED DESCRIPTION OF THE INVENTION

This invention provides a compound of the Formula IA, IB, IIA, IIB, IIIA or IIIB, as follows:

-continued

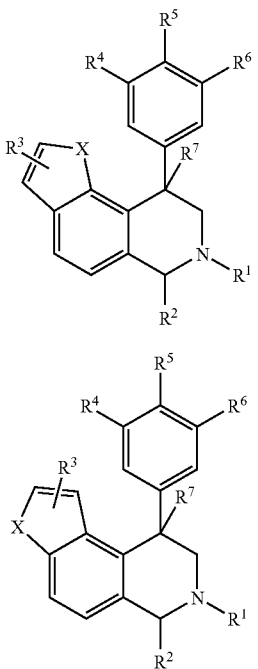

IIIA

IIIB wherein:

R$^1$ is selected from the group consisting of C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl and benzyl, each of which is optionally substituted with 1 to 3 substituents independently selected at each occurrence from C$_1$-C$_3$ alkyl, halogen, —CN, —OR$^8$ and —NR$^8$R$^9$;

R$^2$ is selected from the group consisting of H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl and C$_1$-C$_6$ haloalkyl;

R$^3$ is selected from the group consisting of H, halogen, C$_1$-C$_6$ alkyl, C$_1$-C$_6$ haloalkyl and C$_3$-C$_6$ cycloalkyl, wherein C$_1$-C$_6$ alkyl, C$_1$-C$_6$ haloalkyl and C$_3$-C$_6$ cycloalkyl are optionally substituted with 1 to 3 substituents selected independently at each occurrence from OR$^8$ and NR$^8$R$^9$;

R$^4$, R$^5$ and R$^6$ are each independently selected at each occurrence thereof from the group consisting of H, halogen, —OR$^{10}$, —NO$_2$, NR$^{10}$R$^{11}$, —NR$^{10}$C(O)R$^{11}$, —NR$^{10}$C(O)NR11R$^{12}$, —S(O)$_n$R$^{11}$, —CN, —C(O)R$^{11}$, —C(O)$_2$R$^{11}$; —C(O)NR$^{11}$R$^{12}$, C$_1$-C$_6$ alkyl, C$_2$-C$_6$ alkenyl, C$_2$-C$_6$ alkynyl, C$_3$-C$_6$ cycloalkyl and C$_4$-C$_7$ cycloalkylalkyl, wherein each of C$_1$-C$_6$ alkyl, C$_2$-C$_6$ alkenyl, C$_2$-C$_6$ alkynyl, C$_3$-C$_6$ cycloalkyl and C$_4$-C$_7$ cycloalkylalkyl are optionally substituted with 1 to 3 substituents independently selected at each occurrence from C$_1$-C$_3$ alkyl, halogen, =O, —CN, —OR$^8$, —NR$^8$R$^9$ and phenyl, and wherein phenyl is optionally substituted 1-3 substituents selected independently at each occurrence from halogen, —CN, C$_1$-C$_4$ alkyl, C$_1$-C$_4$ haloalkyl, —OR$^8$ and —NR$^8$R$^9$;

alternatively R$^5$ and R$^6$ are —O—C(R$^{11}$)$_2$—O—;

R$^7$ is selected from the group consisting of H, halogen and OR$^{10}$;

R$^8$ and R$^9$ are each independently selected from the group consisting of H, C$_1$-C$_4$ alkyl, C$_1$-C$_4$ haloalkyl, C$_1$-C$_4$ alkoxyalkyl, C$_1$-C$_4$ alkoxyalkylalkyl, C$_3$-C$_6$ cycloaklyl, C$_4$-C$_7$ cyclooalkylalkyl, —C(O)R$^{12}$, phenyl and benzyl, wherein phenyl and benzyl are optionally substituted with 1 to 3 substituents selected independently at each occurrence from halogen, cyano, C$_1$-C$_4$ alkyl, C$_1$-C$_4$ haloalkyl, C$_1$-C$_4$ alkoxy and C$_1$-C$_4$ haloalkoxy, or R$^8$ and R$^9$ are taken together with the nitrogen to which they are attached to form a piperidine, pyrrolidine, piperazine, N-methylpiperazine, morpholine, or thiomorpholine ring;

R$^{10}$ is selected from the group consisting of H, C$_1$-C$_4$ alkyl, C$_1$-C$_4$ haloalkyl, C$_1$-C$_4$ alkoxyalkyl, C$_3$-C$_6$ cycloaklyl, C$_4$-C$_7$ cycloalkylalkyl, —C(O)R$^{12}$, phenyl and benzyl, wherein phenyl and benzyl are optionally substituted with 1 to 3 substituents selected independently at each occurrence from halogen, —NH$_2$, —OH, cyano, C$_1$-C$_4$ alkyl, C$_1$-C$_4$ haloaklyl, C$_1$-C$_4$ alkoxy and C$_1$-C$_4$ haloalkoxy;

R$^{11}$ is selected from the group consisting of H, C$_1$-C$_4$ alkyl, C$_1$-C$_4$ haloalkyl, C$_1$-C$_4$ alkoxyalkyl, C$_3$-C$_6$ cycloalkyl, C$_4$-C$_7$ cycloalkylalkyl, phenyl and benzyl, where phenyl and benzyl are optionally substituted with 1 to 3 substituents selected independently at each occurrence from halogen, —NH$_2$, —OH, cyano, C$_1$-C$_4$ alkyl, C$_1$-C$_4$ haloalkyl, C$_1$-C$_4$ alkoxy and C$_1$-C$_4$ haloalkoxy, or R$^{10}$ and R$^{11}$ are taken together with the nitrogen to which they are attached to form a piperidine, pyrrolidine, N-methylpiperazine, morpholine, or thiomorpholine ring, with the proviso that only one of R$^8$ and R$^9$ or R$^{10}$ and R$^{11}$ are taken together with the nitrogen to which they are attached to form a piperidine, pyrrolidine, piperaine, N-methylpiperazine, morpholine, or thiomorpholine ring;

R$^{12}$ is selected from the group consisting of C$_1$-C$_4$ alkyl, C$_1$-C$_4$ haloalkyl and phenyl;

X is selected from the group consisting of 0, NR$^{13}$ and S, with the proviso that X is not NR$^{13}$ when a compound is of Formula (IA);

the ring containing X is selected from furan, pyrrole, thiophene, dihydrofuran, dihydropyrrole, and dihydrothiophene;

n is 0, 1, or 2; and,

R$^{13}$ is selected from the group consisting of H, C$_1$-C$_6$ alkyl, benzyl and phenyl, wherein C$_1$-C$_6$ alkyl, benzyl and phenyl are optionally substituted with 1-3 substituents independently at each occurrence from halogen, —NH$_2$, —OH, cyano, C$_1$-C$_4$ alkyl, C$_1$-C$_4$ haloalkyl, C$_1$-C$_4$ alkoxy and C$_1$-C$_4$ haloalkoxy.

"Alkyl" means saturated hydrocarbon chains, branched or unbranched, having the specified number of carbon atoms. "Alkenyl" means hydrocarbon chains of either a straight or branched configuration and one or more unsaturated carbon-carbon bonds, which may occur in any stable point along the chain, such as ethenyl, propenyl, and the like. "Alkynyl" means hydrocarbon chains of either a straight or branched configuration and one or more triple carbon-carbon bonds, which may occur in any stable point along the chain, such as ethynyl, propynyl, and the like. "Alkoxy" means an alkyl group of indicated number of carbon atoms attached through an oxygen bridge. "Cycloalkyl" means saturated ring groups, including mono-, bi-, or poly-cyclic ring systems, such as cyclopropyl, cyclobutyl, cyclopentyl, and the so forth. "Halo" or "halogen" means fluoro, chloro, bromo, and iodo. "Haloalkyl" means both branched and straight-chain alkyls having the specified number of carbon atoms, substituted with 1 or more halogen. "Haloalkoxy" means an alkoxy group substituted by at least one halogen atom.

"Substituted" or "substitution" of an atom means that one or more hydrogen on the designated atom is replaced with a selection from the indicated group, provided that the designated atom's normal valence is not exceeded. "Unsubstituted" atoms bear all of the hydrogen atoms dictated by their valency. When a substituent is keto (ie. C=O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

One embodiment of this invention are those compounds wherein: $R^1$ is $C_1$-$C_6$ alkyl; $R^2$ is H, $C_1$-$C_6$ alkyl, $C_3$-$C_6$ cycloalkyl, or $C_1$-$C_6$ haloalkyl; $R^3$ is at each occurrence thereof independently H, halogen, $C_1$-$C_6$ alkyl, or $C_1$-$C_6$ alkyl substituted with from 1 to 3 of $OR^8$ or $NR^8R^9$; $R^4$, $R^5$ and $R^6$ are each independently H or are selected at each occurrence thereof from halogen, $-OR^{10}$, $-NR^{10}R^{11}$, $-NR^{10}C(O)R^{11}$, $-S(O)_nR^{11}$, $-CN$, $-C(O)R^{11}$, $-C(O)_2R^{11}$, $-C(O)NR^{11}R^{12}$, $C_1$-$C_6$ alkyl $C_3$-$C_6$ cycloalkyl, or $C_4$-$C_7$ cycloalkylalkyl, and wherein each of $C_1$-$C_6$ alkyl, $C_3$-$C_6$ cycloalkyl, and $C_4$-$C_7$ cycloalkylalkyl is optionally substituted with from 1 to 3 substituents independently selected at each occurrence thereof from $C_1$-$C_3$ alkyl, halogen, $-CN$, $-OR^8$, $-NR^8R^9$ and phenyl which is optionally substituted 1-3 times with halogen, $-CN$, $C_1$-$C_4$ alkyl, $C_1$-$C_4$ haloalkyl, $-OR^8$, or $-NR^8R^9$; or $R^5$ and $R^6$ may be $-O-C(R^{11})_2-O-$; and, $R^7-R^{13}$, n, and X are described above.

Within these embodiments, the selection of a particular substituent on any one position of a compound does not necessarily affect the selection of a substituent at another position on the same compound—that is, compounds provided herein have any of the substituents at any of the positions. For example, as described hereinabove, $R^1$ is preferably, for example, $C_1$-$C_6$ alkyl—the selection of $R^1$ as any one of $C_1$, $C_2$, $C_3$, $C_4$, $C_5$, or $C_6$ alkyl, does not limit the choice of $R^2$ in particular to any one of H, $C_1$-$C_6$ alkyl, $C_3$-$C_6$ cycloalkyl, or $C_1$-$C_6$ haloalkyl. Rather, for $R^1$ as any of $C_1$, $C_2$, $C_3$, $C_4$, $C_5$, or $C_6$ alkyl, $R^2$ is any of H, $C_1$, $C_2$, $C_3$, $C_4$, $C_5$, or $C_6$ alkyl or $C_3$, $C_4$, $C_5$, or $C_6$ cylcoalkyl, or $C_1$, $C_2$, $C_3$, $C_4$, $C_5$, or $C_6$ haloalkyl. Similarly, the selection of $R^2$ in particular to any one of H, $C_1$, $C_2$, $C_3$, $C_4$, $C_5$, or $C_6$ alkyl or $C_3$, $C_4$, $C_5$, or $C_6$ cylcoalkyl, or $C_1$, $C_2$, $C_3$, $C_4$, $C_5$, or $C_6$ haloalkyl does not limit selection of $R^3$ in particular to any one of its constituent members.

In another embodiment, $R^1$ is methyl, ethyl, propyl or isopropyl; $R^2$ is H or $C_1$-$C_6$ alkyl, and $R^3$ is H, halogen, or $C_1$-$C_6$ alkyl, wherein $C_1$-$C_6$ alkyl is optionally substituted with from 1-3 $OR^8$; $R^4$ and $R^5$ and $R^6$ are each independently H, halogen, $-OR^{10}$, $-S(O)_nR^{11}$, $-NR^{10}R^{11}$, $-C(O)R^{11}$, or $C_1$-$C_6$alkyl wherein $C_1$-$C_6$alkyl is optionally substituted as described above; and $R^7-R^{13}$ and X are as described above. In yet another embodiment, $R^1$ is methyl; $R^2$ and $R^3$ are H; $R^4$ and $R^5$ and $R^6$ are each independently H, F, Cl, $-OH$, $C_1$-$C_3$ alkoxy, or $C_1$-$C_3$ alkyl; $R^7$ is H, F, $-OH$, or $-OCH_3$ and; $R^8-R^{13}$ and X are as described above.

In one embodiment compounds include, for example and without limitation, those compounds set forth in Tables I-VIA hereinbelow. That is such compounds include those having the following formula (see Tables 1-1B).

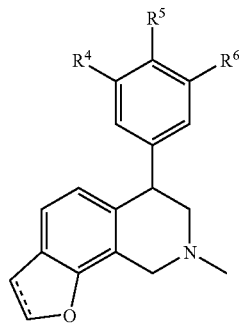

wherein the oxygen-containing ring is either saturated or unsaturated, $R^4$ is H, Cl or F, $R^5$ is H, F or Me and $R^6$ is H or F.

In another embodiment compounds include those having the following formula (see Tables 2-2B).

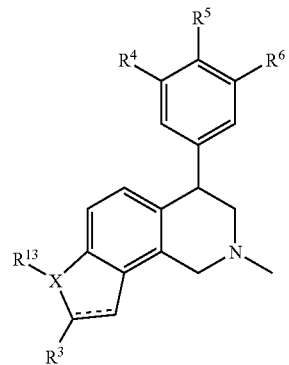

wherein X is O, S or N, the X-containing ring is either saturated or unsaturated, $R^3$ is H, Me, Et or MEOH, $R^4$ and $R^6$ are each H, F or Cl, $R^5$ is H. F. Cl or OMe and $R^{13}$ when present, is $C_1$-$C_6$ alkyl. Yet in another embodiment compounds further include those having the following formula (see Tables 3-3A).

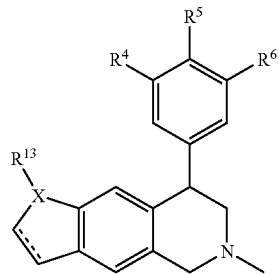

wherein X is O or N, the X-containing ring is either saturated or unsaturated, $R^4$, $R^5$ and $R^6$ are each H and $R^{13}$ when present, is H or $C_1$-$C_6$ alkya Still another embodiment includes compounds having the following formula (see Tables 4-4B).

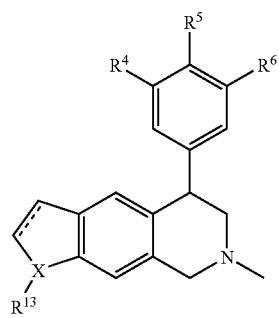

wherein X is O or N, the X-containing ring is either saturated or unsaturated, $R^4$is H, $R^5$ is H, Cl, F or Bn, $R^6$ is H, Cl or F and $R^{13}$ is H or $C_1$-$C_6$ alkyl. Further embodiments include those compounds having the following formula (see Table 5).

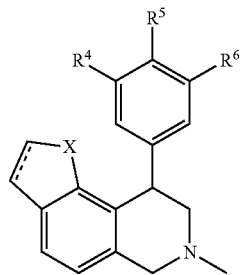

wherein X is O or S, the X-containing ring is either saturated or unsaturated, $R^4$ is H, $R^5$ is H, Cl, F or OMe, $R^6$ is H, Cl or F and $R^{13}$ is $C_1$-$C_6$ alkyl. In yet another embodiment compounds include those having the following formula (see Tables 6-6A)

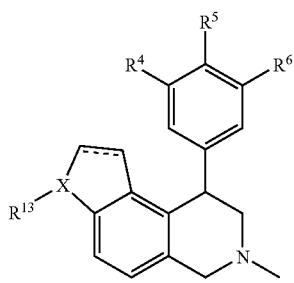

wherein X is O, the X-containing ring is either saturated or unsaturated, $R^4$ is H, $R^5$ is H or F, $R^6$ is H or F.

Each of the stereoisomeric forms of this invention's compounds is also provided for herein. That is, the compounds can have one or more asymmetric centers or planes, and all chiral (enantiomeric and diastereomeric) and racemic forms of the compounds are included in the present invention. Many geometric isomers of olefins, C=N double bonds, and the like can also be present in the compounds, and all such stable isomers are contemplated in the present invention. Compounds are isolated in either the racemic form, or in the optically pure form, for example, by chiral chromatography or chemical resolution of the racemic form.

Pharmaceutically acceptable salts of this invention's compounds are also provided for herein. In this regard, the phrase "pharmaceutically acceptable" is employed to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Prodrug forms of this invention's compounds are also provided for herein. Such "prodrugs" are compounds comprising this invention's compounds and moieties covalently bound to the parent compounds such that the portions of the parent compound most likely to be involved with toxicities in subjects to which the prodrugs have been administered are blocked from inducing such effects. However, the prodrugs are also cleaved in the subjects in such a way as to release the parent compound without unduly lessening its therapeutic potential. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, and benzoate derivatives of alcohol, and amine functional groups in the compounds of Formulae (I-III).

Radiolabelled compounds, i.e. wherein one or more of the atoms described are replaced by a radioactive isotope of that atom (e.g. C replaced by $^{14}$C or by $^{11}$C, and H replaced by $^{3}$H or $^{18}$F), are also provided for herein. Such compounds have a variety of potential uses, e.g. as standards and reagents in determining the ability of a potential pharmaceutical to bind to neurotransmitter proteins, or for imaging compounds of this invention bound to biological receptors in vivo or in vitro.

This invention provides compositions containing the compounds described herein, including, in particular, pharmaceutical compositions comprising therapeutically effective amounts of the compounds and pharmaceutically acceptable carriers. "Therapeutically effective amounts" are any amounts of the compounds effective to ameliorate, lessen, inhibit or prevent the particular condition for which a subject is being treated. Such amounts generally vary according to a number of factors well within the purview of ordinarily skilled artisans given the description provided herein to determine and account for. These include, without limitation: the particular subject, as well as its age, weight, height, general physical condition and medical history; the particular compound used, as well as the carrier in which it is formulated and the route of administration selected for it; and, the nature and severity of the condition being treated. Therapeutically effective amounts include optimal and suboptimal doses, and can be determined in a variety of ways known to ordinarily skilled artisans, e.g., by administering various amounts of a particular agent to an animal afflicted with a particular condition and then determining the relative therapeutic benefit received by the animal. Said amounts generally range from about 0.001 mg per kg of the body weight of the subject being treated to about 1000 mg per kg, and more typically, from about 0.1 to about 200 mg per kg. These amounts can be administered according to any dosing regimen acceptable to ordinarily skilled artisans supervising the treatment.

"Pharmaceutically acceptable carriers" are media generally accepted in the art for the administration of therapeutic compounds to humans. Such carriers are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., Remington's Pharmaceutical Sciences, $17^{th}$ ed., Mack Publishing Company, Easton, Pa., 1985, the contents of which are incorporated herein by reference.

Compounds of this invention are administered, for example, parenterally in various aqueous media such as aqueous dextrose and saline solutions; glycol solutions are also useful carriers. Solutions for parenteral administration preferably contain a water soluble salt of the active ingredient, suitable stabilizing agents, and if necessary, buffer substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or proply-paraben, and chlorobutanol.

Alternatively, the compounds are administered orally in solid dosage forms, such as capsules, tablets and powders; or in liquid forms such as elixirs, syrups, and/or suspensions. Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products, to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Compounds of this invention provide a particularly beneficial therapeutic index relative to other compounds available for the treatment of similar disorders. Without intending to be limited by theory, it is believed that this is due, at least in part, to the compounds' ability to be selective for the norepinephrine transporter protein (NET) over the other neurotransmitter transporters. Binding affinities are demonstrated by a number of means well known to ordinarily skilled artisans, including, without limitation, those described in the Examples section herein below.

Briefly, for example, protein-containing extracts from cells, e.g., HEK293 cells, expressing the transporter proteins are incubated with radiolabelled ligands for the proteins. The binding of the radioligands to the proteins is reversible in the presence of other protein ligands, e.g., the compounds of this invention; said reversibility, as described below, provides a means of measuring the compounds' binding affinities for the proteins (Ki). A higher Ki value for a compound is indicative that the compound has less binding affinity for a protein than is so for a compound with a lower Ki; conversely, lower Ki values are indicative of greater binding affinities.

Accordingly, a lower Ki for the protein for which the compound is more selective, and a higher Ki for the protein for which the compound is less selective indicate the difference in compound selectivity for proteins. Thus, the higher the ratio in Ki values of a compound for protein A over protein B, the greater is the compounds' selectivity for the latter over the former (the former having a higher Ki and the latter a lower Ki for that compound). Compounds provided herein induce fewer side effects during therapeutic usage because of their selectivity for the norepinephrine transporter protein, as indicated by the ratios of their Ki's for binding to NET over those for binding to other transporter proteins, e.g., the dopamine transporter (DAT) and the serotonin transporter (SERT). Generally, the compounds of this invention have a Ki ratio for DAT/NET of about $\geq 2:1$; the compounds generally also have a SERT/NET ratio of about $\geq 5:1$.

Moreover, in vivo assessment of the activity of compounds at the NE and DA transporters is, for example, by determining their ability to prevent the sedative effects of tetrabenazine (TBZ) (see, e.g., G. Stille, Arzn. Forsch. 1964, 14, 534-537; the contents of which are incorporated herein by reference). Randomized and coded doses of test compounds are administered to mice, as is then a dose of tetrabenazine. Animals are then evaluated for antagonism of tetrabenazine-induced exploratory loss and ptosis at specified time intervals after drug administration. Exploratory activity is, for example, evaluated by placing the animal in the center of a circle and then evaluating the amount of time it takes for the animal to intersect the circle's perimeter—generally, the longer it takes for the animal to make this intersection, the greater is its loss of exploratory activity. Furthermore, an animal is considered to have ptosis if its eyelids are at least 50% closed. Greater than 95% of the control (vehicle-treated) mice are expected to exhibit exploratory loss and ptosis; compound-related activity is then calculated as the percentage of mice failing to respond to the tetrabenazine challenge dose, with therapeutically more effective compounds expected to be better at reducing loss of exploratory behavior and ptosis.

Accordingly, the pharmaceutical compositions provided herein are useful in the treatment of subjects afflicted with various neurological and psychiatric disorders by administering to said subjects a dose of a pharmaceutical composition provided herein. Said disorders include, without limitation, attention deficit-hyperactivity disorder, anxiety, depression, post-traumatic stress disorder, supranuclear palsy, feeding disorders, obsessive compulsive disorder, analgesia, smoking cessation, panic attacks, Parkinson's and phobia. The compounds provided herein are particularly useful in the treatment of these and other disorders due, at least in part, to their ability to selectively bind to the transporter proteins for certain neurochemicals with a greater affinity than to the transporter proteins for other neurochemicals.

Synthesis

The compounds of the present invention can be prepared using the methods described below, together with methods known in the art of synthetic organic chemistry, or variations thereof as appreciated by those skilled in the art. Preferred methods include, but are not limited to, those methods described below.

The novel tetrahydroisoquinoline reuptake inhibitors of Formulae (I-IIIB) of this invention can be prepared by the general scheme outlined below (Schemes 1-4). The $R^1$-substituted N-benzyl amines of Formula (V) of Scheme 1, may be purchased from commercial sources, or alternatively, obtained from a simple reductive amination protocol. Thus, carbonyl containing compounds of Formula (IV) may be treated with $H_2N-R^1$ in lower alkyl alcoholic solvents (preferably methanol or ethanol) at temperatures at or below room temperature. The resulting imine may be reduced most commonly with alkaline earth borohydrides (preferably sodium borohydride) to provide the desired amine intermediates and the reductions are optimally conducted at or below room temperature.

Treatment of benzyl amine intermediates of Formula (V) with the electrophile intermediates of Formula (VII) generates the alkylation products of Formula (VIII). The alkylation reactions may be run under a wide variety of conditions familiar to one skilled in the art of organic synthesis. Typical solvents include acetonitrile, toluene, diethyl ether, tetrahydrofuran, dimethylsulfoxide, dimethylformamide, methylene chloride, and lower alkyl alcohols including ethanol. The reactions may be conducted at temperatures ranging from 0° C. up to the boiling point of the solvent employed. Reaction progress is conventionally monitored by standard chromatographic and spectroscopic methods. The alkylation reaction is optionally run with the addition of a non-nucleophilic organic base such as, but not limited to, pyridine, triethylamine and diisopropyl ethylamine, and reaction times may vary from 1 hour to several days to complete.

The aforementioned electrophilic intermediate of Formula (VII) is conveniently purchased from commercial sources or prepared via treatment of an optionally substituted acetophenone of Formula (VI) with common brominating agents such as, but not limited to, bromine, NBS, or tetrabutylammonium tribromide which readily affords the desired bromoacetophenones of Formula (VII). These reactions are optimally conducted in acetic acid or methylene chloride with methanol used as a co-solvent for the tribromide reagent with reaction temperatures at or below room temperature. Another embodiment of this methodology would include the use of chloroacetophenone compounds of Formula (VII).

The acetophenones of Formula (VI) are also in turn available from commercial sources or are conveniently obtained via several well known methods, including the treatment of the corresponding benzoic acid intermediates with two stoichiometric equivalents of methyllithium (see, e.g., Jorgenson, M. J. (Organic Reactions, 1970, 18, pg. 1)). Alternatively, one may treat the corresponding benzaldehydes with an alkyl-Grignard (for example, MeMgBr) or alkyl-lithium (for example, MeLi) nucleophile followed by routine oxidation to the ketone (see, e.g., Larock, R. C. (Comprehensive Organic Transformations, VCH Publishers, New York, 1989, p. 604)).

Reductions of compounds of Formula (VIII) to the benzyl alcohols of Formula (IX) proceeds with many reducing agents including, for example, sodium borohydride, lithium borohydride, borane, diisobutylaluminum hydride, and lithium aluminum hydride. The reductions are carried out for a period of time between 1 hour to 3 days at room temperature or elevated temperature up to the reflux point of the solvent employed. If borane is used, it may be employed as a complex for example, but not limited to, borane-methyl sulfide complex, borane-piperidine complex, or borane-tetrahydrofuran complex. One skilled in the art will understand the optimal combination of reducing agents and reaction conditions needed or may seek guidance from the text of Larock, R. C. (see above).

Compounds of Formula (IX) may be cyclized to the tetrahydroisoquinoline compounds of Formula (Ib) wherein $R^7$=H of this invention by brief treatment with a strong acid. Suitable acids include, but are not limited to, concentrated sulfuric acid, polyphosphoric acid, methanesulfonic acid and trifluoroacetic acid. The reactions are run neat or in the optional presence of a co-solvent such as, for example, methylene chloride or 1,2-dichloroethane. The cyclizations may be conducted at temperatures ranging from 0° C. up to the reflux point of the solvent employed. One skilled in the art of heterocyclic chemistry will readily understand these conditions or may consult the teachings of Mondeshka, et al. (Il Farmaco, 1994, 49, 475-480) or Venkov, et al. (Synthesis, 1990, 253-255). Cyclizations may also be effected by treatment of compounds of Formula (IX) with strong Lewis acids, such as for example, aluminum trichloride typically in halogenated solvents such as methylene chloride. One skilled in the art will be familiar with the precedent taught by Kaiser, et al. (J. Med. Chem., 1984, 27, 28-35) and Wyrick, et al. (J. Med. Chem., 1981, 24, 1013-1015).

Compounds of Formulae (I-III) may be obtained in enantiomerically pure (R) and (S) form by crystallization with chiral salts as well known to one skilled in the art, or alternatively, may be isolated through chiral HPLC employing commercially available chiral columns.

Compounds of Formulae (I-III) wherein $R^7$=OH in Schemes 1, 3 and 4 of this invention may be prepared according to the teaching of Kihara, et al. (Tetrahedron, 1992, 48, 67-78), and Blomberg, et al. (Synthesis, 1977, p. 18-30). Thus ketone compounds of Formula (VIII) which possess an ortho-iodide on the aromatic ring undergoing cyclization may be treated with strong bases, such as, but not limited to, lower alkyl ($C_{1-6}$) lithium bases (preferably t-BuLi or n-BuLi) to afford the anticipated halogen-metal exchange followed by intramolecular Barbier cyclization to generate compounds of Formulae (I-III) wherein $R^7$=OH. Inert solvents such as dialkyl ethers (preferably diethyl ether), cyclic ethers (preferably tetrahydrofuran or 1,4-dioxane), etc. are necessary, and reaction temperatures are kept low (−78° C. to −25° C.) to avoid by-products. Alternatively, halogen-metal exchange may also be effected in the presence of zerovalent nickel, in which case N,N-dialkylformamides (preferably dimethylformamide) serve as ideal solvents. This cyclization is best performed when X=Br to avoid over-reduction or intermolecular reactivity. Additionally, compounds of Formulae (I-III) wherein $R^7$=OH may be readily alkylated (vide supra) to afford compounds Formulae (I-III) wherein $R^7$=$OR^{10}$. Finally, further treatment of compounds of Formulae (I-III) wherein $R^7$=OH with a halogenating reagent or specifically a fluorinating reagent such as, but not limited to diethylaminosulfur trifluoride (DAST), readily provides compounds of Formulae (I-III) wherein $R^7$=F. Further reference may be gained from the review of Hudlicky (Organic Reactions, 1985, 35, p. 513-637).

In reference to precursor compounds of Formula (IV), for those reagents that may be commercially unavailable, numerous synthetic routes from other commercial compounds or compounds known in the art exist and these will be readily evident to anyone skilled in the art of organic synthesis. Without limitation, a representative method is shown in Scheme 2, wherein the allyl alcohol of Formula (X) is subjected to ready ozonolysis followed by reductive workup with reagents, such as, but not limited to, dimethyl sulfide to afford a lactol which is treated with mild acid under a wide range of conditions to afford benzofuran of Formula (XI). Methodology for functional group interconversion of the ester to aldehyde will be readily apparent to a skilled artisan to provide those targets of Formula (IV).

Furthermore, pre-cyclization amino alcohols Formula (XII) of Scheme 3 and Formulae (XIII-XIV) of Scheme 4 are synthesized in completely analagous manner to those methods described hereinabove for the preparation of pre-cyclization amino alcohol of Formula (IX) of Scheme 1. Also as described above, the pre-cyclization amino alcohols of Formula (XII) of Scheme 3 and Formulae (XIII-XIV) of Scheme 4 may be cyclized as described to afford the target tetrahydroisoquinolines of Formula (Ia) of Scheme 3 and Formulae (IIa, IIb, IIIa and IIIb) of Scheme 4. It will be readily understood by anyone skilled in the art that regiomeric tetrahydroisoquinolines are afforded upon the cyclization of compounds of Formulae (XIII-XIV).

In a further embodiment of this invention the unsaturated furan, indole, and thiophene tetrahydroisoquinolines of Formulae (I-III) may be partially reduced to the corresponding dihydrofuran, dihydroindole, and dihydrothiophene tetrahydroisoquinolines of Formulae (I-III). Reductions are conducted in the presence of hydrogen, either at atmospheric pressure or at elevated pressure and in a wide range of solvents, such as, but not limited to, methanol, ethanol, and ethyl acetate. The reactions are optimally conducted in the presence of a metal catalyst, such as, but not limited to, palladium, platinum, or rhodium. Optimal conditions for hydrogenation will be readily understood by the skilled artisan; alternatively, one may consult the text of Larock, R. C. (Comprehensive Organic Transformations, VCH Publishers, New York, 1989, p. 6.

In cases where partial reduction of the above mentioned heterocycles is not possible (on compound Ib wherein $R^7$=H) due to concomitant hydrogenolysis of pendant aryl substituents (eg. Cl), it is necessary to reduce the heterocyclic moiety (i.e. benzofuran, indole or thiophene) at an earlier stage (Scheme 1, intermediate (V)) in the synthesis and then introduce the pendant aryl (VII) by the same methods outlined in Scheme 1.

The contents of the above-cited disclosures are incorporated herein by reference.

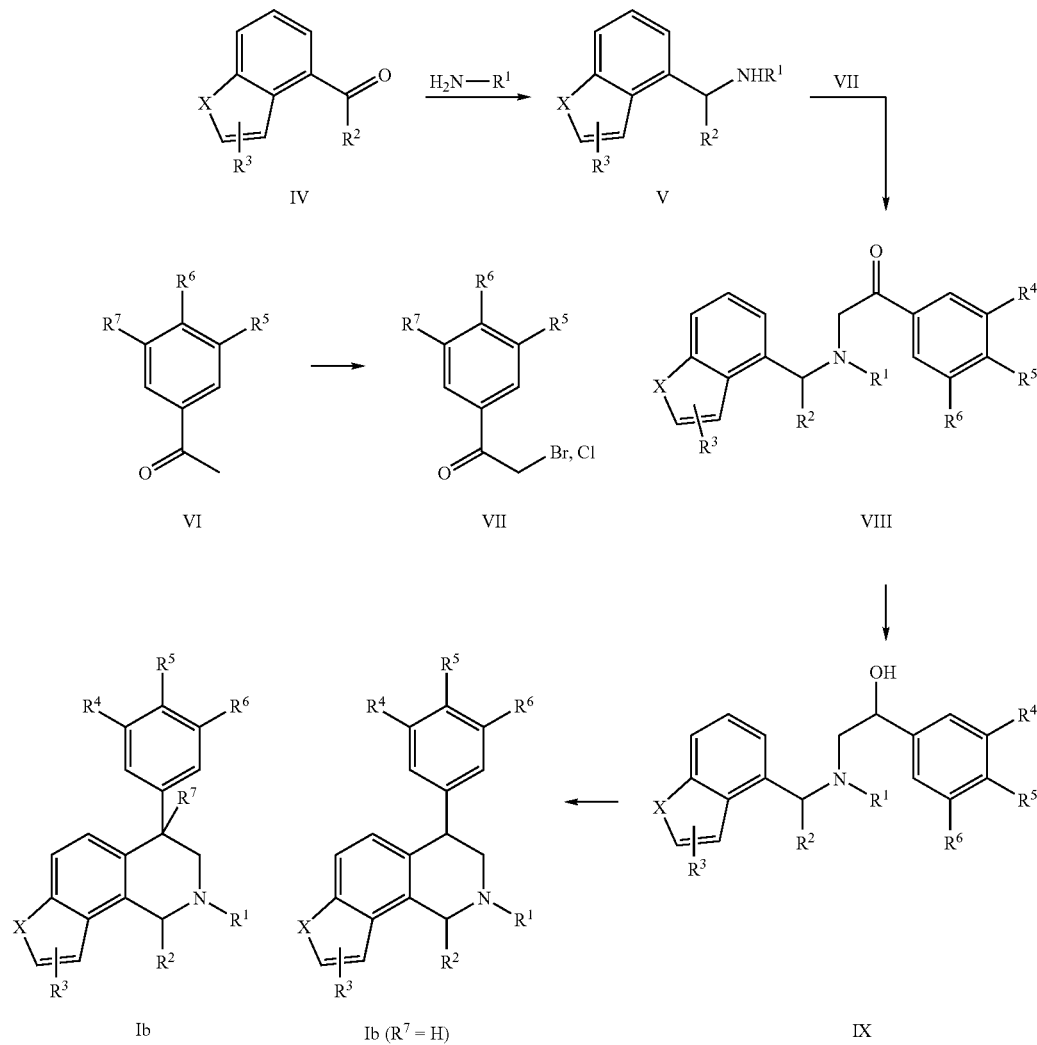

SCHEME 1

SCHEME 2
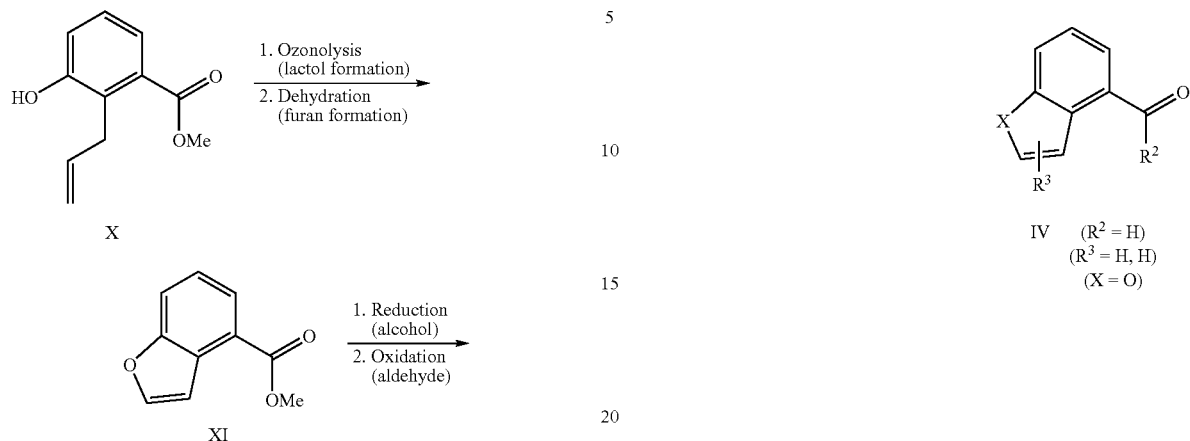
SCHEME 3
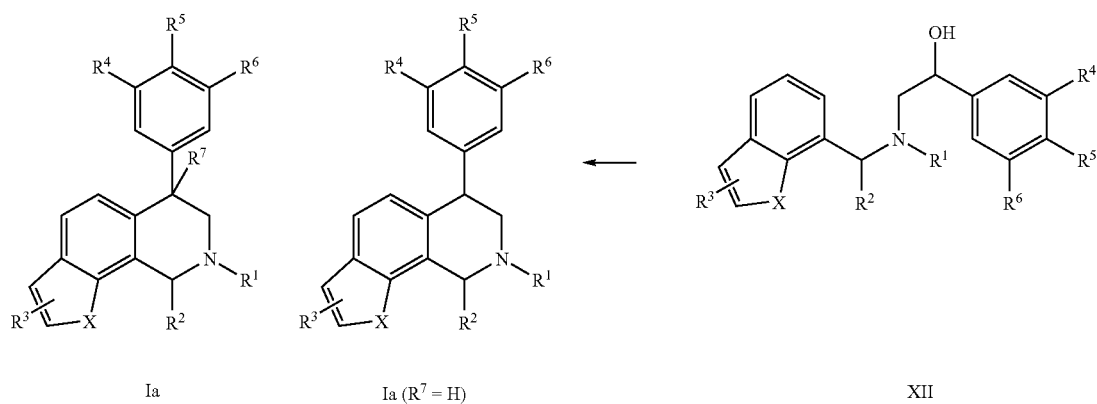
SCHEME 4
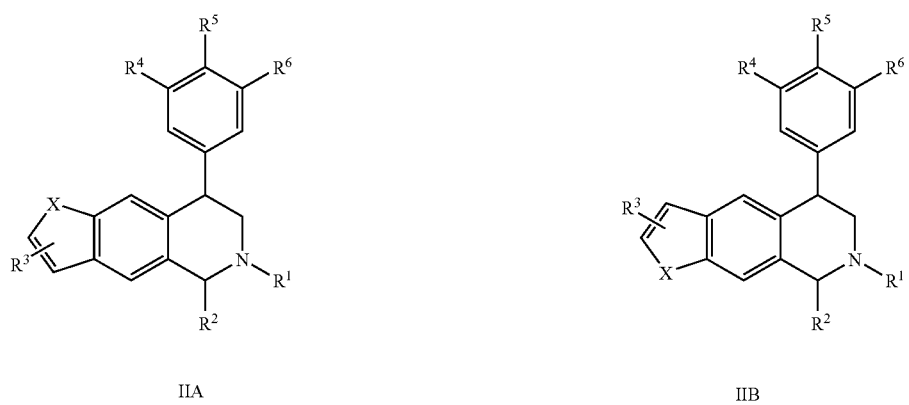

-continued

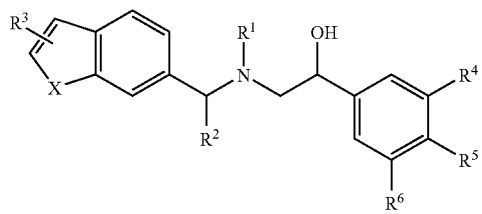

XIII

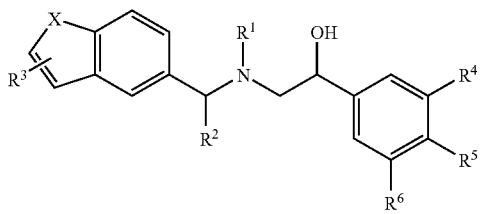

XIV

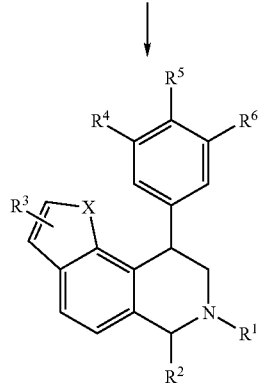

IIIA

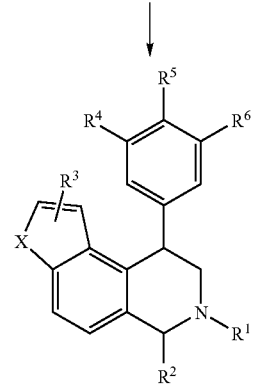

IIIB

This invention will be better understood by reference to the following Examples section. However, those of ordinary skill in the art will readily appreciate that the examples are merely illustrative of the invention as defined in the claims, which follow thereafter.

EXAMPLES

Compounds listed in Tables I-VIA below (Examples 1-131) were made according to the synthetic schemes set forth hereinabove, and have the melting points as set forth in the Tables; where a compound is an oil or a solid, it is listed as such therein and if it is a solid, the salt form is indicated.

TABLE I

| Ex. | Ring | $R^4$ | $R^5$ | $R^6$ | MP (° C.) | Salt |
|---|---|---|---|---|---|---|
| 1 | unsat. | H | H | H | 165-168 | maleate |
| 2 | sat. | H | H | H | 81-83 | |
| 3 | unsat. | H | Me | H | 240-246 | hydrochloride |
| 4 | sat. | H | Me | H | 190-191 | maleate |
| 5 | unsat. | H | Cl | H | Oil, MS | |
| 6 | sat. | Cl | H | H | Oil, MS | |
| 7 | unsat. | H | F | H | 242-257 | hydrochloride |
| 8 | sat. | H | F | H | Oil, MS | |
| 9 | unsat. | F | H | F | 233-236 | hydrochloride |

TABLE IB enantiomerically pure compounds (based on general structure in Table I)

| Ex. | Ring | R⁴ | R⁵ | R⁶ | MP (° C.) | Salt/Isomer |
|---|---|---|---|---|---|---|
| 10 | sat. | H | H | H | — | enantiomer A |
| 11 | sat. | H | H | H | 121 | enantiomer B |

TABLE II

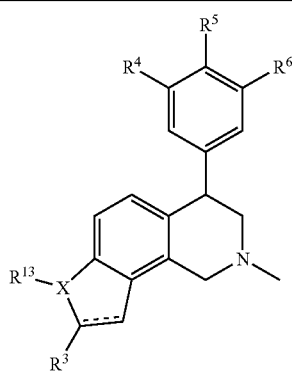

| Ex. | X | Ring | R³ | R⁴ | R⁵ | R⁶ | R¹³ | MP (° C.) | Salt |
|---|---|---|---|---|---|---|---|---|---|
| 12 | O | unsat. | H | H | H | H | — | 199-204 | maleate |
| 13 | O | sat. | H | H | H | H | — | 168-169 | maleate |
| 14 | O | unsat. | H | F | F | H | — | 240-243 | hydrochloride |
| 15 | O | sat. | H | F | F | H | — | 86-90 | |
| 16 | O | unsat. | H | F | H | F | — | 256-258 | hydrochloride |
| 17 | O | sat. | H | F | H | F | — | 107-109 | |
| 18 | O | unsat. | H | F | H | H | — | 156-160 | fumarate |
| 19 | O | sat. | H | F | H | F | — | 224-226 | hydrochloride |
| 20 | O | unsat. | H | H | F | H | — | 190-192 | hydrochloride |
| 21 | O | sat. | H | H | F | H | — | 110-116 | |
| 22 | O | unsat. | H | Cl | H | H | — | Oil, MS | |
| 23 | O | sat. | H | Cl | H | H | — | 78-80 | |
| 24 | O | unsat. | H | H | Cl | H | — | 230-234 | hydrochloride |
| 25 | O | sat. | H | H | Cl | H | — | 148-150 | |
| 26 | O | unsat. | H | H | Cl | F | — | 253-259 | hydrochloride |
| 27 | O | sat. | H | H | Cl | F | — | 97-98 | |
| 28 | O | unsat. | H | H | F | Cl | — | 250-258 | hydrochloride |
| 29 | O | sat. | H | H | F | Cl | — | 235-242 | hydrochloride |
| 30 | O | unsat. | H | F | H | Cl | — | 279-284 | hydrochloride |
| 31 | O | sat. | H | F | H | Cl | — | 253-261 | hydrochloride |
| 32 | O | unsat. | H | H | OMe | H | — | 212-214 | hydrochloride |
| 33 | O | sat. | H | H | OMe | H | | — | 119-121 |
| 34 | O | unsat. | Me | H | H | H | — | 187-192 | maleate |
| 35 | O | unsat. | Et | H | H | H | — | 154-160 | maleate |
| 36 | O | unsat. | CH₂OH | H | H | H | — | 149-162 | hydrochloride |
| 37 | S | unsat. | H | H | H | H | — | 218-220 | hydrochloride |
| 38 | N | unsat. | H | H | H | H | H | 142-144 | |
| 39 | N | unsat. | H | H | H | H | Me | 106-108 | |
| 40 | N | unsat. | H | H | H | H | Et | Amorphous, MS | |
| 41 | N | unsat. | H | H | H | H | Bn | Amorphous, MS | |
| 42 | N | sat. | H | H | H | H | H | 84-86 | |
| 43 | N | sat. | H | H | H | H | Me | 88-90 | |
| 44 | N | sat. | H | H | H | H | Et | 91-93 | |
| 45 | N | unsat. | H | H | F | F | H | 164-169 | |
| 46 | N | unsat. | H | H | F | F | Me | Oil, MS | |
| 47 | N | sat. | H | H | F | F | H | 45-51 | |
| 48 | N | sat. | H | H | F | F | Me | Oil, MS | |
| 49 | N | unsat. | H | F | H | F | Me | 110-112 | |
| 50 | N | sat. | H | F | H | F | H | 71-75 | |
| 51 | N | sat. | H | F | H | F | Me | Amorphous, MS | |
| 52 | N | unsat. | H | Cl | H | H | H | 184-186 | |
| 53 | N | unsat. | H | Cl | H | H | Me | 90-92 | |
| 54 | N | sat. | H | Cl | H | H | H | 236-238 | dihydrochloride |
| 55 | N | sat. | H | Cl | H | H | Me | 63-65 | |
| 56 | N | unsat. | H | F | H | H | H | 150-152 | |

TABLE II-continued

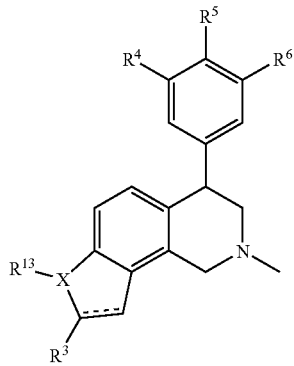

| Ex. | X | Ring | $R^3$ | $R^4$ | $R^5$ | $R^6$ | $R^{13}$ | MP (° C.) | Salt |
|---|---|---|---|---|---|---|---|---|---|
| 57 | N | unsat. | H | F | H | H | Me | 255-258 | hydrochloride |
| 58 | N | sat. | H | F | H | H | H | 210-214 | dihydrochloride |
| 59 | N | unsat. | H | H | F | H | H | 200-205 | hydrochloride |
| 60 | N | sat. | H | H | F | H | H | Oil, MS | |
| 61 | N | unsat. | H | F | Cl | H | H | 149-153 | |
| 62 | N | unsat. | H | F | Cl | H | Me | 120-124 | |
| 63 | N | sat. | H | F | Cl | H | H | Amorphous, MS | |
| 64 | N | sat. | H | F | Cl | H | Me | Oil, MS | |
| 65 | N | unsat. | H | Cl | F | H | H | 189-195 | |
| 66 | N | unsat. | H | Cl | F | H | Me | 212-215 | hydrochloride |
| 67 | N | sat. | H | Cl | F | H | H | 200-243 | dihydrochloride |
| 68 | N | sat. | H | Cl | F | H | Me | 194-200 | dihydrochloride |

TABLE IIA (identical general structure as shown in Table II)

| Ex. | X | Ring | $R^3$ | $R^4$ | $R^5$ | $R^6$ | $R^{13}$ | MP (° C.) | Salt |
|---|---|---|---|---|---|---|---|---|---|
| 69 | O | sat. | H | F | H | H | — | 156–160 | fumarate |

TABLE IIB enantiomerically pure compounds (based on general structure shown in Table II but with (R)— or (S)— absolute configuration)

| Ex. | X | Ring | $R^3$ | $R^4$ | $R^5$ | $R^6$ | $R^{13}$ | MP (° C.) | Miscellaneous* |
|---|---|---|---|---|---|---|---|---|---|
| 70 | O | unsat. | H | H | H | H | — | 172–174.5 | enantiomer B, fumarate |
| 71 | O | sat. | H | H | H | H | — | — | enantiomer A, maleate |
| 72 | O | sat. | H | H | H | H | — | — | enantiomer B, maleate |
| 73 | O | unsat. | H | H | F | H | — | 105–107 | rotation −55.6° (C = 0.200, MeOH) |
| 74 | O | unsat. | H | H | F | H | — | 104–105 | rotation +53.9° (C = 0.200, MeOH) |
| 75 | O | unsat. | H | F | F | H | — | 124.5–125.5 | maleate, enantiomer B, rotation +18.2° (C = 0.262, MeOH) |
| 76 | O | unsat. | H | H | Cl | H | — | 87–89 | enantiomer A |
| 77 | O | unsat. | H | H | Cl | H | — | 87–89 | enantiomer B |
| 78 | O | unsat. | H | F | H | F | — | 159.5–161.0 | maleate, enantiomer B |
| 79 | N | unsat. | H | H | H | H | H | 115.5–117.0 | enantiomer A, rotation −55.2° (C = 0.372, MeOH) |
| 80 | N | unsat. | H | H | H | H | H | 116.0–117.5 | enantiomer B, rotation +55.5 (C = 0.384, MeOH) |

*Miscellaneous-enantiomer A indicates the first stereoisomer eluted from chiral reverse phase HPLC column (commercial columns used); enantiomer B indicates second compound eluted.

TABLE III

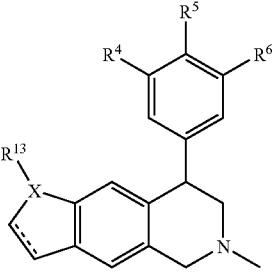

| Ex. | X | Ring | $R^4$ | $R^5$ | $R^6$ | $R^{13}$ | MP (° C.) | Salt |
|---|---|---|---|---|---|---|---|---|
| 81 | O | unsat. | H | H | H | — | 241-246 | hydrochloride |
| 82 | O | sat | H | H | H | — | 301-307 | hydrochloride |
| 83 | O | unsat. | H | H | H | — | 117-122 | |
| 84 | O | unsat. | H | H | H | — | 257-269 | hydrochloride |
| 85 | N | unsat. | H | H | H | H | 95-103 | |

TABLE IIIA (identical general structure as shown in Table III)

| Ex. | X | Ring | R⁴ | R⁵ | R⁶ | R¹³ | MP (° C.) | Salt |
|---|---|---|---|---|---|---|---|---|
| 86 | O | unsat. | H | F | F | — | 257–269 | hydrochloride |
| 87 | O | unsat. | H | F | H | — | 117–122 | |
| 88 | O | sat. | H | F | H | — | 303–308 | hydrochloride |
| 89 | O | sat. | H | F | F | — | 296–302 | hydrochloride |

TABLE IV

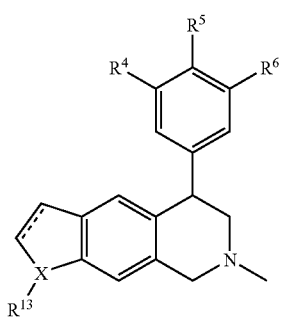

| Ex. | X | Ring | R⁴ | R⁵ | R⁶ | R¹³ | MP (° C.) | Salt |
|---|---|---|---|---|---|---|---|---|
| 90 | O | unsat. | H | H | H | — | 222-232 | hydrochloride |
| 91 | O | sat. | H | H | H | — | 90-95 | |
| 92 | O | unsat. | H | F | F | — | 263-267 | hydrochloride |
| 93 | O | sat. | H | F | F | — | 258-265 | hydrochloride |
| 94 | O | unsat. | H | F | H | — | 222-235 | hydrochloride |
| 95 | O | sat. | H | F | H | — | 258-266 | hydrochloride |
| 96 | O | unsat. | H | H | Cl | — | 229-234 | hydrochloride |
| 97 | O | sat. | H | H | Cl | — | 225-243 | hydrochloride |
| 98 | O | unsat. | H | Cl | F | — | 263-271 | hydrochloride |
| 99 | O | sat. | H | Cl | F | — | 253-256 | hydrochloride |
| 100 | O | sat. | H | F | Cl | — | 268-75 | hydrochloride |
| 101 | O | unsat. | H | OMe | H | — | 233-238 | hydrochloride |
| 102 | O | sat. | H | OMe | H | — | 279-284 | hydrochloride |
| 103 | N | unsat. | H | H | H | H | 200-202 | |
| 104 | N | unsat | H | Bn | H | H | Amorphous, MS | |

TABLE IVA (identical general structure as shown in Table IV)

| Ex. | X | Ring | R⁴ | R⁵ | R⁶ | R¹³ | MP (° C.) | Salt |
|---|---|---|---|---|---|---|---|---|
| 105 | O | unsat. | H | F | Cl | — | 248–254 | hydrochloride |

TABLE IVB enantiomerically pure compounds (based on general structure in Table IV)

| Ex. | X | Ring | R⁴ | R⁵ | R⁶ | R¹³ | MP (° C.) | Salt |
|---|---|---|---|---|---|---|---|---|
| 106 | O | unsat. | H | H | H | — | — | maleate, enantiomer A |
| 107 | O | unsat. | H | H | H | — | — | maleate, enantiomer B |

TABLE V

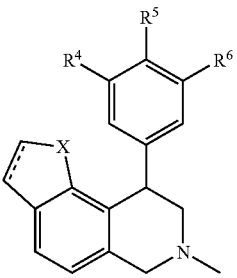

| Ex. | X | Ring | R⁴ | R⁵ | R⁶ | MP (° C.) | Salt |
|---|---|---|---|---|---|---|---|
| 108 | O | unsat. | H | H | H | 250-271 | hydrochloride |
| 109 | O | sat. | H | H | H | 89-95 | |
| 110 | O | unsat. | H | F | H | 262-278 | hydrochloride |
| 111 | O | sat. | H | F | H | 139-142 | |
| 112 | O | unsat. | H | F | Cl | 288-294 | hydrochloride |
| 113 | O | sat. | H | F | Cl | 255-278 | hydrochloride |
| 114 | O | unsat. | H | Cl | F | 268-275 | hydrochloride |
| 115 | O | sat. | H | Cl | F | 257-262 | hydrochloride |
| 116 | O | unsat. | H | H | Cl | 252-275 | hydrochloride |
| 117 | O | sat. | H | H | Cl | 249-254 | hydrochloride |
| 118 | O | unsat. | H | OMe | H | 260-267 | hydrochloride |
| 119 | O | sat. | H | OMe | H | 246-264 | hydrochloride |
| 120 | O | unsat. | H | F | F | 276-283 | hydrochloride |
| 121 | O | sat. | H | F | F | 255-272 | hydrochloride |
| 122 | S | unsat. | H | H | H | 232-234 | hydrochloride |

TABLE VI

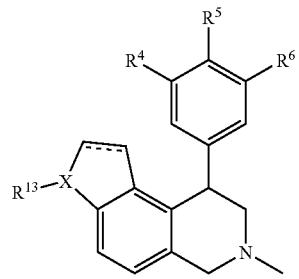

| Ex. | X | Ring | R⁴ | R⁵ | R⁶ | R¹³ | MP (° C.) | Salt |
|---|---|---|---|---|---|---|---|---|
| 123 | O | unsat. | H | H | H | — | 234-240 | hydrochloride |
| 124 | O | sat. | H | H | H | — | 78-82 | |
| 125 | O | unsat. | H | F | H | — | 249-254 | hydrochloride |
| 126 | O | sat. | H | F | H | — | 226-229 | hydrochloride |
| 127 | O | unsat. | H | F | F | — | 252-261 | hydrochloride |
| 128 | O | sat. | H | F | F | — | Amorphous, MS | |

TABLE VIA (identical general structure as shown in Table VI)

| Ex. | X | Ring | R⁴ | R⁵ | R⁶ | R¹³ | MP (° C.) | Salt |
|---|---|---|---|---|---|---|---|---|
| 129 | N | unsat. | H | H | H | H | 205-240 | |
| 130 | N | sat. | H | H | H | H | 271-285 | dihydrochloride |
| 131 | N | unsat. | H | H | H | Me | — | hydrochloride |

Example 5

Step A: Benzofuran-7-carboxaldehyde (4.44 g, 30.4 mmol), aqueous methylamine (5.5 mL, 63 mmol) and MeOH (35 mL) were combined in a 25-mL flask under N₂.

The mixture was cooled to 0° C. under rapid stirring, and NaBH$_4$ (0.61 g, 16 mmol) was added in portions over 5 min. The mixture warmed to room temperature while stirring overnight. The mixture was diluted with water (50 mL), stirred for 15 min, and extracted (3×) with CH$_2$Cl$_2$. The combined organic extracts were washed (3×) with 2 N HCl. These acidic extracts were made basic with solid KOH, additional water, and conc. NH$_4$OH. The basic mixture was extracted (3×) with CH$_2$Cl$_2$. This second set of organic extracts were combined and dried over Na$_2$SO$_4$, filtered, and concentrated in vacuo to provide the methyl amine product (3.51 g, 71%) as a yellow oil: $^1$H NMR(500 MHz, CDCl$_3$) δ 7.66 (d, J=2.3 Hz, 1 H), 7.53-7.55 (m, 1 H), 7.22-7.29 (m, 2 H), 6.80 (d, J=2.4 Hz, 1 H), 4.10 (s, 2 H), 2.51 (s, 3 H).

Step B: Methyl amine product from Step A (3.50 g, 21.7 mmol ) and 4' chlorophenacyl bromide (6.2 g, 23 mmol ) were dissolved in CH$_2$Cl$_2$ (45 mL) in a 250-mL flask under N$_2$. The mixture was stirred rapidly, Et$_3$N (3.0 mL, 22 mmol) was added, and the mixture continued stirring overnight. The mixture was diluted with water, the layers were separated, and the aqueous layer was extracted twice with CH$_2$Cl$_2$. The combined organic extracts were dried over Na$_2$SO$_4$, filtered, and concentrated in vacuo. The crude residue was purified by silica gel chromatography (20% EtOAc/hexanes) to provide amino ketone (4.28 g, 63%) as a yellow oil: $^1$H NMR (300 MHz, CDCl$_3$) δ 7.94-7.96 (m, 1 H), 7.76-7.80 (m, 1 H), 7.60 (d, J=2.3 Hz, 1 H), 7.47-7.56 (m, 2 H), 7.18-7.35 (m, 3 H), 6.77 (d, J=2.3 Hz, 1 H), 4.03 (s, 2 H), 3.79 (s, 2 H), 2.42 (s, 3 H).

Step C: The amino ketone from Step B (4.28 g, 13.6 mmol) was dissolved in MeOH (30 mL) under N$_2$. The mixture was cooled to 0° C. , NaBH$_4$ (1.07 g, 28.2 mmol ) was added in portions, and the mixture was stirred for 5 h while warming to room temperature. The mixture was diluted with water and extracted (3×) with CH$_2$Cl$_2$. The combined organic extracts were dried over Na$_2$SO$_4$, filtered, and concentrated in vacuo. The crude residue was purified by silica gel chromatography (20% EtOAc/hexanes) to provide the amino alcohol (3.14 g, 73%) as a yellow oil: $^1$H NNR (500 MHz, CDCl$_3$) δ 7.61-7.69 (m, 1 H), 7.53-7.56 (m, 1 H), 7.32-7.40 (m, 1 H), 7.18-7.29 (m, 5 H), 6.78-6.83 (m, 1 H), 4.75-4.81 (m, 1 H), 4.35 (br s, 1 H), 4.35 (br s, 1 H), 4.06 (d, J=13.2 Hz, 1 H), 3.87 (d, J=13.2 Hz, 1 H), 2.55-2.66 (m, 1 H), 2.34 (s, 3 H).

Step D: The amino alcohol from Step C (580 mg, 1.83 mmol) was dissolved in CH$_2$Cl$_2$ (18 mL) in a 100-mL flask fitted with a condenser under N$_2$. The mixture was cooled to 0° C. while stirring, and MeSO$_3$H (6.0 mL, 92 mmol) was added dropwise. The mixture was allowed to warm to room temperature, then warmed to reflux overnight. The mixture was cooled to room temperature, 2 N NaOH and water were slowly added to make the mixture basic. The mixture was extracted (3×) with CH$_2$Cl$_2$, and the combined organic extracts were dried over Na$_2$SO$_4$, filtered, and concentrated in vacuo. The crude residue was purified by silica gel chromatography (5% EtOAc/hexanes containing 1% Et$_3$N) to provide compound, Example 5 (304 mg, 56%) as a pale yellow oil: $^1$H NMR (300 MHz, CDCl$_3$) δ 7.61 (d, J=2.1 Hz, 1 H), 7.32 (d, J=8.1 Hz, 1 H), 7.19-7.22 (m, 3 H), 7.07-7.11 (m, 1 H), 6.72-6.77 (m, 2 H), 4.34 (t, J=6.2 Hz, 1 H), 4.03 (d, J=15.5 Hz, 1 H), 3.87 (d, J=15.3 Hz, 1 H), 3.01-3.08, m, 1 H), 2.66 (dd, J=7.8, 11.5 Hz, 1 H), 2.50 (s, 3 H); CI MS m/z=298 [C$_{18}$H$_{16}$ClNO+H]$^+$ Anal. Calcd. for C$_{18}$H$_{16}$ClNO-0.25 H$_2$O: C, 71.52; H, 5.50; N, 4.63. Found: C, 71.53; H, 5.34; N, 4.42. Starting material (115 mg, 20%) was also recovered.

Example 6

Step A: The amine prepared in Example 5, Step A (1.24 g, 7.69 mmol) was dissolved in absolute EtOH (8 mL) in a Parr reactor. 10% Pd/C (0.61 g, 50% by weight) was added, and the mixture was hydrogenated at 30 psi overnight. The slurry was filtered through Celite, and the pad was washed twice with MeOH. The filtrate was concentrated in vacuo to provide dihydrobenzofuran 76 (1.27 g, quantitative) as a yellow oil: $^1$H NMR (300 MHz; CDCl$_3$) δ 7.07-7.13 (m, 2 H), 6.81 (t, J=7.4 Hz, 1 H), 4.58 (t, J=8.7 Hz, 1 H), 3.78 (s, 2 H), 3.18-3.27 (m, 3 H), 2.45 (s, 3 H).

Step B: The dihydrobenzofuran amine (1.27 g, 7.69 mmol, prepared in Step A), 3'-chlorophenacyl bromide 71 (1.9 g, 8.0 mmol), and CH$_2$Cl$_2$ (15 mL) were combined in a 100-mL flask under N$_2$. The mixture was rapidly stirred while Et$_3$N (1.1 mL, 7.9 mmol) was added. After stirring for 2 h, the mixture was diluted with water and CH$_2$Cl$_2$, and the layers were separated. The aqueous layer was extracted twice with CH$_2$Cl$_2$, and the combined organic extracts were dried over Na$_2$SO$_4$, filtered, and concentrated in vacuo. The crude residue was purified by silica gel chromatography (20% EtOAc/hexanes) to provide the product amino ketone (1.75 g, 72%) as a yellow oil: $^1$H NMR (300 NHz, CDCl$_3$) δ 7.96 (t, J=1.7 Hz, 1 H), 7.82-7.86 (m, 1 H), 7.50 (dt, J=1.4, 8.3 Hz, 1 H), 7.35 (t, J=7.9 Hz, 1 H), 7.10 (dd, J=7.5, 15.6 Hz, 2 H), 6.82 (t, J=7.4 Hz, 1 H), 4.51 (t, J=8.7 Hz, 2 H), 3.73 (s, 2 H), 3.69 (s, 2 H), 3.20 (t, J=8.7 Hz, 2 H), 2.37 (s, 3 H); CI MS m/z=316 [C$_{18}$H$_{18}$ClNO$_2$+H]$^+$.

Step C: The amino ketone that was prepared in Step B (1.75 g, 5.54 mmol) was dissolved in MeOH (12 mL) in a 100-mL flask under N$_2$. The mixture was cooled to 0° C., and NaBH$_4$ (440 mg, 11.6 mmol) was added in one portion. The mixture was allowed to warm to room temperature while stirring overnight. The mixture was diluted with water, then extracted (3×) with CH$_2$Cl$_2$. The combined organic extracts were dried over Na$_2$SO$_4$, filtered, and concentrated in vacuo to provide the product amino alcohol (1.76 g, 99%) as a yellow oil which solidified upon standing: $^1$H NMR (300 MHz, CDCl$_3$) δ 7.38 (s, 1 H), 7.23-7.36 (m, 3 H), 7.13-7.16 (m, 1 H), 7.01 (d, J=7.4 Hz, 1 H), 6.81 (t, J=7.4 Hz, 1 H), 4.73 (dd, J=4.1, 9.8 Hz, 1 H), 4.60 (t, J=9.0 Hz, 2 H), 3.75 (d, J=12.9 Hz, 1 H), 3.50 (d, J=12.9 Hz, 1 H), 3.23 (t, J=8.7 Hz, 2 H), 2.49-2.62 (m, 2 H), 2.30 (s, 3 H).

Step D: The amino alcohol, which was prepared in Step C, (814 mg, 2.56 mmol) was dissolved in CH$_2$Cl$_2$ (25 mL) in a 100-mL flask fitted with a condenser under N$_2$. The mixture was cooled to 0° C. while stirring rapidly, and MeSO$_3$H (8.4 mL, 129 mmol) was added dropwise. The mixture was allowed to warm to room temperature, then heated to reflux for 48 h. The mixture was cooled to room temperature and slowly quenched by the addition of 2 N NaOH. The layers were separated, and the aqueous layer was extracted (3×) with CH$_2$Cl$_2$. The combined organic extracts were dried over Na$_2$SO$_4$, filtered, and concentrated in vacuo. The crude residue was purified by silica gel chromatography (1.5% MeOH/CH$_2$Cl$_2$) to provide compound, Example 6 (603 mg, 75%) as a pale yellow oil: $^1$H NMR (300 MHz, CDCl$_3$) δ 7.17-7.22 (m, 3 H), 7.06-7.11 (m, 1 H), 6.93 (d, J=7.5 Hz, 1 H), 6.35 (d, J =7.5 Hz, 1 H), 4.57-4.64 (m, 2 H), 4.19 (t, J=6.2 Hz, 1 H), 3.69 (d, J=15.4 Hz, 1 H), 3.50 (d, J=15.3 Hz, 1 H), 3.18 (t, J=8.8 Hz, 2 H), 2.91-2.98 (m, 1 H), 2.56 (dd, J=8.0, 11.4 Hz, 1 H), 2.43 (s, 3 H); API MS m/z=300 [C$_{18}$H$_{18}$ClNO+H]$^+$; Anal. Calcd. for C$_{18}$H$_{18}$ClNO-0.6 H$_2$O: C, 69.60; H, 6.23; N, 4.51. Found: C, 69.53; H, 5.88; N, 4.38.

Example 12

Step A: Allyl alcohol X (2.0 g, 10.5 mmol) was dissolved in methanol (90 ml), cooled to −78° C. and ozonolyzed until no starting material remained (approximately 30 minutes). Dimethyl sulfide (4 ml) was added rapidly, and the resulting mixture was allowed to warm to room temperature overnight. The solvent was removed in vacuo and the residue was dissolved in diethyl ether, then washed twice with water and once with brine. The organic portion was dried over anhydrous sodium sulfate, filtered, and the solvent removed in vacuo to provide the desired lactol, 1.18 g (58%) as a viscous yellow oil: $^1$H NMR (300 MHz, CDCl$_3$) δ 7.56-7.59 (m, 1H), 7.21-7.26 (m, 1H), 7.03 (d, 1H, J=8.0 Hz), 6.12 (dd, 1H, J=2.2, 6.5 Hz), 3.90 (s, 3H), 3.40-3.60 (m, 2H).

Step B: The product from Step A (8.0 g, 41.0 mmol) was stirred in H$_3$PO$_4$ (85%, 50 ml) at room temperature for 30 minutes. The resulting cloudy mixture was diluted with water and extracted (4×) with diethyl ether. The combined organic extracts were washed with brine, dried over anhydrous sodium sulfate, filtered, and the solvent removed in vacuo. The crude material was purified by flash chromatography on silica gel (20:1 hexanes/ethyl acetate) to afford the benzofuran methyl ester 3.87 g (53%) as a light yellow oil: $^1$H NMR (300 MHz, CDCl$_3$) δ 7.99 (d, 1H, J=7.1 Hz), 7.68-7.74 (m, 2H), 7.32-7.38 (m, 2H), 3.99 (m, 3H); CI MS m/z=177 [C$_{10}$H$_8$O$_3$=H]$^+$.

Step C: The product from Step B (4.67 g, 27.0 mmol), dissolved in anhydrous tetrahydrofuran (60 ml), was added dropwise to a stirred suspension of lithium aluminum hydride (2.5 g, 65.0 mmol) in anhydrous tetrahydrofuran (50 ml) at 0° C. under nitrogen. The grey slurry was stirred and allowed to warm to room temperature over two hours. The mixture was cooled again to 0° C., then quenched with ethyl acetate until bubbling ceased, and a solution of saturated aqueous sodium sulfate was added until the grey color disappeared. Anhydrous sodium sulfate was added to remove water, the solution was filtered, and the solvent was removed in vacuo. The residue was placed under reduced pressure for seven hours to provide the desired alcohol 4.6 g (100%) as a yellow oil which was generally used without further purification. A portion of the crude product was purified by flash chromatography on silica gel (10:1, followed by 2:1 hexanes/ethyl acetate) to afford pure alcohol as a white solid: $^1$H NMR (300 MHz, CDCl$_3$) δ 7.60 (d, 1H, J=2.3 Hz), 7.43 (d, 1H, J=8.1 Hz), 7.24 (t, 1H, J=7.7 Hz), 7.16 (d, 1H, J=7.4 Hz), 6.85-6.86 (m, 1H), 4.84 (s, 3H), 2.34 (bs, 1H).

Step D: A solution of oxalyl chloride (2.9 ml, 33.0 mmol) in methylene chloride (75 ml) was stirred under nitrogen at −78° C. as dimethyl sulfoxide (5.2 ml, 73.0 mmol) was added dropwise. The resulting mixture was stirred at −78° C. for 10 minutes, then a solution of compound from Step C (4.5 g, 30.0 mmol) in methylene chloride (75 ml) was added dropwise over 20 minutes. The mixture was stirred at −78° C. for 20 minutes longer, then triethylamine (21.0 ml, 150 mmol) was added rapidly, and the reaction mixture was allowed to warm to room temperature and stirred overnight under nitrogen. The mixture was diluted with methylene chloride and water. The methylene chloride layer was removed and the aqueous portion extracted twice with methylene chloride. The organic layers were combined, washed with brine, dried over anhydrous sodium sulfate, filtered, and the solvent removed in vacuo. The residue was purified by flash chromatography on silica gel (5:1, followed by 1:1 hexanes/ethyl acetate) to afford the desired benzofuran aldehyde, 3.1 g (70%) as yellow oil: $^1$H NMR (300 MHz, CDCl$_3$) δ 10.19 (s, 1H), 7.79 (d, 1H, J=2.1 Hz), 7.73 (t, 1H, J=7.4 Hz), 7.51 (d, 1H, J=1.7 Hz), 7.43 (t, 1H, J=7.8 Hz).

Step E: The product from Step D (2.91 g, 20 mmol), as a solution in methanol (30 ml) was added dropwise to 40% aqueous methylamine (3.4 ml, 40 mmol) in methanol. The reaction mixture was stirred overnight at room temperature under nitrogen, then cooled to 0° C. and sodium borohydride (0.8 g, 20 mmol) was added in small portions over two minutes. The resulting mixture was stirred for 2.5 hours at room temperature, then quenched with water and extracted (3×) with 2N HCl. The aqueous extracts were made basic with 6N NaOH (pH 10) and the product extracted into methylene chloride and dried over anhydrous sodium sulfate. Filtration and concentration afforded the desired methyl amine, 2.88 g (89%), as a light yellow oil: $^1$H NMR (300 MHz, CDCl$_3$) δ 7.62 (d, 1H, J=2.3 Hz), 7.42 (d, 1H, J=8.0 Hz), 7.25 (t, 1H, J=7.7 Hz), 7.16-7.19 (m, 1H), 6.88-6.89 (m, 1H), 3.98 (bs, 2H), 2.48 (bs, 3H).

Step F: The product from Step E (2.99 g, 19.0 mmol), 2-bromoacetophenone (3.7 g, 19.0 mmol), and triethylamine (2.7 ml, 19.6 mmol) in methylene chloride (40 ml).were stirred at room temperature under nitrogen overnight. The mixture was diluted with methylene chloride, washed with water, and dried over anhydrous sodium sulfate. Filtration and concentration in vacuo provided the alkylation product, 5.3 g (99%), as a yellow-orange oil: $^1$H NMR (300 MHz, CDCl$_3$) δ 7.89-7.93 (m, 2H), 7.38-7.61 (m, 4H), 7.17-7.27 (m, 3H), 6.99 (d, 1H, J=1.9 Hz), 3.90 (s, 2H), 3.83 (s, 2H), 2.39 (s, 3H).

Step G: To a solution of the product from Step F (5.3 g, 18.8 mmol) in methanol (50 ml) at 0° C. was added sodium borohydride (1.4 g, 37.6 mmol). After stirring for 1.5 hour at room temperature, the reaction was quenched with water, then extracted (3×) with methylene chloride. The combined organic extracts were washed with brine, dried over anhydrous sodium sulfate, filtered, and concentrated in vacuo. The residue was purified by flash chromatography on silica gel (slow gradient from 10:1 to 1:1 hexanes/ethyl acetate) to provide amino alcohol, 3.22 g (61%), as a viscous yellow oil: $^1$H NMR (300 MHz, CDCl$_3$) δ 7.65 (d, 1H, J=2.3 Hz), 7.46 (d, 1H, J=8.2 Hz), 7.23-7.34 (m, 6H), 7.16 (d, 1H, J=7.3 Hz), 6.93-6.94 (m, 1H), 4.74-4.78 (m, 1H), 3.91-4.00 (m, 2H), 3.75 (d, 1H, J=12.9 Hz), 2.54-2.68 (m, 2H), 2.35 (s, 3H).

Step H: A solution of the product from Step G (3.2 g, 11.5 mmol) in methylene chloride was stirred at room temperature under nitrogen as methanesulfonic acid (17 ml, 260.0 mmol) was added dropwise over 30 minutes. The reaction solution was stirred overnight at room temperature under nitrogen, then cooled to 0° C. and treated with 2N NaOH until the pH of the aqueous layer was 12, and then diluted with water. The methylene chloride layer was removed and the aqueous portion extracted twice with methylene chloride. The combined organic layers were washed with brine, dried over anydrous sodium sulfate, filtered, and the solvent removed in vacuo. The reaction material was basified with 10% aqueous ammonium hydroxide. The resulting white, cloudy mixture was extracted (3×) with methylene chloride and the organic layers were combined, washed with brine, dried over anhydrous sodium sulfate, filtered and the solvent removed in vacuo to provide the target cyclized tethydroisoquinoline, 2.0 g, as a light brown oil: $^1$H NMR (300 MHz, CDCl$_3$) δ 7.62 (d, 1H, J=2.3 Hz), 7.17-7.33 (m, 6H), 6.81 (d, 1H, J=8.6 Hz), 6.73 (d, 1H, J=2.2 Hz), 4.33-4.37 (m, 1H), 3.96 (d, 1H, J=15.2 Hz), 3.79 (d, 1H, J=14.5 Hz), 3.04-3.10 (m, 1H), 2.62-2.68 (m, 1H), 2.50 (s, 3H). The free-base (2.0 g, 7.6 mmol) and maleic acid (0.88 g, 7.6 mmol) were dissolved in absolute ethanol (70 ml) by heating to reflux very briefly. The solution was allowed to cool to room temperature, during which time an off-white precipitate formed. Isolation of the solid by vacuum filtration provided the desired maleate salt, 1.45 g (33% from the product of Step G), as an off-white solid; mp 199-204° C.; $^1$H NMR (300 MHz, CD$_3$OD) δ 7.88 (d, 1H, J=2.3 Hz), 7.33-742 (m, 4H), 7.23-7.26 (m, 2H), 6.96-6.98 (m, 1H), 6.84 (d, 1H, J=8.7 Hz), 6.22 (s, 2H), 4.82-4.88 (m, 1H), 4.64-4.74 (m, 2H), 3.84-3.90 (m, 1H), 3.55-3.63 (m, 1H), 3.13 (s, 3H); IR (KBr) 3448, 2363, 1700, 1578, 1456, 1354, 1049, 869, 748, 703, 652, 576 cm$^{-1}$; API MS m/z=264 [C$_{18}$H$_{17}$NO+H]$^+$; Anal. Calcd. For C$_{18}$H$_{17}$NO—C$_4$H$_4$O$_4$-0.25H$_2$O: C, 72.11; H, 6.05; N, 4.67. Found: C, 71.89; H, 6.01; N, 4.59.

Example 13

The free base of the product from Example 12, Step H (0.029 g) in absolute ethanol (6 ml) was hydrogenated over 5% Pd/C (0.030 g) at slightly above atmospheric pressure for 3 days. The catalyst was removed by filtration and the solvent removed in vacuo. The residue was subjected to column chromatography on silica gel (2:1 hexanes/ethyl acetate) to provide the dihydrobenzofuran free base, 0.015 g (52%), as a colorless gum: $^1$H NMR (300 MHz, CDCl$_3$) □ 7.17-7.31 (m, 5H), 6.63 (d, 1H, J=8.3 Hz), 6.54 (d, 1H, J=8.3 Hz), 4.61 (t, 2H, J=8.7 Hz), 4.18-4.23 (m, 1H); 3.64 (d, 1H, J=15.1 Hz), 3.47 (d, 1H, J=15.3 Hz), 3.08 (t, 2H, J=8.5 Hz), 2.97-3.03 (m, 1H), 2.56 (dd, 1H, J=8.6, 11.5 Hz), 2.44 (s, 3H). The free-base (0.012, 0.045 mmol) and maleic acid (0.005 g, 0.045 mmol) were dissolved in absolute ethanol (7 ml) and heated to reflux under nitrogen for 10 minutes. The solvent was removed in vacuo and the residue recrystallized from ethanol/diethyl ether to provide the desired maleate salt, 0.014 g (79%) as a white solid: mp 168-169° C.; $^1$H NMR (300 MHz, CD$_3$OD) δ 7.31-7.40 (m, 3H), 7.22-7.25 (m, 2H), 6.63 (s, 3H), 6.24 (s, 3H), 4.63 (t, 1H, J=8.7 Hz), 4.40-4.51 (m, 3H), 3.73-3.79 (m, 1H), 3.43-3.53 (m, 1H), 3.12-3.27 (m, 2H), 3.06 (s, 3H); IR (KBr) 3448, 2923, 2364, 1578, 1484, 1355, 1258, 981, 868, 702, 574 cm$^{-1}$; CI MS m/z=266 [C$_{18}$H$_{19}$NO+H]$^+$.

Example 14

To a stirred solution of the appropriate amine product prepared using the procedures of Step H of Example 12 (1.3 g, 4.3 mmol) in anhydrous ether (40 mL), 1 M ethereal HCl (8.7 mL, 8.7 mmol) was added under nitrogen. The resulting solid was filtered, washed with ether, and dried to afford the product hydrochloride salt as a white solid (1.4 g, 95%): mp 240-243° C.; $^1$H NMR (500 MHz, CD$_3$OD) δ 7.87 (d, J=2.2 Hz, 1H), 7.45 (d, J=8.6 Hz, 1H), 7.32-7.20 (m, 2H), 7.12 (s, 1H), 6.99 (dd, J=1.0, 2.23 Hz, 1H), 4.88-4.74 (m, 3H), 3.90 (dd, J=12.2, 6.0 Hz, 1H), 3.62 (s, 1H), 3.15 (s, 3 H); IR (KBr) 3423, 2935, 2547, 1610; CI MS m/z=300 [C$_{18}$H$_{15}$F$_2$NO+H]$^+$; Anal. Calcd. for C$_{18}$H$_{15}$F$_2$NO—HCl-0.20 H$_2$O: C, 63.70; H, 4.87; N, 4.13. Found: C, 63.50; H, 4.72; N, 4.06.

Example 15

The appropriate unsaturated amine (320 mg, 1.07 mmol) prepared using the procedures of Example 12, Step H was treated according to reaction conditions described for Example 13. Upon purification of the crude residue by chromatography (SiO$_2$, EtOAc/hexanes, 1/1), the free amine product was isolated (230 mg, 71%) as a white solid: mp 86-90° C.; $^1$H NMR (500 MHz, CDCl$_3$) δ 6.92-7.05 (m, 3H), 6.62 (d, J=8.3 Hz, 1 H), 6.56 (d, J=8.3 Hz, 1 H), 4.60 (t, J=8.6 Hz, 2H), 4.12 (t, J=6.1 Hz, 1H), 3.52 (s, 2H), 3.07 (t, J=8.6 Hz, 2H), 2.90 (dd, J=11.4, 5.2 Hz, 1H), 2.56 (dd, J=11.4, 7.4 Hz, 1H), 2.42 (s, 3H); IR (KBr) 2940, 1609, 1517 cm$^{-1}$ CI MS m/z=302 [C$_{18}$H$_{17}$F$_2$NO+H]$^+$; Anal. Calcd. for C$_{18}$H$_{17}$F$_2$NO: C, 71.75; H, 5.69 N, 4.65. Found: C, 71.50; H, 5.61; N, 4.59.

Example 16

To a stirred solution of the appropriate amine product prepared using the procedures of Step H of Example 12 (1.6 g, 5.4 mmol) in anhydrous ether (50 mL), 1 M ethereal HCl (10.7 mL, 10.7 mmol) was added under nitrogen. The resulting solid was filtered, washed with ether, and recrystallized in methanol to afford a white solid (950 mg, 50%): mp 256-258° C.; $^1$H NMR (500 MHz, CD$_3$OD) δ 7.90 (d, J=2.2 Hz, 1H), 7.48 (d, J=8.6 Hz, 1H), 6.91-6.99 (m, 5H), 4.75-4.84 (m, 3H), 3.92 (dd, J=12.5, 6.0 Hz, 1H), 3.62 (br s, 1H), 3.15 (s, 3 H); IR (KBr) 3424, 2467, 1624, 1597 cm$^{-1}$; MS (API) m/z=300 [C$_{18}$H$_{15}$F$_2$NO+H]$^+$; Anal. Calcd. for C$_{18}$H$_{15}$F$_2$NO—HCl-0.20 H$_2$O: C, 63.70; H, 4.87; N, 4.13. Found: C, 63.50; H, 4.72; N, 4.06.

Example 17

The appropriate unsaturated amine (750 mg, 2.51 mmol) prepared using the procedures of Example 12, Step H was treated according to reaction conditions described for Example 13. Upon purification of the crude residue by chromatography (SiO$_2$, EtOAc/hexanes, 1/1), the free amine product was isolated (444 mg, 59%) as a white solid:

mp 107-109° C., $^1$H NMR (500 MHz, CDCl$_3$) δ 6.56-6.75 (m, 5H), 4.61 (t, J=8.6 Hz, 2H), 4.13 (t, J=5.9 Hz, 1H), 3.54 (d, J=15.3 Hz, 1 H), 3.49 (d, J=15.3 Hz, 1H), 3.08 (t, J=8.6 Hz, 2H), 2.91 (dd, J=11.5, 5.5 Hz, 1H), 2.60 (dd, J=11.5, 5.9 Hz, 1H), 2.42 (s, 3H); IR (KBr) 3077, 1626, 1597 cm$^-$; CI MS m/z=302 [C$_{18}$H$_{17}$F$_2$NO+H]$^+$; Anal. Calcd. for C$_{18}$H$_{17}$F$_2$NO: C, 71.75; H, 5.69; N, 4.65. Found: C, 71.41; H, 5.75; N, 4.42.

Example 20

The appropriate amine product prepared using the procedures of Step H of Example 12 (2.8 g, 10.0 mmol) was dissolved in ethyl ether (20 mL). Some of the material was insoluble, so the solution was decanted away from the solids. The decanted solution was treated with 1M HCl/Et$_2$O (8.2 mL, 8.2 mmol). An off-white precipitate formed immediately. The solid was filtered, yielding 2.0 g which was recrystallized from methanol/Et$_2$O to provide hydrochloride salt (1.4 g, 56%): mp 190-192° C.; $^1$H NMR (300 MHz, CD$_3$OD) δ 7.87 (d, J=2.2 Hz, 1 H), 7.39 (d, J=8.7 Hz, 1 H), 7.35-7.26 (m, 2 H), 7.12 (t, J=8.7 Hz, 2 H), 6.99 (d, J=1.4 Hz, 1 H), 6.79 (d, J=8.7 Hz, 1 H), 5.01-4.85 (m, 1 H), 4.80-4.60 (m, 1 H), 3.92-3.80 (m, 1 H), 3.57 (t, J=12 Hz, 1 H), 3.34 (s, 1 H), 3.17 (s, 3 H); IR (KBr) 3422, 2926, 2550, 1508, 1224 cm$^{-1}$ CI MS m/z=282 [C$_{18}$H$_{16}$FNO+H]$^+$; Anal. Calcd. for C$_{18}$H$_{16}$FNO—HCl-0.75 H$_2$O: C, 65.26; H, 5.63; N, 4.23. Found: C, 65.51; H, 5.35; N, 4.14.

Example 21

The appropriate unsaturated amine (512 mg, 1.83 mmol) prepared using the procedures of Example 12, Step H was treated according to reaction conditions described for Example 13. Upon purification of the crude residue by chromatography (SiO$_2$, EtOAc/hexanes, 1/1), the product was isolated as the free amine (200 mg, 38%) as a light yellow solid: mp 110-116° C.; $^1$H NMR (300 MHz, CDCl$_3$) δ 7.16-7.08 (m, 2H), 6.91 (t, J=8.7 Hz, 2H), 6.60 (d, J=8.3 Hz, 1H), 6.51 (d, J=8.3 Hz, 1H), 4.59 (t, J=8.7 Hz, 2H), 4.16 (t, J=6.9 Hz, 1H), 3.59 (d, J=15.2 Hz, 1H), 3.47 (d, J=15.2 Hz, 1H), 3.08 (t, J=8.5 Hz, 2H), 2.92 (dd, J=11.5, 5.5 Hz, 1H), 2.50 (dd, J=11.5, 5.9 Hz, 1H), 2.43 (s, 3H); IR (KBr) 2874, 2784, 1599, 1505, 1217 cm$^{-1}$; CI MS m/z=284 [C$_{18}$H$_{18}$FNO+H]$^+$; Anal. Calcd. for C$_{18}$H$_{18}$FNO$_2$: C, 76.30; H, 6.40; N, 4.94. Found: C, 75.96; H, 6.43; N, 4.82.

Example 22

To a solution of the appropriate amino alcohol product prepared using the procedures of Step G of Example 12 (2.5 g, 7.9 mmol) in methylene chloride (40 mL), methanesulfonic acid (10 mL, 150 mmol) was added at room temperature over 10 min. The reaction mixture was warmed to reflux under nitrogen overnight. After the mixture was cooled down to room temperature, 2 N NaOH was added until pH ~11 and the resulting solution was extracted (3×) with methylene chloride. The combined organic layers were washed with brine, dried over MgSO$_4$ and concentrated in vacuo. The residue was purified by chromatography (SiO$_2$, EtOAc/hexanes, 1/2) to give the product as an oil (1.2 g, 50%): $^1$H NMR (500 MHz, CDCl$_3$) δ 7.63 (d, J=2.0 Hz, 1 H), 7.24 (d, J=6.0 Hz, 1 H), 7.20 (d, J=2.0 Hz, 1 H), 7.19 (s, 2 H), 7.08 (d, J=5.6 Hz, 1 H), 6.80 (d, 8.4 Hz, 1 H), 6.73 (d, J=1.4 Hz, 1 H), 4.30 (t, J=7.5 Hz, 1 H), 3.88 (d, J=13.0 Hz, 1 H), 3.85 (d, J=13.0 Hz, 1 H), 3.02 (dd, J=11.5, 7.5 Hz, 1 H), 2.66 (dd, J=11.5, 7.5 Hz, 1 H), 2.48 (s, 3 H); IR (MeOH) 2950, 2778, 1593, 1432 cm$^{-1}$; CI MS m/z=298 [C$_{18}$H$_{16}$ClNO+H]$^+$; Anal. Calcd. for C$_{18}$H$_{16}$ClNO—HCl- 0.1 H$_2$O: C, 64.34; H, 5.16; N, 4.17. Found: C, 63.98; H, 5.07; N, 3.91.

Example 23

The method described in Example 25 was used to make Example 23. Methanesulfonic acid (18 mL, 280 mmol) was added at ambient temperature to a solution of the analogous amino alcohol (3.6 g, 11.2 mmol) in methylene chloride (50 mL). The reaction mixture was warmed to reflux under nitrogen overnight. After the reaction was cooled to room temperature and was made basic (pH 11) with 2 N NaOH, the mixture was extracted (3×) with methylene chloride. The combined organic layers were washed with brine, dried over MgSO$_4$, and concentrated in vacuo. The residue was purified by chromatography (SiO$_2$, EtOAc/hexanes, 1/1) to give the desired product, Example 21 (1.70 g, 51%) as a white powder: mp 78-80° C.; $^1$H NMR (500 MHz, CDCl$_3$) δ 7.12 (m, 3H), 7.08 (d, J=8.0 Hz, 1H), 6.62 (d, J=8.2 Hz, 1H), 6.56 (d, J=8.2 Hz, 1H), 4.60 (t, J=8.6 Hz, 2H), 4.16 (t, J=5.0 Hz, 1H), 3.57 (d, J=15.3 Hz, 1 H), 3.50 (d, J=15.3 Hz, 1H), 3.08 (t, J=8.6 Hz, 2H), 2.94 (dd, J=11.4, 5.0 Hz, 1H), 2.57 (dd, J=11.4, 7.8 Hz, 1H), 2.43 (s, 3H); IR (CH$_2$Cl$_2$) 2940, 2784, 1594 cm$^{-1}$; CI MS m/z=300 (C$_{18}$H$_{18}$ClNO+H)$^+$; Anal. Calcd. for C$_{18}$H$_{18}$ClNO: C, 72.11; H, 6.05; N, 4.67. Found: C, 71.87; H, 6.09; N, 4.45, along with 1.4 g of starting material was recovered.

Example 24

The appropriate amine product prepared using the procedures of Step H of Example 12 (0.5 g, 3.0 mmol) was dissolved in ethyl ether (10 mL) and was treated with a solution of 1 M hydrochloric acid in ethyl ether (1.7 mL, 1.7 mmol). An off-white precipitate formed immediately, which was filtered to give the product (320 mg,. 60%): mp 230-234° C.; $^1$H NMR (300 MHz, CD$_3$OD) δ 7.87 (d, J=2.0 Hz, 1H), 7.48-7.32 (m, 3H), 7.27 (d, J=8.4 Hz, 2H), 6.99 (d, J=1.6 Hz, 1H), 6.78 (d, J=8.7 Hz, 1H), 4.95-4.67 (m, 3H), 3.93-3.78 (m, 1H), 3.58 (t, J=12.2 Hz, 1H), 3.17 (s, 3H); IR (KBr) 3422, 2926, 2589, 1490, 1089 cm$^{-1}$; CI MS m/z=298 [C$_{18}$H$_{16}$ClNO+H]$^+$.

Example 25

Step A: To a solution of N-Methylamine (5.0 g, 31 mmol, prepared in Example 12, Step E) in ethanol (50 mL), 10% Pd/C (2.5 g) was added under nitrogen. The reaction flask was evacuated and filled with hydrogen, then evacuated. This was repeated two more times. The reaction vessel was placed in a Parr shaker with hydrogen (45 psi) and shaken for 18 h. The mixture was filtered through a pad of celite, and the celite pad was washed with methanol. The filtrate was concentrated in vacuo to provide N-methyl-4-(2,3-dihydrobenzofuranyl)amine (4.8 g, 94%) as a yellow oil: $^1$H NMR (300 MHz, CDCl$_3$) δ 7.10 (t, J=8.2 Hz, 1H), 6.79 (d, J=8.3 Hz, 1H), 6.67 (d, J=8.3 Hz, 1H), 4.50 (t, J=8.6 Hz, 2H), 3.65 (s, 2H), 3.07 (t, J=8.6 Hz, 2H), 2.42 (s, 3H).

Step B: A solution of N-methyl-4-(2,3-dihydrobenzofuranyl)amine from Step A (2.2 g, 13 mmol) and triethylamine (1.4 mL) in dichloromethane (25 mL) was cooled in an ice water bath. 4'-Chlorophenacyl bromide (13.8 mmol) was added, and the reaction was allowed to warm to room temperature. The reaction mixture was washed with water, and the organic layer was dried over MgSO$_4$, filtered, and concentrated to yield the desired amino ketone as a dark orange oil (3.7 g, 86% crude): $^1$H NMR (300 MHz, CDCl$_3$) δ 7.82 (d, J=8.5 Hz, 2H), 7.37 (d, J=8.4 Hz, 2H), 7.07 (t, J=7.8 Hz, 1H), 6.79 (d, J=7.6 Hz, 1H), 6.72 (d, J=8.0 Hz, 1H), 4.52 (t, J=8.8 Hz, 2H), 3.74 (s, 2H), 3.61 (s, 2H), 3.16 (t, J=8.7 Hz, 2H), 2.37 (s, 3H).

Step C: Amino ketone prepared in Step B (3.7 g, 12 mmol) was dissolved in methanol (40 mL) and cooled in an ice water bath. Sodium borohydride (0.44 g, 12 mmol) was added portionwise. The reaction was stirred for 1 h. The reaction mixture was concentrated to half of the original volume. Water (40 mL) was added, and the mixture was extracted (3×) with dichloromethane. The combined organic layers were dried over MgSO$_4$, filtered, and concentrated to provide the desired amino alcohol as a light yellow oil (2.5 g, 67% crude): $^1$H NMR (300 MHz, CDCl$_3$) δ 7.35-7.20 (m, 4H), 7.08 (t, J=7.8 Hz, 1H), 6.78 (d, J=7.6 Hz, 1H), 6.72 (d, J=8.0 Hz, 1H), 4.70 (dd, J=8.6, 5.5 Hz, 1H), 4.55 (t, J=8.6 Hz, 2H), 3.65 (d, J=12.9 Hz, 1H), 3.44 (d, J=12.9 Hz, 1H), 3.18 (t, J=8.6 Hz, 2H), 2.57-2.52 (m, 2H), 2.29 (s, 3H).

Step D: The amino alcohol (2.4 g, 7.5 mmol, from Step C) was stirred in CH$_2$Cl$_2$ (40 mL) and CH$_3$SO$_3$H (9.8 mL) was added over 5 min. The reaction was stirred at ambient temperature until no starting material was detected by NMR analysis (24 h), then the solution was made basic with aqueous 2N NaOH. The layers were separated and the aqueous layer was extracted (2×) with CH$_2$Cl$_2$. The organic extracts were combined, washed with brine, dried over MgSO$_4$, filtered, and concentrated in vacuo to yield a brown solid which was chromatographed (SiO$_2$, 20% EtOAc/hexanes) to yield the desired product, Example 23 (1.13 g, 50%): mp 148-150° C.; $^1$H NMR (300 MHz, CDCl$_3$) δ 7.23 (d, J=8.5 Hz, 2H), 7.11 (d, J=8.4 Hz, 2H), 6.60 (d, J=8.3 Hz, 1H), 6.54 (d, J=8.3 Hz, 1H), 4.60 (t, J=8.7 Hz, 2H), 4.16 (t, J=6.5 Hz, 1H), 3.59 (d, J=15.2 Hz, 1H), 3.47 (d, J=15.2 Hz, 1H), 3.07 (t, J=9.0 Hz, 2H), 2.93 (dd, J=11.3, 5.2 Hz, 1H), 2.53 (dd, J=11.4, 8.0 Hz, 1H), 2.42 (s, 3H); IR (KBr) 2944, 2788, 1480, 1253, 823 cm$^{-1}$; CI MS m/z=300 [$C_{18}H_{18}ClNO+H$]$^+$; Anal. Calcd. for $C_{18}H_{18}ClNO$: C, 72.11; H, 6.05; N, 4.67. Found: C, 72.03; H, 6.17; N, 4.56.

Example 30

An ice-cold solution of the appropriate amine product prepared using the procedures of Step H of Example 12 (450 mg, 1.44 mmol) in $CH_2Cl_2$ (10 mL) was treated with 1 M HCl/$Et_2O$ (1.5 mL, 1.5 mmol). An off-white precipitate formed after approximately 30 min. The solution was stirred at room temperature for 1 h and concentrated in vacuo. The residue was dissolved in methanol (10 mL) at 50° C., cooled to room temperature and the crystallization started by adding $Et_2O$ (20 mL). The solution was left to crystallize overnight. This procedure was repeated several times to provide the hydrochloride salt as an off-white powder (106 mg, 30%): mp 279-284° C.; $^1$H NMR (300 MHz, $CD_3OD$) δ 7.91-7.90 (m, 1H), 7.50-7.47 (m, 1H), 7.24-7.17 (m, 2H), 7.02-6.98 (m, 2H), 6.89-6.86 (m, 1H), 4.85-4.73 (m, 3H), 3.92 (dd, J=12.1, 6.1 Hz, 1H), 3.70-3.60 (m, 1H), 3.15 (s, 3H). IR (KBr) 3424, 2933, 2466, 1606, 1590, 1443, 1137, 860 cm$^{-1}$; CI MS m/z=316 ($C_{18}H_{15}ClFNO+H$]$^+$; Anal. Calcd. for $C_{18}H_{15}ClFNO$—HCl-0.25$H_2O$: C, 60.60; H, 4.66; N, 3.93. Found: C, 60.30; H, 4.79; N, 3.66.

Example 32

The appropriate amine product prepared using the procedures of Step H of Example 12 (0.88 g, 3.0 mmol) was dissolved in ethyl ether (25 mL) and treated with a solution of 1 M hydrochloric acid in ethyl ether (3.4 mL, 3.4 mmol). An off-white precipitate formed immediately, which was filtered to yield an off white solid (795 mg, 80%): mp 212-214° C.; $^1$H NMR (300 MHz, $CD_3OD$) δ 7.88 (d, J=2.2 Hz, 1H), 7.40 (d, J=8.5 Hz, 1H), 7.16 (d, J=8.0 Hz, 2H), 6.97-6.77 (m, 4H), 4.65-4.56 (m, 1H), 3.87-3.75 (m, 2H), 3.80 (s, 3H), 3.65-3.46 (m, 2H), 3.17 (s, 3H); IR (KBr) 3424, 2930, 2547, 1513, 1030 cm$^{-1}$ CI MS m/z=294 [$C_{19}H_{19}NO_2+H$]$^+$; Anal. Calcd. for $C_{19}H_{19}NO_2$—HCl-0.25 $H_2O$: C, 68.26; H, 6.18; N, 4.19. Found: C, 68.01; H, 6.20; N, 3.93.

Example 33

The appropriate unsaturated amine (660 mg, 2.26 mmol) prepared using the procedures of Example 12, Step H was treated according to reaction conditions described for Example 13. Upon purification of the crude residue by chromatography ($SiO_2$, EtOAc/hexanes, 1/1), the product was isolated as the free amine (220 mg, 33%) as a light yellow solid: mp 119-121° C.; $^1$H NMR (300 MHz, $CDCl_3$) δ 7.08 (d, J=8.4 Hz, 5H), 6.80 (d, J=8.5 Hz, 2H), 6.62 (d, J=8.3 Hz, 1H), 6.51 (d, J=8.3 Hz, 1H), 4.59 (t, J=8.7 Hz, 2H), 4.15 (t, J=6.9 Hz, 1H), 3.78 (s, 3H), 3.61 (d, J=15.2 Hz, 1H), 3.43 (d, J=15.2 Hz, 1H), 3.08 (t, J=8.5 Hz, 2H), 2.92 (dd, J=11.5, 5.5 Hz, 1H), 2.50 (dd, J=11.5, 5.9 Hz, 1H), 2.42 (s, 3H); IR (KBr) 2785, 2762, 1610, 1509, 1251 cm$^{-1}$; CI MS m/z=296 [$C_{19}H_{21}NO_2+H$]$^+$; Anal. Calcd. for $C_{19}H_{21}NO_2$: C, 77.26; H, 7.17; N, 4.74. Found: C, 76.93; H, 7.31; N, 4.57.

Example 34

The free base of the product from Example 12, Step H (0.3 g, 1.14 mmol) as a solution in anhydrous tetrahydrofuran at −78° C. was treated with a solution of n-BuLi (0.91 ml, 2.5 M in hexanes, 2.3 mmol) under nitrogen. After stirring for two hours, iodomethane (0.17 ml, 2.7 mmol) was added dropwise. The resulting mixture was stirred at −78° C. for two hours, then allowed to warm to room temperature. The mixture was diluted with water and extracted (3×) with diethyl ether. The organic layers were combined, washed with brine, dried over anhydrous sodium sulfate, filtered, and the solvent was removed in vacuo. The residue was purified by column chromatography on silica gel using a slow gradient from 0 to 10% methanol in methylene chloride to provide the methyl-substituted benzofuran, 203 mg (64%) as a yellow oil: $^1$H NMR (300 MHz, $CDCl_3$) δ 7.15-7.28 (m, 5H), 7.10 (d, 1H, J=8.7 Hz), 6.70 (d, 1H, J=8.5 Hz), 6.28-6.29 (m, 1H), 4.29-4.34 (m, 1H), 3.86 (d, 1H, J=15.2 Hz), 3.70 (d, 1H, J=15.2 Hz), 3.00-3.05 (m, 1H), 2.58-2.65 (m, 1H), 2.44 (s, 3H), 2.40 (s, 3H). The free-base (0.23 g, 0.73 mmol) and maleic acid (0.085 g, 0.073 mmol) were dissolved in absolute ethanol (10 ml) and heated to reflux under nitrogen for 5 minutes then allowed to cool to room temperature. The mixture was concentrated in vacuo to a volume of approximately 2 ml, then diethyl ether was added, causing crystals to form. Isolation of the solid by vacuum filtration provided an off-white solid. The solid was recrystallized from ethanol/diethyl ether, then from ethanol, to provide the desired maleate salt, 0.043 g (15%), as a white, crystalline solid: mp 187-192° C.; $^1$H NMR (300 MHz, $CD_3OD$) δ 7.23-7.40 (m, 6H), 6.73 (d, 1H, J=8.6 Hz), 6.57 (s, 1H), 6.21 (s, 2H), 4.63-4.80 (m, 3H), 3.83-3.88 (m, 1H), 3.53-3.61 (m, 1H), 3.12 (s, 3H), 2.48 (s, 3H); IR (KBr) 3448, 2548, 1584, 1495, 1354, 1270, 1195, 1078, 936, 866, 808, 704, 656, 583, 510 cm$^{-1}$ CI MS m/z=278 [$C_{19}H_{19}NO+H$]$^+$; Anal. Calcd. For $C_{19}H_{19}NO$—$C_4H_4O_4$-0.5$H_2O$: C, 68.84; H, 6.01; N, 3.48. Found C, 68.49; H, 5.84; N, 3.41.

Example 36

Step A: The free base of the product from Example 12, Step H (1.0 g, 3.91 mmol) as a solution in anhydrous tetrahydrofuran at −78° C. was treated with a solution of n-BuLi (3.3 ml, 2.5 M in hexanes, 8.2 mmol) under nitrogen. After stirring for one hour, dimethylformamide (0.70 ml, 9.0 mmol) was added dropwise. The resulting mixture was stirred at −78° C. for two hours, then allowed to warm to room temperature. The mixture was diluted with water and extracted (3×) with diethyl ether. The organic layers were combined, washed with brine, dried over anhydrous sodium sulfate, filtered, and the solvent was removed in vacuo. The residue was purified by column chromatography on silica gel (1:1 hexanes/ethyl acetate) to provide the expected aldehyde, 430 mg (38%), as a light yellow oil: $^1$H NMR (300 MHz, $CDCl_3$) δ 9.86 (s, 1H), 7.54 (s, 1H), 7.17-7.33 (m, 6H), 7.05 (d, 1H, J=8.7 Hz), 4.32-4.36 (m, 1H), 4.00 (d, 1H, J=15.5 Hz), 3.83 (d, 1H, J=15.5 Hz), 3.07-3.13 (m, 1H), 2.67 (dd, 1H, J=8.2, 11.5 Hz), 2.51 (s, 3H); CI MS m/z=292 [$C_{19}H_{17}NO_2+H$]$^+$.

Step B: The product from Example 36, Step A (0.07 g, 0.23 mmol) was treated with sodium borohydride (0.02 g, 0.46 mmol) in chilled methanol (20 ml). The reaction mixture was allowed to warm to room temperature and stirred for 1 hour, quenched with water, and extracted (3×) with methylene chloride. The organic layers were combined, washed with brine, dried over anhydrous sodium sulfate, filtered, and the solvent removed in vacuo to provide the alcohol, 0.07 g, (100%) as a yellow oil: $^1$H NMR (300 MHz, CDCl$_3$) δ 7.17-7.32 (m, 6H), 6.79 (d, 1H, J=8.5 Hz), 6.57 (s, 1H), 4.76 (s, 2H), 4.33-4.38 (m, 1H), 3.89 (d, 1H, J=15.2 Hz), 3.72 (d, 1H, J=15.2 Hz), 3.06-3.11 (m, 1H), 2.63 (dd, 1H, J=8.6, 11.4 Hz), 2.50 (s, 3H); CI MS m/z=294 [C$_{19}$H$_{19}$NO$_2$+H]$^+$. The free-base (0.03 g, 0.10 mmol) and hydrochloric acid (1M soln. in diethyl ether, 0.5 ml) were dissolved in diethyl ether (4 ml). The resultant off-white precipitate was isolated by vacuum filtration and dried under reduced pressure to provide the desired hydrochloride salt, 0.03 g (72%), mp 149-162° C.; $^1$H NMR (300 MHz, CD$_3$OD) δ 7.25-7.42 (m, 6H), 6.78-6.86 (m, 2H), 4.64-4.74 (m, 5H), 2.85-2.91 (m, 1H), 3.52-3.68 (m, 1H), 3.15 (s, 3H); IR (KBr) 3375, 2500, 1456, 1023, 811, 702 cm$^{-1}$; CI MS m/z=294 [C$_{19}$H$_{19}$NO$_2$+H]$^+$; Anal. Calcd. for C$_{19}$H$_{19}$NO$_2$-HCl-0.75H$_2$O: C, 66.47; H, 6.31; N, 4.08. Found: C, 66.13; H, 6.54; N, 3.82.

Example 38

Step A: To a mixture of lithium aluminum hydride (1.3 g, 34 mmol) in THF (200 mL), methyl 4-indole carboxylate (3.0 g, 17 mmol) in THF (100 mL) was added dropwise at room temperature. The reaction mixture was stirred at room temperature for 2 h and then quenched with ethyl acetate. The mixture was treated with water (1.3 mL), 15% NaOH (1.3 mL) and water (3.9 mL), and then filtered. The filtrate was concentrated in vacuo to afford the crude 4-(hydroxymethyl)-indole (2.5 g,99%): $^1$H NMR (500 MHz, CDCl$_3$) δ 8.29 (br s, 1H),7.34 (d, J=9.0 Hz, 1H), 7.16-7.22 (m, 2H), 7.12 (d, J=7.0 Hz, 1H), 6.67 (t, J=1.0 Hz, 1H), 4.98 (d, J=4.2 Hz, 2H); CI MS m/z 147 [C$_9$H$_9$NO+H]$^+$.

Step B: Tetrapropylammonium perruthenate (0.3 g, 0.85 mmol) was added in portions to a mixture of alcohol product from Step A (2.5 g, 17 mmol), N-methylmorpholine N-oxide (3.0 g, 25 mmol) and 4 Å molecular sieves (3.0 g) in anhydrous methylene chloride (30 mL) at room temperature. The mixture was stirred at room temperature under nitrogen for 1 h and then filtered. The filtrate was concentrated in vacuo, and the residue was purified by chromatography (SiO$_2$, CH$_2$Cl$_2$) to provide indole-4-aldehyde as a white powder (2.0 g, 80%): $^1$H NMR (300 MHz, CDCl$_3$) δ 10.2 (s, 1H), 8.52 (br s, 1H), 7.64-7.69 (m, 2H), 7.31-7.44 (m, 3H); CI MS m/z=146 [C$_9$H$_7$NO+H]$^+$.

Step C: To a solution of aldehyde product from Step B (2.0 g, 14 mmol) in methanol (100 mL), 40% methylamine in water (2.27 mL, 27.6 mmol) was added at room temperature over a period of 10 min. The mixture was stirred at room temperature under nitrogen overnight and then was cooled down to 0° C. Sodium borohydride (1.05 g, 27.6 mmol) was added. The reaction mixture was slowly warmed to room temperature for 2 h. Most of methanol was removed in vacuo, and the residue was diluted with water and extracted (3×) with ether. The combined organic layers were extracted with 2 N HCl (100 mL). The HCl layer was made basic (pH ~11) with 2 N NaOH and extracted (3×) with methylene chloride. The combined organic layers were washed with brine, dried over Na$_2$SO$_4$, and concentrated in vacuo to give crude 4-(aminomethyl)-indole as a white powder (1.95 g, 88%): $^1$H NMR (300 MHz, CDCl$_3$) δ 8.29 (s, br, 1H), 7.31 (d, J=8.0 Hz, 1H), 7.22 (t, J=2.7 Hz, 1H), 7.16 (t, J=8.0, 7.3 Hz, 1H), 7.08 (d, J=7.3 Hz, 1H), 6.64 (t, J=2.0 Hz, 1H), 4.08 (s, 2H), 2.51 (s, 3H); CI MS m/z=160 [C$_{10}$H$_{12}$N$_2$+H]$^+$.

Step D: To a mixture of amine product from Step C (1.0 g, 6.3 mmol) and 2-bromoacetophenone (1.2 g, 6.3 mmol) in anhydrous methylene chloride (20 mL), triethylamine (0.96 mL, 6.9 mmol) was added at room temperature. The reaction mixture was stirred at room temperature for 4 h and treated with water (20 mL). The organic layer was separated, and the aqueous layer was extracted (2×) with methylene chloride. The combined organic layers were washed with brine, dried over MgSO$_4$, and concentrated in vacuo. The residue was purified by chromatography (SiO$_2$, 1:2 EtoAC/hexanes) to give N-methyl-α-amino ketone (1.5 g, 86%): $^1$H NMR (300 MHz, CDCl$_3$) δ 8.32 (br s, 1H), 7.90-7.93 (m, 2H), 7.52 (m, 1H), 7.31-7.39 (m, 3H), 7.08-7.19 (m, 3H), 6.72 (t, J=1.0 Hz, 1H), 3.96 (s, 2H), 3.81 (s, 2H), 2.41 (s, 3H).

Step E: To a solution of the N-methyl-α-amino ketone product from Step D (1.5 g, 5.4 mmol) in methanol (50 mL), sodium borohydride (410 mg, 10.8 mmol) was added at 0° C. within 5 min. The reaction mixture was stirred at room temperature for 2 h. Most of the methanol was removed in vacuo, and the residue was diluted with water (100 mL) and extracted (3×) with methylene chloride. The combined organic layers were washed with brine, dried over Na$_2$SO$_4$, filtered and concentrated in vacuo to afford the crude amino alcohol product as a light yellow oil (1.5 g, 99%): $^1$H NMR (500 MHz, CDCl$_3$) δ 8.23 (br s, 1H), 7.21-7.36 (m, 7H), 7.15 (t, J=7.0 Hz, 1H), 7.04 (d, J=7.0 Hz, 1H), 6.71 (t, J=1.0 Hz, 1H), 4.73 (dd, J=10.5, 3.4 Hz, 1H), 4.03 (d, J=12.8 Hz, 1H), 3.80 (d, J=12.8 Hz, 1H), 2.65 (dd, J=12.4, 10.5 Hz, 1H), 2.58 (dd, J=12.4, 3.4 Hz, 1H), 2.38 (s, 3H); CI MS m/z=281 [C$_{18}$H$_{20}$N$_2$O+H]$^+$.

Step F: To a solution of amino alcohol product from Step E (1.37 g, 4.89 mmol) in methylene chloride (40 mL) was added methanesulfonic acid (7.93 mL, 122 mmol) at room temperature within 10 min. The reaction mixture was stirred at room temperature under nitrogen for 24 h and then was made basic (pH ~11) with 2 N NaOH. The organic layer was separated and the aqueous layer was extracted (2×) with methylene chloride. The combined organic layers were washed with brine, dried over MgSO$_4$, and concentrated in vacuo. The residue was purified by chromatography (SiO$_2$, 1:1 EtoAC/hexanes) to give the desired pyrrolo-fused tetrahydroisoquinoline product, Example 36, as a white powder (450 mg, 35%): mp 142-144° C.; $^1$H NMR (300 MHz, CDCl$_3$) δ 8.23 (br s, 1H), 7.16-7.27 (m, 6H), 7.11 (d, J=8.5 Hz, 1H), 6.70 (d, J=8.5 Hz, 1H), 6.49 (t, J=1.5 Hz, 1H), 4.37 (t, J=5.5 Hz, 1H), 4.04 (d, J=15.2 Hz, 1H), 3.85 (d, J=15.2 Hz, 1H), 3.08 (dd, J=11.5, 5.5 Hz, 1H), 2.66 (dd, J=11.5, 8.2 Hz, 1H), 2.51 (s, 3H); CI MS m/z=263 [C$_{18}$H$_{18}$N$_2$+H]$^+$; IR (KBr) 3410, 3027, 2861, 2363, 1600, 1493 cm$^{-1}$; Anal. Calcd for C$_{18}$H$_{18}$N$_2$-0.1H$_2$O: C, 81.84; H, 6.94; N, 10.60. Found: C, 81.94; H, 7.10; N, 10.46.

Example 39

To a solution of indole product from Example 38, Step F (182 mg, 0.694 mmol) and dimethyl oxalate (90 mg, 0.76 mmol) in DMF (5 mL), potassium tert-butoxide (86 mg, 0.76 mmol) was added in one portion at room temperature under nitrogen. The reaction mixture was warmed to reflux under nitrogen for 30 min and then was cooled to room temperature. The mixture was diluted with water (50 mL) and extracted (3×) with methylene chloride. The combined organic layers were washed with brine, dried over Na$_2$SO$_4$, filtered and concentrated in vacuo. The residue was purified by chromatography (SiO$_2$, EtOAc/hexanes, 1:1) to afford the N-methyl indole product, Example 37, as a white solid (180 mg, 92%): mp 106-108° C.; $^1$H NMR (500 MHz, CDCl$_3$) δ 7.19-7.28 (m, 5H), 7.05 (d, J=8.5 Hz, 1H), 7.03 (d, J=3.0 Hz, 1H), 6.73 (d, J=8.5 Hz, 1H), 6.41 (dd, J=3.0, <1 Hz, 1H), 4.37 (t, J=6.3 Hz, 1H), 4.00 (d, J=15.1 Hz, 1H), 3.85 (d, J=15.1 Hz, 1H), 3.75 (s, 3H), 3.08 (dd, J=11.4, 5.4 Hz, 1H), 2.66 (dd, J=11.4, 8.1 Hz, 1H), 2.50 (s, 3H); CI MS m/z=277 [$C_{19}H_{20}N_2$+H]$^+$; IR (KBr) 3050, 2939, 2783, 1487, 1451 cm$^{-1}$; Anal. Calcd for $C_{19}H_{20}N_2$-0.1 $H_2O$: C, 82.04; H, 7.32; N, 10.07. Found: C, 82.06; H, 7.50; N, 9.85.

Example 40

To a solution of indole product in Example 38 (150 mg, 0.572 mmol) and diethyl oxalate (92 mg, 0.63 mmol) in DMF (5 mL), potassium tert-butoxide (71 mg, 0.63 mmol) was added in one portion at room temperature under nitrogen. The reaction mixture was warmed to reflux under nitrogen for 1 h and then was cooled down to room temperature. The mixture was diluted with water (50 mL) and extracted (3×) with methylene chloride. The combined organic layers were washed with brine, dried over $Na_2SO_4$, filtered and concentrated in vacuo. The residue was purified by chromatography ($SiO_2$, EtOAc/hexanes, 1:1) to afford the N-ethyl-indole, Example 38, (144 mg, 86%): $^1$H NMR (500 MHz, CDCl$_3$) δ 7.18-7.28 (m, 5H), 7.09 (d, J=3.2 Hz, 1H), 7.07 (d, J=8.5 Hz, 1H), 6.71 (d, J=8.5 Hz, 1H), 6.42 (dd, J=3.2, <1 Hz, 1H), 4.36 (t, J=8.0, 5.4 Hz, 1H), 4.12 (q, J=7.3 Hz, 2H), 4.00 (d, J=15.1 Hz, 1H), 3.85 (d, J=15.1 Hz, 1H), 3.07 (dd, J=11.3, 5.4 Hz, 1H), 2.66 (dd, J=11.3, 8.0 Hz, 1H), 2.50 (s, 3H), 1.44 (t, J=7.3 Hz, 3H).

Example 41

To a solution of the indole product in Example 38 (150 mg, 0.572 mmol) and dibenzyl oxalate (170 mg, 0.63 mmol) in DMF (5 mL), potassium tert-butoxide (71 mg, 0.63 mmol) was added in one portion at room temperature under nitrogen. The reaction mixture was warmed to reflux under nitrogen for 3 h and then was cooled down to room temperature. The mixture was diluted with water (50 mL) and extracted (3×) with methylene chloride. The combined organic layers were washed with brine, dried over $Na_2SO_4$, filtered and concentrated in vacuo. The residue was purified by chromatography ($SiO_2$, EtOAc/hexanes, 1:1) to afford the N-benzyl-indole product, Example 39, (161 mg, 80%): $^1$H NMR (500 MHz, CDCl$_3$) δ 7.09-7.29 (m, 11H), 7.01 (d, J=8.5 Hz, 1H), 6.67 (d, J=8.5 Hz, 1H), 6.48 (dd, J=3.1, <1 Hz, 1H), 5.26 (s, 2H), 4.34 (t, J=8.1, 5.4 Hz, 1 H), 4.00 (d, J=15.1 Hz, 1H), 3.86 (d, J=15.1 Hz, 1H), 3.06 (dd, J=11.3, 5.4 Hz, 1H), 2.67 (dd, J=11.3, 8.1 Hz, 1H), 2.50 (s, 3H).

Example 42

To a solution of indole product (200 mg, 0.763 mmol) from Example 38, Step F in acetic acid (5 mL), sodium cyanoborohydride (240 mg, 3.82 mmol ) was added in portions at room temperature over a period of 5 min. The reaction mixture was stirred under nitrogen for 4 h, and then most of acetic acid was removed in vacuo. The residue was diluted with methylene chloride (100 mL), washed with 2 N NaOH and brine, dried over $Na_2SO_4$, filtered and concentrated in vacuo. The residue was purified by chromatography ($SiO_2$, EtOAc/methanol, 8:1) to afford the indoline product, Example 40, as a white solid (176 mg, 87%): mp 84-86° C.; $^1$H NMR (500 MHz, CDCl$_3$) δ 7.17-7.27 (m, 5H), 6.53 (d, J=8.0 Hz, 1H), 6.40 (d, J=8.0 Hz, 1H), 4.17 (dd, J=8.2, 5.4 Hz, 1H), 3.62 (d, J=15.0 Hz, 1H), 3.58 (t, J=8.4 Hz, 2H), 3.44 (d, J=15.0 Hz, 1H), 2.96 (dd, J=11.3, 5.4 Hz, 1H), 2.91 (dt, J=8.4, 4.0 Hz, 2H), 2.54 (dd, J=11.3, 8.2 Hz, 1 H), 2.42 (s, 3H); Cl MS m/z=265 [$C_{18}H_{20}N_2$+H]$^+$; IR (KBr) 3241, 2924, 2873, 1611, 1486 cm$^{-1}$; Anal. Calcd for $C_{18}H_{20}N_2$-0.1 $H_2O$: C, 81.23; H, 7.65; N, 10.52. Found: C, 80.87; H, 7.46; N, 10.48.

Example 43

To a solution of the indoline product of Example 42 (110 mg, 0.420 mmol) and acetic acid (0.1 mL) in methanol (4 mL), 37% aqueous formaldehyde (0.04 mL, 0.5 mmol) was added dropwise at room temperature. The reaction mixture was stirred at room temperature under nitrogen for 1 h, and then sodium cyanoborohydride (66 mg, 1.05 mmol) was added in portions at room temperature. The mixture was stirred at room temperature under nitrogen for 3 h and then quenched with 2 N NaOH and extracted (3×) with methylene chloride. The combined organic layers were washed with brine, dried over $Na_2SO_4$, filtered and concentrated in vacuo. The residue was purified by chromatography ($SiO_2$, EtOAc/methanol, 10:1) to afford the N-methyl indoline product, Example 41, as a white solid (92 mg, 80%): mp 88-90° C.; $^1$H NMR (500 MHz, CDCl$_3$) δ 7.17-7.28 (m, 5H), 6.59 (d, J=8.0 Hz, 1H), 6.26 (d, J=8.0 Hz, 1H), 4.17 (dd, J=8.5, 5.4 Hz, 1H), 3.62 (d, J=15.0 Hz, 1H), 3.43 (d, J=15.0 Hz, 1H), 3.31 (m, 2H), 2.96 (dd, J=11.3, 5.4 Hz, 1H), 2.82 (m, 2H), 2.70 (s, 3H), 2.54 (dd, J=11.3, 8.5 Hz, 1H), 2.42 (s, 3H); CI MS m/z=279 [$C_{19}H_{22}N_2$+H]$^+$; IR (KBr) 3020, 2940, 2773, 1610, 1487 cm$^{-1}$; Anal. Calcd for $C_{19}H_{22}N_2$-0.1 $H_2O$: C, 81.45; H, 7.99; N, 10.00. Found: C, 81.21; H, 8.00; N, 9.74.

Example 45

To a solution of the appropriate amino alcohol product prepared using the procedures of Step E of Example 38 (174 mg, 0.550 mmol) was dissolved in $CH_2Cl_2$ (11 mL) in a 50-mL flask under $N_2$ fitted with a condenser. The mixture was cooled to 0° C. while stirring rapidly, and MeSO$_3$H (1.8 mL, 28 mmol) was added dropwise, and the mixture stirred for 30 min while warming to rt, then heated to reflux for 48 h. The mixture was cooled to rt, neutralized with 2 N NaOH, then extracted (3×) with EtOAc. The combined organic extracts were dried over $Na_2SO_4$, filtered, and concentrated in vacuo. The crude residue was purified by silica gel chromatography (gradient 30-45% EtOAc/hexanes) to provide the desired indoleproduct (19 mg, 12%) as an orange solid: mp 164-169° C.; $^1$H NMR (300 MHz, CDCl$_3$) δ 8.18 (br s, 1H), 7.15-7.24 (m, 2H), 6.92-7.10 (m, 3H), 6.70 (d, J=8.4 Hz, 1H), 6.50-6.54 (m, 1H), 4.29 (t, J=5.8 Hz, 1H), 3.92 (d, J=4.8 Hz, 1H), 3.02 (dd, J=11.3, 5.1 Hz, 1H), 2.67 (dd, J=11.3, 6.8 Hz, 1H), 2.49 (s, 3H).

It should be noted that 55 mg (32%) of starting material was also recovered. Based on recovered starting material, the yield of Example 45 is 17%.

Example 46

The N-methyl indoline product in Example 47 (70 mg, 0.22 mmol) was dissolved in toluene (9 mL) in a 50-mL flask under $N_2$ fitted with a condenser. MnO$_2$ (199 mg, 2.3 mmol) was added, and the mixture was heated to reflux for 1.5 h. The mixture was cooled to rit, Celite, and the pad was washed several times with liberal amounts of MeOH. The filtrate was concentrated in vacuo, and the residue was purified by silica gel chromatography (gradient 25-35% EtOAc/hexane) to provide the N-methyl indole product (39 mg, 57%) as an orange oil: $^1$H NMR (300 MHz, CDCl$_3$) δ 6.93-7.11 (m, 5H), 6.72 (d, J=8.5 Hz, 1H), 6.42 (d, J=3.1 Hz, 1H), 4.29 (t, J=5.8 Hz, 1H), 3.84-3.96 (m, 2H), 3.77 (s, 3H), 2.99 (dd, J=11.3, 5.0 Hz, 1H), 2.67 (dd, J=11.3, 6.7 Hz, 1H), 2.49 (s, 3H); ESI MS m/z=313[$C_{19}H_{18}F_2N_2$+H]$^+$.

Example 47

Step A: The appropriate amino alcohol product (730 mg, 2.31 mmol) obtained using the procedures of the Example 38, Step E was dissolved in glacial HOAc (23 mL) in a 100-mL flask under $N_2$. NaBH$_3$CN (0.76 g, 12 mmol) was added in one portion, and the mixture stirred for 2 h. The mixture was poured into 200 mL of rapidly stirring ice water, and the solution was made basic with conc. NH$_4$OH. After stirring for 30 min, the mixture was extracted (4×) with CH$_2$Cl$_2$. The combined organic extracts were dried over Na$_2$SO$_4$, filtered, and concentrated in vacuo. The crude residue was purified by silica gel chromatography (gradient 25-50% EtOAc/hexanes) to provide the desired indoline product (434 mg, 59%) as an off-white solid: $^1$H NMR (300 MHz, CDCl$_3$) δ 6.98-7.23 (m, 4H), 6.62 (dd, J=16.2, 7.7 Hz, 2H), 4.67 (t, J=7.0 Hz, 1H), 3.75-4.10 (br s, 2H), 3.64 (d, J=12.8 Hz, 1H), 3.58 (t, J=8.3 Hz, 2H), 3.45 (d, J=12.7 Hz, 1H), 3.04 (t, J=8.3 Hz, 2H), 2.51 (d, J=7.0 Hz, 2H), 2.30 (s, 3H); CI MS m/z=315 [$C_{18}H_{20}F_2N_2O$+H]$^+$. It should be noted that 70 mg (10%) of starting material was also isolated. Based on recovered starting material, the yield of the indoline was 65%.

Step B: The indoline amino alcohol from Step A of this Example (165 mg, 0.518 mmol) was dissolved in dichloroethane (5 mL) in a 50-mL flask under $N_2$. MeSO$_3$H (1.7 mL, 26 mmol) was added in one portion, and the mixture was stirred rapidly while warming to reflux. After 5 h, the mixture was cooled to rt, poured into 100 mL of ice water, and made basic with 10% NaOH. After stirring for 30 min, the mixture was extracted (4×) with CH$_2$Cl$_2$. The combined organic extracts were dried over Na$_2$SO$_4$, filtered, and concentrated in vacuo. The crude residue was purified by silica gel chromatography (gradient 1-4% MeOH/CH$_2$Cl$_2$) to provide Example 45 (81 mg, 52%) as an off-white solid: mp 45-51° C.; $^1$H NMR (300 MHz, CDCl$_3$) δ 6.96-7.08 (m, 2H), 6.89-6.94 (m, 1H), 6.52 (d, J=8.0 Hz, 1H), 6.43 (d, J=8.0 Hz, 1H), 4.10 (t, J=6.0 Hz, 1H), 3.68 (br s, 1H), 3.59 (t, J=8.4 Hz, 2H), 3.50 (s, 2H), 2.85-2.93 (m, 3H), 2.54 (dd, J=11.4, 7.2 Hz, 1H), 2.41 (s, 3H); ESI MS m/z=301 [$C_{18}H_{18}F_2N_2$+H]$^+$; Anal. Calcd. for $C_{18}H_{18}F_2N_2$: C, 71.98; H, 6.04; N, 9.33. Found: C, 72.14; H, 6.69; N, 8.45.

Example 48

The indoline product from Example 47, Step B (16 mg, 0.049 mmol) was dissolved in MeOH (2 mL) in a 25-mL flask under $N_2$. A catalytic amount of HOAc (1 drop) and aqueous formaldehyde (15 μL, 0.15 mmol) were added, and the mixture stirred for 1 h. NaBH$_3$CN (16 mg, 0.25 mmol) was added, and the mixture stirred for an additional 1 h. The mixture was diluted with CH$_2$Cl$_2$ (50 mL), then washed sequentially with 0.5 N NaOH (25 mL) and sat. aq. NaCl (25 mL). The organic layer was dried over Na$_2$SO$_4$, filtered, and concentrated in vacuo to provide the N-methyl indoline product (14 mg, 87%) as an orange oil: $^1$H NMR (300 MHz, CDCl$_3$) δ 6.93-7.09 (m, 3H), 6.59 (d, J=8.1 Hz, 1H), 6.29 (d, J=8.1 Hz, 1H), 4.12 (t, J=5.8 Hz, 1H), 3.52 (s, 2H), 3.30-3.37 (m, 2H), 2.91 (dd, J=11.3, 5.1 Hz, 1H), 2.82 (t, J=8.0 Hz, 2H), 2.73 (s, 3H), 2.56 (dd, J=11.3, 7.3 Hz, 1H), 2.42 (s, 3H); CI MS m/z=315 [$C_{19}H_{20}F_2N_2$+H]$^+$.

Example 49

The appropriate indole product prepared using the procedures of Example 38, Step F (41 mg, 0.137 mmol) and dimethyl oxalate (21 mg, 0.17 mmol) were dissolved in DMF (2 mL) under rapid stirring in a 25-mL flask under $N_2$ fitted with a condenser. Potassium tert-butoxide (22 mg, 0.19 mmol) was added, and the mixture was heated to reflux for 1 h. The mixture was cooled to rt, diluted with water (100 mL), and extracted (4×) with 1:1 hexane/ether. The combined organic extracts were dried over Na$_2$SO$_4$, filtered, and concentrated in vacuo. The crude residue was purified by silica gel chromatography (25% EtOAc/hexanes) to provide the N-methyl indole product (20 mg, 47%) as a yellow oil which solidified upon standing: mp 110-112° C.; $^1$H NMR (300 MHz, CDCl$_3$) δ 7.11 (d, J=8.3 Hz, 1H), 7.06 (d, J=3.1 Hz, 1H), 6.72-6.80 (m, 3H), 6.59-6.67 (m, 1H), 6.42 (d, J=3.1 Hz, 1H), 4.30 (t, J=5.9 Hz, 1H), 3.95 (d, J=15.3 Hz, 1H), 3.85 (d, J=15.2 Hz, 1H), 3.77 (s, 3H), 3.00 (dd, J=11.3,5.1 Hz, 1H), 2.71 (dd, J=11.3, 6.6 Hz, 1H), 2.49 (s, 3H); CI MS m/z=313 [$C_{19}H_{18}F_2N_2$+H]$^+$; Anal. Calcd. for $C_{19}H_{18}F_2N_2$: C, 73.06; H, 5.81; N, 8.97. Found: C, 72.93; H, 6.08; N, 8.13.

Example 50

The analogous indoline amino alcohol product that was obtained by following the procedure described for Example 47, Step A (199 mg, 0.625 mmol) was dissolved in dichloroethane (6 mL) in a 50-mL flask under $N_2$ fitted with a condenser. MeSO$_3$H (2.0 mL, 31 mmol) was added in one portion, and the mixture was stirred vigorously while warming to reflux overnight. The mixture was cooled to rt, poured into 100 mL of rapidly stirring ice water, and made basic with 2 N NaOH. After stirring for 30 min, the mixture was extracted (4×) with CH$_2$Cl$_2$. The combined organic extracts were dried over Na$_2$SO$_4$, filtered, and concentrated in vacuo. The crude residue was purified by silica gel chromatography (gradient 50-100% EtOAc/hexanes) to provide the indoline product, Example 48 (110 mg, 55%) as an off-white solid: mp 71-75° C.; $^1$H NMR (300 MHz, CDCl$_3$) δ 6.73-6.77 (m, 2H), 6.59-6.66 (m, 1H), 6.56 (d, J=8.0 Hz, 1H), 6.45 (d, J=8.0 Hz, 1H), 4.12 (t, J=6.0 Hz, 1H), 3.72 (br s, 1H), 3.61 (t, J=8.5 Hz, 2H), 3.51 (s, 2H), 2.86-2.94 (m, 3H), 2.59 (dd, J=11.4, 7.0 Hz, 1H), 2.42 (s, 3H); API MS m/z=301 [$C_{18}H_{18}F_2N_2$+H]$^+$; It should be noted that 28 mg (14%) of starting material was also isolated. Based on recovered starting material, the yield of compound, Example 48 is 64%.

Example 51

The product in Example 50 (86 mg, 0.286 mmol) was dissolved in MeOH (3 mL) and a catalytic amount of HOAc (1 drop) in a 25-mL flask under $N_2$. Aqueous formaldehyde (24 μL, 0.32 mmol) was added, and the mixture stirred for 2 h. NaBH$_3$CN (29 mg, 0.46 mmol) was added, and the mixture stirred for an additional 1 h. The mixture was diluted with CH$_2$Cl$_2$ (50 mL), then washed sequentially with 1 N NaOH (40 mL) and sat. aq. NaCl (40 mL). The organic layer was dried over Na$_2$SO$_4$, filtered, and concentrated in vacuo. The crude residue was purified by silica gel chromatography (50% EtOAc/hexanes) to provide the N-methyl indoline product (72 mg, 80%) as a pale yellow oil which solidified upon repeated cycles of freeze/thaw/$N_2$ flushing: mp 111-116° C.; $^1$H NMR (300 MHz, CDCl$_3$) δ 6.73-6.77 (m, 2H), 6.59-6.67 (m, 2H), 6.30 (d, J=8.1 Hz, 1H), 4.12 (t, J=5.9 Hz, 1H), 3.50 (s, 2H), 3.30-3.36 (m, 2H), 2.89 (dd, J=11.4, 5.1 Hz, 1H), 2.82 (t, J=8.2 Hz, 2H), 2.73 (s, 3H), 2.59 (dd, J=11.3, 6.9 Hz, 1H), 2.41 (s, 3H); API MS m/z=315 $[C_{19}H_{20}F_2N_2+H]^+$; Anal. Calcd. for $C_{19}H_{20}F_2N_2 \cdot 0.1H_2O$: C, 72.18; H, 6.44; N, 8.86. Found: C, 72.04; H, 6.46; N, 8.65.

Example 52

To a solution of the appropriate amino alcohol prepared using the procedures of Step E of Example 38 (1.20 g, 3.81 mmol) in methylene chloride (20 mL), 98% $H_2SO_4$ (10 mL, 0.20 mol) was added dropwise at 0° C. over a period of 2 min. The reaction mixture was stirred at 0° C. for 15 min and then was poured into a mixture of ice and 2 N NaOH (300 mL). The organic layer was separated, and the aqueous layer was extracted (2×) with methylene chloride. The combined organic layers were washed with brine, dried over $MgSO_4$, filtered and concentrated in vacuo. The residue was purified by chromatography ($SiO_2$, EtOAc/hexanes, 1:1) to give the desired indole product, as a white powder (0.55 g, 48%): mp 184-186° C.; $^1H$ NMR (300 MHz, $CDCl_3$) δ 8.20 (br s, 1H), 7.08-7.22 (m, 6H), 7.69 (d, J=8.5 Hz, 1H), 6.50 (t, J=1.0 Hz, 1H), 4.32 (t, J=7.5, 5.4 Hz, 1H), 3.97 (d, J=15.2 Hz, 1H), 3.88 (d, J=15.2 Hz, 1H), 3.04 (dd, J=11.5, 5.4 Hz, 1H), 2.66 (dd, J=11.5, 7.5 Hz, 1H), 2.50 (s, 3H); CI MS m/z=297 $[C_{18}H_{17}ClN_2+H]^+$; IR (KBr) 3410, 2870, 2778, 1594, 1460, 1348 cm$^{-1}$; Anal. Calcd for $C_{18}H_{17}ClN_2$: C, 72.84; H, 5.77; N, 9.44. Found: C, 72.83; H, 5.95; N, 9.28.

Example 53

To a solution of the indole product from Example 52 (160 mg, 0.539 mmol) and dimethyl oxalate (70 mg, 0.59 mmol) in DMF (5 mL), potassium tert-butoxide (66 mg, 0.59 mmol) was added in one portion at room temperature under nitrogen. The reaction mixture was warmed to reflux under nitrogen for 30 min and then was cooled to room temperature. The mixture was diluted with water (50 mL) and extracted (3×) with methylene chloride. The combined organic layers were washed with brine, dried over $Na_2SO_4$, filtered and concentrated in vacuo. The residue was purified by chromatography ($SiO_2$, EtOAc/hexanes, 1:1) to afford the N-methyl indole product as a white solid (160 mg, 96%): mp 90-92° C.; $^1H$ NMR (300 MHz, $CDCl_3$) δ 7.03-7.23 (m, 6H), 6.71 (d, J=8.5 Hz, 1H), 6.41 (dd, J=3.0, <1 Hz, 1H), 4.33 (t, J=7.5, 5.0 Hz, 1H), 3.94 (d, J=15.1 Hz, 1H), 3.88 (d, J=15.1 Hz, 1H), 3.74 (s, 3H), 3.01 (dd, J=11.4, 5.0 Hz, 1H), 2.66 (dd, J=11.4, 7.5 Hz, 1H), 2.48 (s, 3H); CI MS m/z=311 $[C_{19}H_{19}ClN_2+H]^+$; IR (KBr) 2937, 2766, 1594, 1497, 1265 cm$^{-1}$; Anal. Calcd for $C_{19}H_{19}ClN_2 \cdot 0.1 H_2O$: C, 73.00; H, 6.19; N, 8.96. Found: C, 72.78; H, 6.09; N, 8.78.

Example 54

The appropriate indole product (200 mg, 0.763 mmol) was reduced according to the procedure described for Example 42. The reaction product was isolated and purified to give the indoline product as the free base (239 mg, 82%): $^1H$ NMR (500 MHz, $CDCl_3$) δ 7.07-7.20 (m, 4H), 6.53 (d, J=8.0 Hz, 1H), 6.43 (d, J=8.0 Hz, 1H), 4.14 (t, J=8.4, 5.4 Hz, 1H), 3.65 (br s, 1H), 3.60 (t, J=8.3 Hz, 2H), 3.58 (d, J=15.2 Hz, 1H), 3.48 (d, J=15.2 Hz, 1H), 2.96 (dd, J=11.4, 5.4 Hz, 1H), 2.91 (t, J=8.3 Hz, 2H), 2.55 (dd, J=11.4, 8.0 Hz, 1H), 2.42 (s, 3H).

To a stirring solution of the indoline free base (239 mg, 0.80 mmol) in methanol (4 mL), 1 N HCl (2.0 mL, 2.0 mmol) in ether was added dropwise at room temperature under nitrogen. The reaction mixture was stirred at room temperature for 10 min and then diluted with ether (10 mL). The resulting white solid was filtered, washed with anhydrous ether and dried at 60° C. under vacuum overnight to afford dihydrochloride salt (210 mg, 70%): mp 236-238° C.; $^1H$ NMR (300 MHz, $CD_3OD$) δ 7.25-7.43 (m, 7H), 6.95 (d, J=6.4 Hz, 1H), 4.55-4.75 (m, 4H), 3.96 (t, J=7.7 Hz, 2H), 3.86 (m, 1H), 3.61 (m, 1H), 3.35 (m, J=7.7 Hz, 2H), 3.13 (s, 3H); CI MS m/z=299 $[C_{18}H_{19}ClN_2+H]^+$; IR (KBr) 3410, 2950, 2554, 1595, 1482 cm$^{-1}$; Anal. Calcd for $C_{18}H_{19}ClN_2 \cdot 2$ HCl·0.5 $H_2O$: C, 56.78; H, 5.82; N, 7.36. Found: C, 56.74; H, 5.92; N, 7.19.

Example 55

The appropriate indole product was prepared according to the method described in Example 38, and was then reduced to the indoline product by the procedure described in Example 42.

To a solution of the resulting indoline (180 mg, 0.603 mmol) and acetic acid (0.1 mL) in methanol (5 mL), 37% aqueous formaldehyde (0.054 mL, 0.723 mmol) was added dropwise at 0° C. The reaction mixture was stirred at room temperature under nitrogen for 1 h, and then was cooled to 0° C. again. Sodium cyanoborohydride (95 mg, 1.5 mmol) was added in portions at 0° C. The mixture was stirred at room temperature under nitrogen for 3 h and then quenched with 2 N NaOH and extracted (3×) with methylene chloride. The combined organic layers were washed with brine, dried over $Na_2SO_4$, filtered and concentrated in vacuo. The residue was purified by chromatography ($SiO_2$, EtOAc/methanol, 10:1) to afford the N-methyl indoline product, Example 53 as a white solid (140 mg, 74%): mp 63-65° C.; $^1H$ NMR (300 MHz, $CDCl_3$) δ 7.07-7.20 (m, 4H), 6.59 (d, J=8.0 Hz, 1H), 6.28 (d, J=8.0 Hz, 1H), 4.14 (t, J=7.9, 5.0 Hz, 1H), 3.58 (d, J=15.0 Hz, 1H), 3.46 (d, J=15.0 Hz, 1H), 3.33 (t, J=8.2 Hz, 2H), 2.93 (dd, J=11.3, 5.0 Hz, 1H), 2.82 (t, J=8.2 Hz, 2H), 2.72 (s, 3H), 2.54 (dd, J=11.3, 7.9 Hz, 1H), 2.42 (s, 3H); CI MS m/z 313 $[C_{19}H_{21}ClN_2+H]^+$; IR (KBr) 2940, 2796, 1611, 1594, 1489, 1372, 1286 cm$^{-1}$; Anal. Calcd for $C_{19}H_{21}ClN_2$: C, 72.95; H, 6.77; N, 8.95. Found: C, 72.70; H, 6.83; N, 8.78.

Example 56

Sulfuric acid (5.0 mL) was added to a solution of the appropriate amino alcohol prepared using the procedures of Step E of Example 38 (500 mg, 1.68 mmol) in dichloromethane (25 mL) at 0° C. The reaction mixture was stirred at 0° C. under nitrogen for 20 minutes. After the reaction was complete, the reaction was made basic (pH ~11) with 6 N NaOH, and extracted (3×) with methylene chloride. The combined organic layers were washed with brine, dried over $Na_2SO_4$, filtered and concentrated in vacuo to yield a brown oil, which was chromatographed ($SiO_2$, 20% EtOAc/hexanes) to provide the desired indole as an off-white powder (120 mg, 34%): mp 150-152° C.; $^1H$ NMR (300 MHz, $CDCl_3$) δ 8.21 (br s, 1H), 7.25-7.17 (m, 2H), 7.14 (d, J=8.6 Hz, 1H), 7.01 (d, J=7.7 Hz, 1H), 6.93-6.85 (m, 2H), 6.70 (d, J=8.5 Hz, 1H), 6.50 (d, J=2.3 Hz, 1H), 4.35 (t, J=6.3 Hz, 1H), 3.97 (d, J=15.3 Hz, 1Hz, 1H), 3.89 (d, J=15.3 Hz, 1H), 3.05 (dd, J=5.2, 11.3 Hz, 1H), 2.68 (dd, J=7.5, 11.3 Hz, 1H), 2.50 (s, 3H); IR (KBr) 3427, 2921, 2473, 1617, 1590, 1484 cm$^{-1}$; CI MS m/z=281 $[C_{18}H_{17}FN_2+H]^+$.

Example 57

The indole product from Example 56 (100 mg, 0.36 mmol) and dimethyl oxalate (46 mg, 0.39 mmol) in DMF (3 mL) were treated with potassium t-butoxide (44 mg, 0.39 mmol). The reaction was heated at reflux for 30 min. Reaction was cooled to room temperature and diluted with water (25 mL). Following extractions (3×) with ethyl acetate, the organic layers were washed with water, brine, dried over sodium sulfate, filtered and concentrated. The dark residue was chromatographed ($SiO_2$, 20% EtOAc/hexanes), and the resulting oil was treated with 1 M HCl (1 eq) in diethyl ether to provide the N-methyl indole product as a white solid (45 mg, 11%): mp 255-258° C.; $^1$H NMR (300 MHz, $CD_3OD$) δ 7.43-7.25 (m, 3H), 7.12-7.00 (m, 2H), 6.99 (d, J=10.0 Hz, 1H), 6.70 (d, J=8.6 Hz, 1H), 6.50 (d, J=3.1 Hz, 1H), 4.80-4.67 (m, 2H), 3.89 (dd, J=5.6, 11.9 Hz, 1H), 3.81 (s, 3H), 3.65-3.55 (m, 1H), 3.30-3.29 (m, 1H), 3.14 (s, 3H); IR (KBr) 3424, 2944, 2479, 1590, 1449 $cm^{-1}$; CI MS m/z=295 $[C_{19}H_{19}FN_2+H]^+$.

Example 59

A 1 M HCl ether solution (2.0 mL, 2.0 mmol) was added dropwise to a solution of the appropriate amino alcohol prepared using the procedures of Step E of Example 38 (129 mg, 0.459 mmol) in methanol (4 mL). The solvents and excess HCl were removed in vacuo leaving a brown solid, which was recrystallized from $EtOH-Et_2O$ to give the desired indole product (64 mg, 42%) as a brown solid: mp 200-205° C. (with decomposition); $^1$H NMR (300 MHz, $CD_3OD$) δ 7.36-7.23 (m, 4H), 7.10 (t, J=8.7 Hz, 2H), 6.62 (d, J=8.5 Hz, 1H), 6.52 (d, J=3.0 Hz, 1H), 4.82-4.69 (m, 3H) 3.85 (dd, J=11.3, 5.8 Hz, 1H), 3.56 (t, J=11.5 Hz, 1H), 3.14 (s, 3H); IR (KBr) 3238, 2954, 2588, 1605, 1509, 1463, 1348, 1224, 1160, 838, 740 $cm^{-1}$; CI MS m/z=281 $[C_{18}H_{17}FN_2+H]^+$; Anal. Calcd. for $C_{18}H_{17}FN_2$—HCl-0.75 $H_2O$: C, 65.45, 5.95; N, 8.48. Found: C, 65.75; H, 5.94; N, 8.42.

Example 61

Concentrated sulfuric acid (10.0 mL, 30.1 mmol) was added to an ice-cold stirred solution of the appropriate amino alcohol prepared using the procedures of Step E of Example 38 (1.00 g, 3.05 mmol) in $CH_2Cl_2$ (50 mL). This mixture was stirred at 0° C. for 20 min, then stirred at room temperature for 30 min and cooled to −10° C. Ice-cold concentrated aq. ammonium hydroxide was added in small portions (200 mL) until the solution reached pH 12. The aqueous layer was extracted (2×) with $CH_2Cl_2$. The organic extracts were combined, dried over $MgSO_4/Na_2SO_4$, filtered, and concentrated in vacuo. Purification by column chromatography ($SiO_2$, 20 g, hexanes to 10% EtOAc/hexanes) gave the desired indole product (302 mg, 32%) as an off-white solid: mp 149-153° C.; $^1$H NMR (500 MHz, $CDCl_3$) δ 8.16 (s, 1H), 7.28-7.21 (m, 2H), 7.16 (d, J=8.4 Hz, 1H), 7.02 (d, J=10.4 Hz, 1H), 6.97 (d, J=8.2 Hz, 1H), 6.70 (d, J=8.4 Hz, 1H), 6.51 (s, 1H), 4.29 (t , J=5.2 Hz, 1H), 3.96 (d, J=15.2 Hz, 1H), 3.87 (d, J=15.3 Hz, 1H), 3.00 (dd, J=11.2, 5.0 Hz, 1H), 2.69 (dd, J=11.3, 6.5 Hz, 1H), 2.49 (s, 3H). IR (KBr) 3409, 2779, 1579, 1489, 1424, 1349, 1244, 1163, 1060 $cm^{-1}$; CI MS m/z=315 $[C_{18}H_{16}ClFN_2+H]^+$; Anal. Calcd. for $C_{18}H_{16}ClFN_2$: C, 68.68; H, 5.12; N, 8.90. Found: C, 68.36; H, 5.13; N, 8.51.

Example 62

Potassium tert-butoxide was added to a solution of the indole product of Example 61 (354 mg, 1.12 mmol) and dimethyl oxalate (145 mg, 1.23 mmol) in DMF (3 mL) and heated to reflux for 1 h. The mixture was cooled to room temperature and quenched with water (5 mL). After extraction (2×) with $CH_2Cl_2$, the organic layer was dried over $MgSO_4/Na_2SO_4$, filtered, and concentrated in vacuo. Purification by column chromatography ($SiO_2$, 20 g, hexanes to 10% EtOAc/hexanes) provide the N-methyl indole product (163 mg, 44%) as a yellow powder: mp 120-124° C.; $^1$H NMR (500 MHz, $CDCl_3$) δ 7.27-7.24 (m, 1H), 7.08 (d, J=8.5 Hz, 1H), 7.04 (d, J=3.1 Hz, 1H), 7.01 (d, J=10.4 Hz, 1H), 6.96 (d, J=8.2 Hz, 1H), 6.71 (d, J=8.5 Hz, 1H), 6.42 (d, J=3.1 Hz, 1H), 4.29 (t, J=5.8 Hz, 1H), 3.96 (d, J=15.2 Hz, 1H), 3.85 (d, J=15.2 Hz, 1H), 3.76 (s, 3H), 2.99 (dd, J=11.3, 5.2 Hz, 1H), 2.68 (dd, J=11.4, 6.5 Hz, 1H), 2.47 (s, 3H); IR (KBr) 3438, 2943, 2779, 1579, 1488, 1422, 1358, 1266, 1064 $cm^{-1}$; ESI MS m/z=329 $[C_{19}H_{18}ClFN_2+H]^+$.

Example 64

The analogous N-methyl indole product was prepared according to the method described in Example 39, and was then reduced to the indoline product by the following procedure.

Sodium cyanoborohydride (63 mg, 1.004 mmol) was added to an ice-cold solution of the N-methyl indole (110 mg, 0.335 mmol) in glacial acetic acid (6 mL). The reaction mixture was allowed to warm to room temperature, stirred for 2 h, cooled in an ice bath, and diluted with $H_2O$ (10 mL). Ice-cold concentrated aq. ammonium hydroxide (30 mL) was added until the solution reached pH 12. After extraction (2×) with $CH_2Cl_2$, the organic layer was dried over $MgSO_4/Na_2SO_4$, filtered, and concentrated in vacuo. Purification by column chromatography ($SiO_2$, 10 g, 10% EtOAc/hexanes) gave the desired N-methyl indoline product (15 mg, 15%) as brown oil. The material is air-sensitive and requires storage under nitrogen: $^1$H NMR (500 MHz, $CDCl_3$) δ 7.28-7.25 (m, 1H), 7.01 (dd, J=10.4, 2.0 Hz, 1H), 6.95 (dd, J=8.2,1.9 Hz, 1H), 6.59 (d, J=8.1 Hz, 1H), 6.28 (d, J=8.1 Hz,1H), 4.11 (t, J=5.9 Hz 1H), 3.50 (dd,J=13, 2.0 Hz, 2H), 3.36-3.32 (m, 2H), 2.88 (dd, J=11.3, 5.2 Hz, 1H), 2.82 (t, J=8.2 Hz, 2H), 2.73 (s, 3H), 2.56 (dd, J=11.4, 7.0 Hz, 1H), 2.41 (s, 3H); IR (KBr) 3052, 2925, 2850, 2786, 1609, 1422, 1265, 739 $cm^{-1}$; ESI MS m/z=331 $[C_{19}H_{20}ClFN_2+H]^+$.

Example 65

A solution of the appropriate amino alcohol prepared using the procedures of Step E of Example 38 (2.00 g, 6.01 mmol) in $CH_2Cl_2$ (50 mL), cooled to 0° C., was added dropwise to conc. $H_2SO_4$ (20 mL), cooled to 0° C. under $N_2$. After stirring for 20 min at 0° C., the reaction mixture was poured onto an ice-water mixture (400 mL). The aqueous layer was quenched with 6 N NaOH, until pH ~14, then the aqueous layer was extracted (3×) with $CH_2Cl_2$. The combined $CH_2Cl_2$ extract was washed with a 1:5 mixture of 6 N NaOH and sat. NaCl, then dried over $Na_2SO_4$, filtered and concentrated in vacuo. Chromatography on silica (60 g) and elution with 66% EtOAc afforded (0.68 g, 36%). Recrystallization from $CH_2Cl_2$/MeOH/hexanes afforded the desired indole product (0.12 g) as an off-yellow solid: mp 189-195° C.; $^1$H NMR (300 MHz, 5% MeOH-$D_4$/$CDCl_3$) δ 8.66 (br s, 1H), 7.28-7.20 (m, 2H) 7.16 (d, J=8.6 Hz, 1H), 7.11-6.97 (m, 2H), 6.66 (d, J=8.5 Hz, 1H), 6.52-6.47 (m, 1H), 4.34 (t, J=6.5 Hz, 1H), 4.00 (d, J=15.2 Hz, 1H), 3.89 (d, J=15.2 Hz, 1H), 3.05 (dd, J=11.1, 5.8 Hz, 1H), 2.63 (dd, J=11.4, 8.0 Hz, 1H), 2.51 (s, 3H); IR (KBr) 3410, 2780, 1498, 1461, 1347, 1247, 1132, 1059, 883, 824, 801, 736, 690, 560 cm$^{-1}$; ESI MS m/z=315 [C$_{18}$H$_{16}$ClFN$_2$+H]$^+$; Anal. Calcd. For C$_{18}$H$_{16}$ClFN$_2$-0.10H$_2$O: C, 68.29; H, 5.16; N, 8.85. Found: C, 68.17; H, 4.95; N, 8.68.

Example 81

Step A: Methylamine (40 wt % aqueous, 2.0 mL, 23 mmol) was added to a stirred solution of 5-formylbenzofuran (8.2 g, 56 mmol) in MeOH (55 mL). After stirring for 20 min, the mixture was cooled with an ice-water bath for 35 min, and then NaBH$_4$ (1.3 g, 34 mmol) was added portionwise over 15 min. After stirring for 30 min, H$_2$O (5 mL) was added to quench any remaining hydride. After stirring for 15 min, the MeOH was removed in vacuo, the residue was dissolved in 1 N HCl, and then was extracted (2×) with Et$_2$O. The aqueous phase was made strongly alkaline (pH 11) by adding excess conc. NH$_4$OH, then extracted (2×) with Et$_2$O. The organic phase was washed with satd. NaCl, dried over Na$_2$SO$_4$, filtered, and the solvent was removed in vacuo to give compound the reductive alkylation product (4.2 g, theoretical yield=3.8 g) as a clear, yellow liquid: $^1$H NMR (300 MHz, CDCl$_3$) δ 7.61 (d, J=2.3 Hz, 1H), 7.54 (s, 1 H), 7.45 (s, 1 H), 7.25 (dd, J=8.5, 1.7 Hz, 1 H), 6.74 (d, J=2.7 Hz, 1 H), 3.83 (s, 2 H), 2.47 (s, 3 H).

Step B: 2-Bromoacetophenone (5.12 g, 26 mmol) was added to a stirred solution of the methyl amine product from Step A (4.08 g, 25 mmol) and DIEA (5.5 mL, 31 mmol) in anhydrous CH$_2$Cl$_2$ (50 mL) under N$_2$. After stirring for 20 h, the mixture was diluted with Et$_2$O and then washed (2×) with 1 N HCl. The aqueous phase was made strongly alkaline (pH 12) by adding excess conc. NH$_4$OH, then extracted (2×) with Et$_2$O. The organic phase was dried over Na$_2$SO$_4$, filtered, the solvent was removed in vacuo, and the residue was purified by flash column chromatography on silica gel using 2% to 14% EtOAc/hexanes +1% Et$_3$N to give the amino ketone (4.32 g, 61%) as a clear, dark yellow oil: $^1$H NMR (300 MHz, CDCl$_3$) δ 7.94 (dd, J=8.5, 1.2 Hz, 2 H), 7.51-7.62 (m, 3 H), 7.38-7.47 (m, 3 H), 7.30 (dd, J=8.5, 1.7 Hz, 1 H), 6.72 (d, J=2.9 Hz, 1 H), 3.83 (s, 2 H), 3.79 (s, 2 H), 2.41 (s, 3 H).

Step C: Following the procedure described in Example 10, Step G, the amino ketone prepared in Step B (4.31 g, 15.4 mmol) was used to prepare the amino alcohol (3.61 g, 83%) as a clear, yellow oil: $^1$H NMR (300 MHz, CDCl$_3$) δ 7.62 (d, J=2.0 Hz, 1H), 7.52 (d, J=0.9 Hz, 1 H), 7.47 (d, J=8.5 Hz, 1 H), 7.22-7.48 (m, 6 H), 6.72-6.75 (m, 1 H), 4.76 (dd, J=10.3, 3.7 Hz, 1 H), 3.83 (d, J=12.9 Hz, 1 H), 3.61 (d, J=12.9 Hz, 1 H), 2.63 (dd, J=12.4, 10.2 Hz, 1 H), 2.54 (dd, J=12.4, 3.7 Hz, 1 H), 2.33 (s, 3 H).

Step D: Methanesulfonic acid (15.5 mL, 239 mmol) was added to a stirred solution of the amino alcohol (3.45 g, 12 mmol prepared in Step C) in CH$_2$Cl$_2$ (60 mL) under N$_2$. Then the mixture was heated to reflux for 6 h, and allowed to cool to room temperature. The CH$_2$Cl$_2$ was removed in vacuo, and the resulting CH$_3$SO$_3$H solution was poured onto ice with stirring. The mixture was made strongly alkaline (pH 12) by adding excess conc. NH$_4$OH, then extracted (2×) with Et$_2$O. The organic phase was washed with satd. NaCl, dried over Na$_2$SO$_4$, filtered, the solvent removed in vacuo, and the residue was purified by flash column chromatography on silica gel using 5% to 15% EtOAc/hexanes +1% Et$_3$N to give (in order of elution): (i) Compound A (1.65 g, 51%) as a clear, pale yellow oil: $^1$H NMR(300 MHz, CDCl$_3$) δ 7.16-7.39 (m, 7 H); 7.04 (d, J=8.4 Hz, 1 H), 5.97-6.00 (m, 1 H), 4.47 (t, J=6.6 Hz, 1 H), 3.75 (s, 2 H), 3.09 (dd, J=11.6, 5.8 Hz, 1 H), 2.62 (dd, J=11.7, 7.5 Hz, 1 H), 2.44 (s, 3 H); (ii) a 9:1 mixture (0.44 g, 14%) of compounds B and A; (iii) compound A (0.54 g, 17%) as a clear, yellow oil: $^1$H NMR (300 MHz, CDCl$_3$) δ 7.50 (d, J=2.3 Hz, 1H), 7.19-7.37 (m, 6 H), 6.99 (s, 1 H), 6.66-6.69 (m, 1 H), 4.40 (dd, J=8.8, 5.8 Hz, 1 H), 3.89 (d, J=14.3 Hz, 1 H), 3.70 (d, J=14.3 Hz, 1 H), 3.08 (ddd, J=11.6, 5.8, 1.5 Hz, 1 H), 2.59 (dd, J=11.6, 9.2 Hz, 1 H), 2.45 (s, 3 H).

Step E: Ethereal HCl (1 M, 5 mL) was added to a stirred solution of compound B (0.53 g, 2.0 mmol, from Step D) in MeOH (20 mL). After stirring for 20 min, the solvent was removed in vacuo, the residue was redissolved in MeOH, and the solvent removed again in vacuo. The residue was recrystallized from EtOH-Et$_2$O to give compound, Example 67 (405 mg, 68%) as a white, crystalline solid: mp 241-246° C.; $^1$H NMR (300 MHz, CD$_3$OD) δ 7.75 (d, J=2.2 Hz, 1 H), 7.56 (s, 1 H), 7.33-7.47 (m, 3 H), 7.27-7.33 (m, 2 H), 6.98 (s, 1 H), 6.84-6.87 (m, 1 H), 4.66-4.77 (m, 3 H), 3.87 (dd, J=12.3, 6.4 Hz, 1 H), 3.60 (t, J=11.9 Hz, 1 H), 3.10 (s, 3 H); IR (KBr) 3432, 2954, 2476, 1468, 1275, 1124, 701 cm$^{-1}$; CI MS m/z=264 [C$_{18}$H$_{17}$NO+H]$^+$; Anal. Calcd. for C$_{18}$H$_{17}$NO—HCl-0.1 H$_2$O: C, 71.68; H, 6.08; N, 4.64. Found: C, 71.53; H, 6.04; N, 4.56.

Example 123

Following the procedure described for the preparation of Example 81, Step E, compound A (0.83 g, 3.2 mmol, from Example 81, Step C) was used to prepare Example 123 (385 mg, 41%) as a white, amorphous solid: mp 234-240° C.; $^1$H NMR (300 MHz, CD$_3$OD) δ 7.50-7.60 (m, 2 H), 7.29-7.42 (m, 3 H), 7.20- 7.28 (m, 3 H), 5.95 (br s, 1 H), 4.83-4.91 (m, 1 H), 4.69 (d, J=15.2 Hz, 1 H), 4.62 (d, J=15.2 Hz, 1 H), 3.97 (dd, J=12.4, 6.7 Hz, 1 H), 3.53 (br t, J=11.4 Hz, 1 H), 3.09 (s, 3 H); IR (KBr) 3424, 2936, 2588, 1466, 1431, 1268, 1148, 1039, 780, 705 cm$^{-1}$; CI MS m/z=264 [C$_{18}$H$_{17}$NO+H]$^+$; Anal. Calcd. for C$_{18}$H$_{17}$NO—HCl-0.5 H$_2$O: C, 70.01; H, 6.20; N, 4.54. Found: C, 70.05; H, 6.06; N, 4.46.

Binding Assays

Primary Binding Assays

In order to evaluate the relative affinity of the various compounds at the NE, DA and 5HT transporters, HEK293E cell lines were developed to express each of the three human transporters. cDNAs containing the complete coding regions of each transporter were amplified by PCR from human brain libraries. The cDNAs contained in pCRII vectors were sequenced to verify their identity and then subcloned into an Epstein-Barr virus based expression plasmid (E. Shen, G M Cooke, R A Horlick, Gene 156:235-239, 1995). This plasmid containing the coding sequence for one of the human transporters was transfected into HEK293E cells. Successful transfection was verified by the ability of known reuptake blockers to inhibit the uptake of tritiated NE, DA or 5HT.

For binding, cells were homogenized, centrifuged and then resuspended in incubation buffer (50 mM Tris, 120 mM NaCl, 5 mM KCl pH 7.4). Then the appropriate radioligand was added. For NET binding, [$^3$H] Nisoxetine (86.0 Ci/mmol, NEN/DuPont) was added to a final concentration of approximately 5 nM. For DAT binding, [$^3$H] WIN 35,428 (84.5 Ci/mmol) at 15 nM was added. For 5HTT binding, [$^3$H] Citolapram (85.0 Ci/mmol) at 1 nM was added. Then various concentrations (10 ^-5 to 10 ^-11 M) of the compound of interest were added to displace the radioligand. Incubation was carried out at room temperature for 1 hour in a 96 well plate. Following incubation, the plates were placed on a harvester and washed quickly 4 times with (50 mM tris, 0.9% NaCl, pH 7.4) where the cell membranes containing the bound radioactive label were trapped on Whatman GF/B filters. Scintillation cocktail was added to the filters which were then counted in a Packard TopCount. Binding affinities of the compounds of interest were determined by non-linear curve regression using GraphPad Prism 2.01 software. Nonspecific binding was determined by displacement with 10 micromolar mazindol.

TBZ Assay

In order to assess in vivo activity of the compounds at the NE and DA transporters, their ability to prevent the sedative effects of tetrabenazine (TBZ) was determined (G. Stille, Arzn. Forsch 14:534-537, 1964). Male CFI mice (Charles River Breeding Laboratories) weighing 18-25 gm at the time of testing, are housed a minimum of(06 days under carefully controlled environmental conditions (22.2+1.1 C; 50% average humidity; 12 hr lighting cycle/24 hr). Mice are fasted overnight (16-22 hr) prior to testing. Mice are placed into clear polycarbonated "shoe" boxes (17 cm×28.5 cm×12 cm). Randomized and coded doses of test compounds are administered p.o. A 45 mg/kg dose of tetrabenazine is administered i.p. 30 minutes prior to score time. All compounds are administered in a volume of 0.1 ml/10 gm body weight. Animals are evaluated for antagonism of tetrabenazine induced exploratory loss and ptosis at specified time intervals after drug administration. At the designated time interval, mice are examined for signs of exploratory activity and ptosis. Exploratory activity is evaluated by placing the animal in the center of a 5 inch circle. Fifteen seconds are allowed for the animal to move and intersect the perimeter. This is considered antagonism of tetrabenazine and given a score of 0. Failure to leave the circle is regarded as exploratory loss and given a score of 4. An animal is considered to have ptosis if its eyelids are at least 50% closed and given a score of 4 if completely closed; no closure is given a score of 0. Greater than 95% of the control (vehicle-treated) mice are expected to exhibit exploratory loss and ptosis. Drug activity is calculated as the percentage of mice failing to respond to the tetrabenazine challenge dose.

Statistical Evaluation

Median effective doses ($ED_{50}s$) and 95% confidence limits are determined numerically by the methods of Thompson (1947) and Litchfield and Wilcoxon (1949).

What is claimed is:
1. A compound of Formula (50):

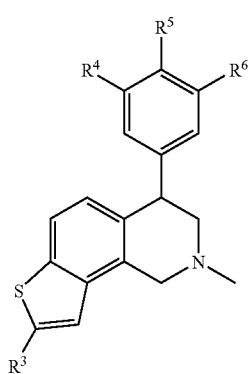

(50)

or a pharmaceutically acceptable salt form thereof, wherein $R^3$ is H, $R^4$ is H, $R^5$ is H and $R^6$ is H.

2. A compound of Formula (60):

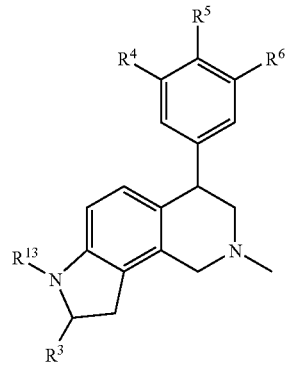

(60)

or a pharmaceutically acceptable salt form thereof selected from the group consisting of:
a compound of Formula (60) wherein $R^3$ is H, $R^4$ is H, $R^5$ is H and $R^6$ is H and $R^{13}$ is H;
a compound of Formula (60) wherein $R^3$ is H, $R^4$ is H, $R^5$ is H, $R^6$ is H and $R^{13}$ is Me;
a compound of Formula (60) wherein $R^3$ is H, $R^4$ is H, $R^5$ is H, $R^6$ is H and $R^{13}$ is Et;
a compound of Formula (60) wherein $R^3$ is H, $R^4$ is H, $R^5$ is F, $R^6$ is F and $R^{13}$ is H;
a compound of Formula (60) wherein $R^3$ is H, $R^4$ is H, $R^5$ is F, $R^6$ is F and $R^{13}$ is Me;
a compound of Formula (60) wherein $R^3$ is H, $R^4$ is H, $R^5$ is F, $R^6$ is F and $R^{13}$ is H;
a compound of Formula (60) wherein $R^3$ is H, $R^4$ is F, $R^5$ is H, $R^6$ is F and $R^{13}$ is Me;
a compound of Formula (60) wherein $R^3$ is H, $R^4$ is Cl, $R^5$ is H, $R^6$ is H and $R^{13}$ is H;
a compound of Formula (60) wherein $R^3$ is H, $R^4$ is Cl, $R^5$ is H, $R^6$ is H and $R^{13}$ is Me;
a compound of Formula (60) wherein $R^3$ is H, $R^4$ is F, $R^5$ is H, $R^6$ is H and $R^{13}$ is H;
a compound of Formula (60) wherein $R^3$ is H, $R^4$ is H, $R^5$ is F, $R^6$ is H and $R^{13}$ is H;
a compound of Formula (60) wherein $R^3$ is H, $R^4$ is F, $R^5$ is Cl, $R^6$ is H and $R^{13}$ is H;
a compound of Formula (60) wherein $R^3$ is H, $R^4$ is F, $R^5$ is Cl, $R^6$ is H and $R^{13}$ is Me;
a compound of Formula (60) wherein $R^3$ is H, $R^4$ is Cl, $R^5$ is F, $R^6$ is H and $R^{13}$ is H; and
a compound of Formula (60) wherein $R^3$ is H, $R^4$ is Cl, $R^5$ is F, $R^6$ is H and $R^{13}$ is Me.

3. A compound of Formula (70):

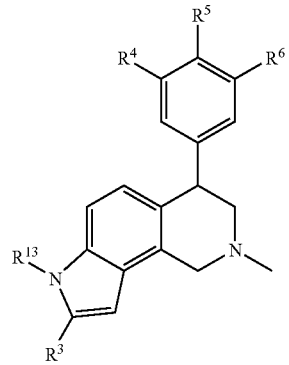

(70)

or a pharmaceutically acceptable salt form thereof selected from the group consisting of:
- a compound of Formula (70) wherein $R^3$ is H, $R^4$ is H, $R^5$ is H, $R^6$ is H and $R^{13}$ is H;
- a compound of Formula (70) wherein $R^3$ is H, $R^4$ is H, $R^5$ is H, $R^6$ is H and $R^{13}$ is Me;
- a compound of Formula (70) wherein $R^3$ is H, $R^4$ is H, $R^5$ is H, $R^6$ is H and $R^{13}$ is Et;
- a compound of Formula (70) wherein $R^3$ is H, $R^4$ is H, $R^5$ is H, $R^6$ is H and $R^{13}$ is Bn;
- a compound of Formula (70) wherein $R^3$ is H, $R^4$ is H, $R^5$ is F, $R^6$ is F and $R^{13}$ is H;
- a compound of Formula (70) wherein $R^3$ is H, $R^4$ is H, $R^5$ is F, $R^6$ is F and $R^{13}$ is Me;
- a compound of Formula (70) wherein $R^3$ is H, $R^4$ is F, $R^5$ is H, $R^6$ is F and $R^{13}$ is Me;
- a compound of Formula (70) wherein $R^3$ is H, $R^4$ is Cl, $R^5$ is H, $R^6$ is H and $R^{13}$ is H;
- a compound of Formula (70) wherein $R^3$ is H, $R^4$ is Cl, $R^5$ is H, $R^6$ is H and $R^{13}$ is Me;
- a compound of Formula (70) wherein $R^3$ is H, $R^4$ is F, $R^5$ is H, $R^6$ is H and $R^{13}$ is H;
- a compound of Formula (70) wherein $R^3$ is H, $R^4$ is F, $R^5$ is H, $R^6$ is H and $R^{13}$ is Me;
- a compound of Formula (70) wherein $R^3$ is H, $R^4$ is H, $R^5$ is F, $R^6$ is H and $R^{13}$ is H;
- a compound of Formula (70) wherein $R^3$ is H, $R^4$ is F, $R^5$ is Cl, $R^6$ is H and $R^{13}$ is H;
- a compound of Formula (70) wherein $R^3$ is H, $R^4$ is F, $R^5$ is Cl, $R^6$ is H and $R^{13}$ is Me;
- a compound of Formula (70) wherein $R^3$ is H, $R^4$ is Cl, $R^5$ is F, $R^6$ is H and $R^{13}$ is H; and
- a compound of Formula (70) wherein $R^3$ is H, $R^4$ is Cl, $R^5$ is F, $R^6$ is H and $R^{13}$ is Me.

4. A compound of Formula (100):

(100)

or a pharmaceutically acceptable salt form thereof, wherein $R^4$ is H, $R^5$ is H, $R^6$ is H and $R^{13}$ is H.

5. A compound of Formula (130):

(130)

or a pharmaceutically acceptable salt form thereof selected from the group consisting of:
- a compound of Formula (130) wherein $R^4$ is H, $R^5$ is H and is $R^6$ is H; and
- a compound of Formula (130) wherein $R^4$ is H, $R^5$ is Bn and $R^6$ is H.

6. A compound of Formula (160):

(160)

or a pharmaceutically acceptable salt form thereof, wherein $R^4$ is H, $R^5$ is H and $R^6$ is H.

7. A compound of Formula (190):

(190)

or a pharmaceutically acceptable salt form thereof, wherein $R^4$ is H, $R^5$ is H and $R^6$ is H.

8. A compound of Formula (200):

(200)

or a pharmaceutically acceptable salt form thereof selected from the group consisting of:
- a compound of Formula (200) wherein $R^4$ is H, $R^5$ is H, $R^6$ is H and $R^{13}$ is H; and
- a compound of Formula (200) wherein $R^4$ is H, $R^5$ is H, $R^6$ is H and $R^{13}$ is Me.

* * * * *